(12) United States Patent
Rangan et al.

(10) Patent No.: US 6,620,990 B1
(45) Date of Patent: *Sep. 16, 2003

(54) TRANSFORMATION OF COTTON PLANTS

(75) Inventors: Thirumale S. Rangan, San Dimas, CA (US); David M. Anderson, Altadena, CA (US); Kanniah Rajasekaran, Duarte, CA (US); John W. Grula, Pasadena, CA (US); Richard Lorne Hudspeth, Altadena, CA (US); Richard L. Yenofsky, Arcadia, CA (US)

(73) Assignee: Mycogen Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/122,090

(22) Filed: Sep. 14, 1993

Related U.S. Application Data

(62) Division of application No. 07/680,048, filed on Mar. 29, 1991, now Pat. No. 5,244,802, and a continuation-in-part of application No. 07/680,048, which is a continuation of application No. 07/122,200, filed on Nov. 18, 1987, now abandoned.

(51) Int. Cl.[7] .................. C12N 15/82; C12N 15/54; C12N 15/84; A01H 4/00
(52) U.S. Cl. .................. 800/314; 800/278; 800/288; 800/294; 800/300; 435/427; 435/430; 435/430.1; 435/431; 435/468; 435/469; 435/194
(58) Field of Search ............... 435/172.3, 240.46, 435/240.5, 240.54, 427, 468, 469, 430, 430.1, 431, 194; 800/205, DIG. 27, 63, 278, 288, 294, 302, 314, 300

(56) References Cited

U.S. PATENT DOCUMENTS

| | | | |
|---|---|---|---|
| 4,535,060 A | | 8/1985 | Comai |
| 4,672,035 A | | 6/1987 | Davidonis et al. ........ 435/240 |
| 4,769,061 A | | 9/1988 | Comai |
| 4,774,381 A | | 9/1988 | Chaleff et al. |
| 4,827,079 A | | 5/1989 | Evans et al. |
| 4,940,835 A | * | 7/1990 | Shah et al. .............. 800/205 |
| 5,004,863 A | * | 4/1991 | Umbeck ................. 800/205 |
| 5,024,944 A | | 6/1991 | Collins |
| 5,159,135 A | * | 10/1992 | Umbeck ................. 800/205 |
| 5,169,770 A | | 12/1992 | Chee et al. |
| 5,188,642 A | | 2/1993 | Shah et al. |
| 5,244,802 A | | 9/1993 | Rangan |
| 5,495,071 A | | 2/1996 | Fischhoff et al. |
| 5,607,142 A | | 3/1997 | Nilsson |
| 5,608,142 A | | 3/1997 | Barton et al. |
| 5,763,241 A | | 6/1998 | Fishhoff et al. |

FOREIGN PATENT DOCUMENTS

| | | | | |
|---|---|---|---|---|
| AU | 610157 | | 11/1988 | |
| AU | A 15273/88 | | 11/1988 | |
| AU | A-2568088 | | 5/1989 | ........ A01G/31/00 |
| AU | A 25681/88 | | 5/1989 | |
| BR | 8405897 | | 9/1985 | |
| EP | 142924 | * | 5/1985 | |
| EP | 0218571 | | 4/1987 | ........ C12N/15/00 |
| EP | 0270355 | | 6/1988 | ........ C12N/15/00 |
| EP | 0289479 | | 11/1988 | ........ C12N/15/00 |
| EP | 0317511 | | 5/1989 | ........ C12N/15/00 |
| WO | WO 86/03516 | | 6/1986 | ........ C12N/15/00 |
| WO | 02701/87 | | 5/1987 | |
| WO | WO 87/02701 | | 5/1987 | ........ C12N/5/00 |

OTHER PUBLICATIONS

Finer et al. 1984. Dep. Soil Crop Sci., pp. 8–17.*
Mitten, D. 1985. pp. 57–58 In: Proc.Beltwide Cotton Produ. Res. Conf., 1/6–1/11, New Orleans, LA.*
Shoemaker et al. 1986. Plant Cell Reports 5(3):178–181.*
Rangan et al. 1984. In Vitro 20:256.*
Finer et al. 1984. Plant Cell Reports 3:41–43.*
Cousins et al. Aust. J. Plant Physiol. 18: 481–494, 1991.*
Fraley et al. pp. 1–46 In: Critical Reviews in Plant Sciences, CRC Press, vol. 4, Issue 1, 1986.*
Ecker et al. Proc. Natl. Acad Sci. USA 83: 5372–5376, Aug. 1986.*
Brown et al. pp. 345–415 In: In Vitro Embryogen Plants, T.A. Thorpe (ed.), Kluwer Academic: Dordrecht, 1995.*
Gurlitz et al. Plant Physiol. 83: 564–568, 1987.*
Matthysse, A. J. Bacteriol. 154: 906–915, May, 1983.*
Matthysse et al. J. Bacteriol. 145(1): 583–595, Jan. 1982.*
Matthysse et al. Physiol. Plant Pathol. 21: 381–387, 1982.*
Matthysse et al. Physiol. Plant Pathol. 20: 27–33, 1982.*
Ciavatta et al. Am. Soc. Plant Biol., Poster, Abs. #178, 2000.*
Lin et al. Plant Physiol. 116: 1603, 1998.*
Davidonis, et al., "Plant Regeneration From Callus Tissue of *Gossypium hirsutum* L.," *Plant Science Letters* 32:89–93 (1983).
Price, et al., "Somatic Embryogenesis in Suspension Cultures of *Gossypium klotzschianum* Anderss," *Planta* 145, 305–307 (1979).
Shoemaker, et al., "Characterization of somatic embryogenesis and plant regeneration in cotton (*Gossypium hirsutum* L.)," *Plant Cell Reports* 3:178–181.
Finer, et al., "Initiation of callus and somatic Embryos from explants of mature cotton (*Gossypium klotzschianum* Anderss)," *Plant Cell Reports* 3:41–43 (1984).
Mitten, Donna H. "Somatic Embryogenesis in *Gossypium hirsutum* L.," pp. 57–58 (1985).

(List continued on next page.)

Primary Examiner—David T. Fox
(74) Attorney, Agent, or Firm—Saliwanchik, Lloyd & Saliwanchik

(57) ABSTRACT

A method for producing transformed cotton plants. The method comprising providing cotton explants, incubating the cotton explant in the presence of a vector comprising a selectable marker to produce treated explants, growing the treated explants to produce callus and selecting transformed callus.

101 Claims, 29 Drawing Sheets

OTHER PUBLICATIONS

Rangan, et al., "Somatic Embryogenesis in Tissue Cultures of *Gossypium hirsutum* L.," Phytogen, 256:65.

Gawel, et al., "Genetic control of somatic embryogenesis in cotton petiole callus cultures," *Euphytica* 49:249–253 (1990).

Trolinder, et al., "Genotype specificity of the somatic embryogenesis response in cotton," *Plant Cell Reports* 8:133–136 (1989).

Umbeck, et al., Genetically Transformed Cotton (*Gossypium hirsutum* L.), *Bio/Technology* 5(3) :263–266 (1987).

Smith, et al., Defined Conditions for the Initiation and Growth of Cotton Callus in Vitro I. *Gossypium arboreum*, In Vitro, 329, vol. 13 (1977).

Gawel, et al., Somatic embryogenesis from leaf and petiole callus cultures of *Gossypium hirsutum* L., *Plant Cell Reports* 5(6) :457–459 (1986).

Trolinder, et al., "Agriculture, Forestry and Wildlife," *Dissertations Abstracts International* 47 (6) :2250B–2251B (1986).

Ryan, et al., Abstract 117559n, *Chemical Abstracts* 96, 1982.

Chemistry & Industry, No. 7, Apr. 7, 1986, p. 218.

Firoozabady, et al., "Transformation of cotton (*Gossypium hirsutum* L.) by *Agrobacterium tumefaciens* and regeneration of transgenic plants," *Plant Molecular Biology*, 10(2) : 105–116 (1987).

Trolinder, et al., "Somatic Embryogenesis in Cell Suspension Cultures of *Gossypium hirsutum*," Proceedings of the Beltwide Cotton Production Research Conferences, New Orleans, LA, Jan. 6–11, 1985., p. 46.

Stuart, et al., Abstract 56366, *Biological Abstracts* 78(8) : 6339 (1984).

Trolinder, et al., Abstract 62935z, *Chemical Abstract* 106(9) : 225 (1987).

Trolinder, et al., Abstract 36159a, *Chemical Abstracts* 107 (5) :369, (1987).

De Block, et al., "Expression of foreign genes in regenerated plants and in their progeny," *The EMBO Journal* 3(8) : 1681–1689 (1984).

Becker, et al., Abstract 192666q, *Chemical Abstracts* 98(23) : 168 (1983).

Kit, et al., Abstract 62615w, *Chemical Abstracts* 100(9) :131 (1984).

Alieva, Abstract 117970r, *Chemical Abstracts* 100(15) :327 (1984).

Mace, et al., Abstract 85240w, *Chemical Abstracts* 103(11) :379 (1985).

Khamraev, et al., Abstract 190836f, *Chemical Abstracts* 100(23) :499 (1984).

Sarmina, et al., Abstract 62035k, *Chemical Abstracts* 105(8) :76 (1986).

Khuzhanazarov, et al., Abstract 84740k, *Chemical Abstracts* 100(11) :468 (1984).

Price, et al. Chapter 18 "Cotton," *Handbook of Plant Cell Culture*, vol. 3, Crop Species, pp. 487–510.

Huang, et al., Scientia Agricultura Sinica, 1986, pp. 32–36.

Zhou, et al., "Introduction of Exogenous DNA into Cotton Embryos," Methods in Enzymology 101:433–481 (1983).

Kosuge, et al., *Genetic Engineering of Plants: An Agricultural Perspective*, 1983, contents, pp. 381–435.

Shoemaker, et al., Abstract 86768, *Biological Abstracts* 82(9) (1986).

Davidonis, et al., Abstract 65175p, *Chemical Abstracts* 100(9) (1984).

Umbeck, et al., Abstract 170182k, *Chemical Abstracts* 106(3) (1987).

Yenofsky, Richard (1990) "A mutant neomycin phosphotransferase II gene reduces the resistance of transformants to antibiotic selection pressure" *Proceedings of the National Academy of Sciences* (PNAS), 9:3435–3439.

Guri, A., Sink, K.C. (1988) "Agrobacterium Transformation of Eggplant" *Journal of Plant Physiology*, 133:52–55.

*Biotechnology of Agricultural Plants* Apr. 15, 1987, pp. 287–299.

*Proc. Natl. Acad. Sci. USA*, 77, 7347–7351 (1974), Chilton et al.

"Genetic Engineering of Inbred Lines of Sunflower," abstract, *VI International Congress of Plant Tissue and Cell Culture* (Aug. 1986) Everett et al.

"Kulturversuche mit isolierten pflanzenzellen", *Mat. KI. Kais. Akad. Wiss. Wien* 111 62 (1902, Haberlandt.

1988 Pl. Molec. Biol. Manual A9:1–3, 14–16, Reynaerts et al.

*Bio/Technology*, 20, 256, (1986), Umbeck.

Phytomorphology, 11: 109–127 (1961), N. S. Ranga Swamy.

Elzen et al., J. Agric. Food Chem. 33(6): 1079–1082) (1985).

Guang–Yu et al., Introduction of exogenous DNA into cotton embryos, Meth. Enzymology 101: 433–481 (1983).

Joshi et al. Protoplasma 125(1–2): 75–85 (1985).

Kuliev et al., Chemical Abstracts 99(1), Abstra. No. 3158n (1982).

Kuliev et al., Chemical Abstracts 99(1), Abstr. No. 3159p (1983)S.

Larkin et al., Theor. Appl. Genet. 60:197–214 (1981).

Thomson, Aust. J. Agric. Res. 23(1): 285–293 (1972).

"Transformation and Regeneration of/Cotton, *Gossypium hirsutum* L.," public poster presentation at the University of California at Davis by E. Firoozabady et al., Aug. 26–28, 1986.

Agracetus, *Agracetus Develops Method to Genetically Engineer Elite Cotton Varieties*, News Release, May 16, 1991.

A Dictionary of Genetic Engineering, 1985, Cambridge Univ. Press, p. 44.

Dictionary of Microbiology and Molecular Biology, 1987, John Wiley & Sons, p. 384.

Glossary of Biotechnology Terms, 1993, Technomic Publishing Co., pp. 59, 26–27, 121.

The Language of Biotechnology, 1988 ACS publisher, p. 217.

Phytogen News Release, Mar. 28, 1983.

"Recent varieties of cotton (G. hirsutum)", *Cotton Et Fibres Tropicales*, 32(1), 1977, 15–34.

"Seeds of change in the outside world", *Chemistry and Industry*, Apr. 7, 1986.

U.S. Dept. Of Agriculture, Crops Research Division, Agricultural Research Service, *Index of Plant Diseases in the United States*, Aug. 1960, p. 298.

Abstract 66080c, *Chemical Abstracts*, 103(9): #66080c (1985), Adang et al.

Bacterial Galls, "Plant Diseases Caused by Bacteria", *Plant Pathology*, Second ed., Academic Press, NY, 1978, pp. 483–488, Agrious.

*Appl. Environ. Microbiol.* 36:625–626 (1978), Ang et al.

"Prospects in Plant Genetic Engineering", *Science*, vol. 219, pp. 671–676 (1983), Barton et al.

"Regeneration of Intact Tobacco Plants Containing Full Length Copies of Genetically Engineered T–DNA and Transmission of T–DNA to R1 Progeny", *Cell*, vol. 32, No. 4, Apr. 1983, pp. 1033–1043, Barton et al.

"The Effects of Plant Growth Substances on In Vitro Fiber Development From Fertilized Cotton Ovules", Amer. J. Bot. 60(2): 130–139, (1973), Beasley et al.

"In Vitro culture of fertilized cotton ovules", *Bioscience* 21: 906–907, 1971, Beasley.

*Genetic Engineering*, vol. 14, Setlow, J., et al., Plenum Press: New York, pp. 99–124 (1992), Bennetzen et al.

Nucl. Acids. Res., 11: 369–385 (1983), Bevan et al.

"Binary Agrobacterium Vectors for Plant Transformation", *Nucl. Acids. Res.*, 12: 8711–8721 (1984)., Bevan.

*Gene* 2: 95–113 (1977), Bolivar et al.

"Alleviation of In Vitro Organogenic Recalcitrance in Sugarbeet," In Vitro , vol. 21, No. 3, Part II (Mar. 1985) Bornman.

*Anal. Biochem.* 72: 248 (1976), Bradford.

*Expression of a bacterial gene in plants by using a viral vector*, Nature, vol. 310, Aug. 9, 1984, pp. 511–514, Brisson et al.

"The Mob and ori T Mobilization Functions of a Bacterial Plasmid Promote its Transfer to Plants", Nature, 328, 1987, 172–175, Bucchanan–Wollaston et al.

"The role of tissue culture in the study of crown–gall tumorigenesis", *Tissue Culture Methods for Plant Pathologists*, Ingram, et al. eds. pp. 203–208 (1980), Butcher et al.

1983, "Introduction of Genetic Material into Plant Cells", *Science* 222:815–82, Caplan et al.

"Potential of Endophytic Bacteria For Biological Control of Fusarium Wilt of Cotton", Joint Meeting of the American Phytopathological Society and the Society of Nematologists on Plant Pathology Beyond 2000, Nashville, Tennessee, USA, Nov. 6–10, 1993, *Phytopathology* vol. 83(12), p. 1404, A647 (1993), Chen et al.

"A Vector for Introducing New Genes into Plants", *Scientific Am.*, Jun. 1983, vol. 248, pp. 51–59, Chilton.

*Methods in Enzymology* 118:742–766 (1986), Clark et al.

*Science* 221: 370–371, 1983, Comai et al.

"Expression in plants of a mutant aroA gene from *Salmonella typhimurium* confers tolerance to glyphosate", Nature, vol. 317, Oct. 24, 1985, pp. 741–744, Comai et al.

*Nucleic Acids Research*, vol. 9, 6735–6747 (1981), Covey et al.

1986 (Feb.) Mol. Gen. Genet. 202:179–185, Crossway et al.

"In vitro culture of callus tissues and cell suspensions from okra (*Hibiscus esculentus L.* ) and cotton (*Gossypium hirsutum L.* )", In vitro 9 395–398 (1974), Davis et al.

"Mini–Ti: A New Vector Strategy for Plant Genetic Engineering", *Bio/Technology*, May 1983, pp. 262–269, De Framond et al.

"Efficient Transfer of a Glyphosate Tolerance Gene into Tomato Using a Binary *Agrobacterium Tumefaciens* Vector", *Bio/Technology*, vol. 5, Jul. 1987, p. 726–730, Fillatti et al.

Mol Gen. Genet. 206: 192–199, 1987, Fillatti et al.

"Stimulation of Somatic Embryogenesis in Cotton", TCA Report, vol. 17, No. 5, Sep.–Oct. 1983, pp. 8, 17 [Dept. of Soil and Crop Science, Texas A&M], Finer et al.

Plant regeneration from somatic embyrogenic suspension cultures of cotton (*Gossypium hirsutum L.*) 1988, Finer. Abstract 888575, Chemical Abstracts 108(11):153 (1988), Firoozabady et al.

"Transformation and regeneration of cotton", Tailoring Gene for Crop Improvements: An Agricultural Perspective, UC Davis, pp. 24 (1986), Firoozabady et al.

"Insect Tolerant Transgenic Tomato Plants", Bio/Technology, vol. 5, 807–813, Aug. 1987, Fischhoff et al.

"Expression of bacterial genes in plant cells", *Proc. Natl. Acad. Sci. USA*, vol. 80, pp. 4803–4807, Aug. 1983, Fraley et al.

"Use of a Chimeric Gene to Confer Antibiotic Resistance to Plant Cells", Miami Winter Symposium, Advances in Gene Technology: Molecular Genetics of Plants and Animals, 1983, vol. 20, pp. 211–221, Fraley et al.

"Nutrient Requirements of Suspension Cultures of Soybean Root Cells", *Experimental Cell Research* 50, pp. 151–158 (1968), Gamborg et al.

"Calgene Expresses Recombinant Gene for Herbicide Tolerance", *Genetic Engineering News*, vol. 5, No. 4, Apr. 1985, Gebhart.

"Recombinant Genomes Which Express Chloramphenicol Acetyltransferase in Mammalian Cells", *Molecular and Cellular Biology* 2(9): 1044–1051, Sep. 1982, Gorman et al.

*Gene*, 25: 179–188 (1983), Gritz et al.

"Study of F1 hybrids derived from interspecific crosses between two varieties of Gossypium hirsutum and one variety of Gossypium barbadense", Cotton Et Fibres Tropicales, 40(4), 169–186, (1985) Guibordeau et al.

"Expression of chimaeric genes transferred into plant cells using a Ti–plasmid–derived vector", Nature 303(19): 209–213 (1983), Herrera–Estrella et al.

1988 Bio/Technology 6:915–922, Hinchee et al.

"A Binary Plant Vector Strategy Based on Separation of vir– and T–region of the Agrobacterium tumefaciens Ti–plasmid", Nature 303:170–180, 1983, Hoekema et al.

"The Use of the Agrobacterium tumefaciens Ti Plasmid As a Vector For The Genetic Engineering of Plant Cells", *Innovations in Biotechnology*, vol. 20, pp. 425–433 (1984), Hoekema et al.

"Cauliflower Mosaic Virus on Its way to Becoming a Useful Plant Vector", *Gene Cloning in Organisms Other Than E. Coli*, Springer–Verlag, Berlin Heidelberg New York, 193–236 (1982), Hohn.

"Agrobacterium–Mediated Gene Transfer to Plants: Engineering Tolerance to Glyphosate", *Iowa State Journal of Research*, vol. 62, No. 4, May 1988, pp. 487–502, Horsch et al.

"Inheritance of Functional Foreign Genes in Plants", *Science*, vol. 223, pp. 496–498, Feb. 3, 1984, Horsch et al.

A Simple and General Method for Transferring Genes into Plants, *Science*, Mar. 3, 1985, pp. 1229–1231, Horsch et al.

"Callus induction by (2–chlorethyl) phosphoric (CPA) acid in cultured cotton ovules", *Physiol. Plant* 36 150–153 (1976), Hsu et al.

"Regeneration and Transformation in Cultivated Cotton Gossypium Hirsutum", Abstract #P–01–184, First International Congress of Plant Molecular Biology, Savannah GA, (Oct. 1985), Hughes et al.

"Growth and Survival of *Heliothis virescens* (Lepidoptera: Noctuidae) on Transgenic Cotton Containing a Truncated Form of the Delta Endotoxin Gene from *Bacillus thuringiensis*", *Journal of Economic Entomology*, vol. 86 (No. 1): pp. 181–185 (1993), Jenkins et al.

"A Molecular Demonstration of the Introduction into Cotton Embryos of Exogenous DNA", Acta Biochimica et Biophysica Sinica, 16(3), 325–327 (May 1984), Jian [sic. Weng] et al.

"Transformed Callus Does Not Necessarily Regenerate Transformed Shoots", Plant Cell Reports (1988), vol. 7, pp. 285–287, Jordan et al.

"Transfer of Fusarium Wilt Resistance Between Cotton Cutivars Via Exogenous DNA Introduction", Scientia Agricultura Sinica, 3, 1986, 32–36, Junqi et al.

"The influence of a strong reducing agent upon initiation of callus from the germinating seedlings of Gossypium barbadense", Physiol. Plant 40 98–100 (1977), Katterman et al.

1977 McGraw–Hill Encyclopedia of Food Agric. & Nutrition, pp. 494–496, Lapedes.

"Advances in Gene Technology for Plants and Animals", BioTechnology, Apr. 1983, pp. 169–171, Ledeboer et al.

"Organic Growth Factor Requirements of Tobacco Tissue Cultures", Physiologia Plantarum, 18: 100–127 (1965), Linsmaier et al.

"Transformation of Elite Cotton Cultivars in Particle Bombardment of Meristems", Bio/Technology, 11:596–598 (1993)McCabe et al.

"Leaf Disc Transformation of Cultivated Tomato (L.E. Sculentum) using Agrobacterium tumefaciens," Plant Cell Reports 5:81–84 (1986) McCormick.

"A Revised Medium for Rapid Growth and Bio Assays with Tobacco Tissue Cultures", Physiologia Plantarum, vol. 15, pp. 473–497 (1962), Murashige et al.

Nature 313: 810–812, 1985, Odell et al.

J. Mol. Biol. 147: 217–226 (1981), Oka et al.

Gene, 14, 33–50 (1981), Ooms et al.

Plasmid 7: 15–29, 1982, Ooms et al.

"Direct gene transfer to plants", EMBO Journal, 3: 2717–2722 (1984), Paszkowski et al.

"Gene Transfer to Plants: Assessment of Published Approaches and Results", Annu. Rev. Plant Physiol. Plant Mol. Biol., 1991, 42: 205–225, Potrykus.

"Callus cultures of six species of cotton ( Gossypium L.) on defined media", Pl. Sci. Lett. 8 115–119 (1977), Price et al.

Handbook of Plant Cell Culture, vol. 3, Macmillan Publishing Co., New York, pp. 499 and 503 (1984), Price et al.

"Tissue culture of Gossypium species and its potential in cotton genetics and crop improvement", Beltwide Cotton Production Research Conference Proc. pp. 51–55 (1977), Price et al.

"Establishment of Tissue Cultures of Cotton", Plant Sci. Lett. 7 163–169 (1976), Rani et al.

"Untersuchungen uber die morphogenese an Gewebekulturen", Ber. dt. Bot. Ges. 71 15 (1965), Reinert.

"A new sensitive method for qualitative and quantitative assay of neomycin phosphotransferase in crude cell extracts", Gene, 30, pp. 211–217 (1984), Reiss et al.

"Somatic Embryogenesis in Two Strains of Gossypium hirsutum", Ann. Mtg. of the Amer. Soc. of Agronomy, Nov. 25–30, Las Vegas, NV, p. 85 (1984), Robacker et al.

Gene 53: 153–161, 1987, Rothstein et al.

A sensitive and simple paper chromatographic procedure for Detecting neomycin phosphotransferase II (NPT II) gene expression, 1990 Plant Molecular Biology 14:873–876, Roy et al.

"Gene Transfer Strategies in Plants", Biotech Adv.: vol. 10, pp. 393–412 (1992), Sawahel et al.

1983, "The Ti Plasmids as Natural and as Practical Gene Vectors for Plants", Bio/Technology (Apr. Issue) pp. 175–180, Schell et al.

"Ti Plasmids as Experimental Gene Vectors for Plants", 15th Miami Winter Symposium, Advances in Gene Technology: Molecular Genetics of Plants and Animals, 1983, vol. 20, pp. 191–209, Schell et al.

"Medium and technique for induction and growth of monocotyledonous and dicotyledonous plant cell cultures", Can. J. Bot. 50: 199–204 (1972), Schenk et al.

"The use of Nuclear–Encoded Sequences to Direct the Light Regulated Synthesis and Transport of a Foreign Protein into Plant Chloroplasts," The EMBO Journal, vol. 4, No. 1, pp 25–32 (1985) Schreier, et al.

Gene Transfer System for Potato, HortScience vol. 21, No. 5, pp. 1199–1201, Oct. 1986, Shahin et al.

Transformation of Cultivated Alfalfa Using Disarmed Agrobacterium Tumefaciens ,Crop Science, vol. 26, Nov.–Dec. 1986, pp. 1235–1239, Shahin et al.

Molecular Genetics of the Bacterial–Plant Interaction, A Puhler, ed., Springer Verlag, Berlin, Seiten 98–106 (1983), Simon.

"Chemical regulation of growth and organ formation in plant tissues cultured in vitro" Symp. Soc. Exp. Biol. 11 18–130 (1958), Skoog et al.

"Genetic manipulation of plants: from tools to agronomical applications", Sci. Prog., Oxf. (1989) vol. 73, 147–168, Steinbiss et al.

"Growth and organized development of cultured cells/II. Organization in cultures grown from freely suspended cells", Am. J. Bot. 45 705–708 (1965), Steward et al.

"In–ovulo Embryo Culture and Seedling Development of Cotton (Gossypium hirsutum, L.)", Planta, vol. 137, pp. 113–117 (1977), Stewart et al.

"Practical Technology in Mass Production of Cloned Plant", CMC Co., Ltd., (1985) p. 38–47, Takayama.

Transformation of Several Species of Higher Plants by Agrobacterium Rhizogens; Sexual Transmission of the Transformed Genotype and Phenotype, Cell, vol. 37, 959–967, Jun. 1984, Tepfer.

1985 (Dec.), "Somatic Embryogenesis and Plant Regeneration in Gossypium hirsutum L.", Dissertation in Biology, Texas Tech. Univ., Lubbock, TX, Trolinder.

"Somatic Embryogenesis in Cell Suspension Cultures of Gossypium hirsutum", Proceedings of the Beltwide Cotton Production Research Conferences, New Orleans, LA, Jan. 6–11, 1985, p. 46, Trolinder et al.

"Transformation of Cucumber (Cucumis sativus L.) Plants with Agrobacterium Rhizogenes," Theor. Appl. Genet 73: 11–15 (1986) Trulson et al.

"Inheritance and Expression of Genes for Kanamycin and Chloroamphenicol Resistance in Transgenic Cotton Plants", Crop Science, vol. 29, No. 1 (1989), pp. 196–201, Umbeck et al.

"Transgenic plants protected from insect attack", Nature, vol. 328, Jul. 2, 1987, p. 33–37, Vaeck et al.

1985. Plant Mol. Biol. 5:103–108, Waldon et al.

Nov. 1988, Trends in Biotechnology (TIBTECH), 6:265–266 (1988), Widholm.

"Short Direct Repeats Flank the T–DNA ona Nopaline TI Plasmid", Proc. Natl. Acad. Sci. USA 79: 6322–6326 (1982), Yadav et al.

Gene 33: 103–119, 1985, Yanisch–Perron et al.

Chapter 19. "Genetic Manipulation of the Ovule After Pollination", Experimental manipulation of ovule tissues, Chapman et al. (Eds), Longman, NY, pp. 240–250 (1985), Zhou.

"Exogenous DNA Caused Phenotypic Variation in Cotton", *J. Cell Biochem.* Suppl. 7B, p. 250) 1983, Zhou et al.

*Methods in Enzymology*, 100 468–500 (1983), Zoller et al.

"Crown Gall Bacteria (Agrobacterium radiobacter var. tumefaciens) on Cotton Roots in Israel", *Plant Disease* 66(12): 1200–1201 (1982), Zutra et al.

* cited by examiner

TRANSFORMATION OF COTTON PLANTS

RELATED APPLICATIONS

This application is a divisional and continuation in part of Ser. No. 07/680,048 filed Mar. 29, 1991, now U.S. Pat. No. 5,244,802 which was a continuation of Ser. No. 07/122,200 filed Nov. 18, 1987, now abandoned, both of which are incorporated herein by reference.

FIELD OF THE INVENTION

This invention relates to the production of new strains of cotton.

BACKGROUND OF THE INVENTION

This invention is directed to plant regeneration and transformation of cotton, particularly cotton of the species *Gossypium hirsutum L.*

In recent years many tissues of diverse origin from plants belonging to different taxonomic groups have been established as in vitro tissue culture. Some of the factors controlling growth and differentiation of such cultures have also been determined. The establishment of subtle interactions among the different groups of plant hormones, and plant growth regulators operating either directly or indirectly, alone or in synergistic combination, have given to some degree an insight into certain interrelationships that may exist among cells, tissues and organs. The information is however by no means complete.

For some time it has been known that plant cell cultures can be maintained in a non-differentiating proliferative state indefinitely. It has, however, only been recently found that redifferentiation of tissues, organs or whole plant organisms can be experimentally induced. Since the demonstrations by Skoog et al. ["Chemical regulation of growth and organ formation in plant tissues cultured in vitro" *Symp. Soc. Exp. Biol.* 11 18–130 (1958), incorporated herein by reference] that the relative ratio of a cytokinin to an auxin determines the nature of organogenesis in tobacco pith tissue. Reorganization or regeneration from callus cultures includes the formation of shoot primordia or embryos, both of which ultimately lead to plantlet development in vitro.

The tendency for organogenesis vs. embryogenesis still depends upon the species involved and the presence of certain triggering factors which are chemical and/or physical in nature.

In 1902, Haberlandt ["Kulturversuche mit isolierten pflanzenzellen," *Mat. Kl. Kais. Akad. Wiss. Wien* 111 62, incorporated herein by reference] postulated that plant cells possessed the ability to produce entire plants and predicted that this would someday be demonstrable in cell cultures. In 1965, Reinert ["Untersuchungen uber die morphogenese an Gewebekulturen," *Ber. dt. Bot. Ges.* 71 15] and Steward et al. ["Growth and organized development of cultured cells/II. Organization in cultures grown from freely suspended cells," *Am. J. Bot.* 45 705–708] working independently, confirmed the occurrence of in vitro somatic. embryogenesis. (Both references are incorporated herein by reference.) In experimentally manipulating somatic embryogenesis it is believed that two components of the culture media, an auxin and the nitrogen source, play crucial roles.

It has also been shown that the process of somatic embryogenesis takes place in two stages: first, the induction of cells with embryogenic competence in the presence of a high concentration of auxin; and second, the development of embryonic cell masses into embryos in the absence of or at a low concentration of auxin.

The induction of organogenesis or embryogenesis leads to distinct structural patterns in the callus. Detailed study of several plant species has enabled certain generalizations to be made about the developmental pathways leading to shoot, bud or embryo development.

The application of tissue culture techniques to the regeneration of plants via organogenesis or embryogenesis remains perhaps the most important contribution of basic studies in morphogenesis to commercial application.

Beasley reported the formation of callus in ovule cultures of cotton in 1971 ["In vitro culture of fertilized cotton ovules," *Bioscience* 21 906–907 (1971), incorporated herein by reference]. Later, Hsu et al. ["Callus induction by (2-chlorethyl) phosphoric (CPA) acid in cultured cotton ovules," *Physiol. Plant* 36 150–153 (1976), incorporated herein by reference] observed a stimulation of growth of calli obtained from ovules due to the addition of CPA and gibberellic acid to the medium. Callus cultures from other explants such as (a) leaf [Davis et al. "In vitro culture of callus tissues and cell suspensions from okra (Hibiscus esculentus) and cotton (*Gossypium hirsutum*), "In vitro 9 395–398 (1974), both incorporated herein by reference] (b) hypocotyl [Schenk et al. "Medium and technique for induction and growth of monocotyledonous and dicotyledonous plant cell cultures," *Can. J. Bot.* 50 199–204 (1972), incorporated herein by reference] and (c) cotyledons [Rani et al. "Establishment of Tissue Cultures of Cotton," *Plant Sci. Lett.* 7 163–169 (1976), incorporated herein by reference] have been established for *Gossypium hirsutum* and *G. arboreum*.

Katterman et al. ["The influence of a strong reducing agent upon initiation of callus from the germinating seed lings of *Gossypium barbadense*," *Physiol. Plant* 40 98–101 (1977), incorporated herein by reference] observed that the compact callus from cotyledons of *G. barbadense* formed roots, and in one instance regeneration of a complete plant was also obtained. Smith et al. ["Defined conditions for the initiation and growth of cotton callus in vitro, *Gossypium arboreum*," In vitro 13 329–334 (1977), incorporated herein by reference] determined conditions for initiation and subculture of hypocotyl-derived callus of *G. arboreum*. Subsequently, Price et al. ["Callus cultures of six species of cotton (*Gossypium L*) on defined media," *Pl. Sci. Lett.* 8 115–119 (1977), and "Tissue culture of Gossypium species and its potential in cotton genetics and crop improvement," *Beltwide Cotton Production Research Conference Proc. pp.* 51–55 (1977), of the National Cotton Council, Memphis, each incorporated herein by reference] defined conditions for the initiation and subculture of callus from five species of Gossypium.

One of the common problems in establishing cultures of many plant species is the "browning" of the explant in the culture medium. In cotton, this leaching of polyphenols was overcome by replacing sucrose with glucose, and by transferring the cultures to a fresh medium every 10 days. After 3 or 4 passages on glucose supplemented medium, the browning completely disappeared and the cultures could be transferred back to sucrose-supplemented media. Although difficulties with the induction, browning and maintenance of calli during subcultures have been overcome with certain *Gossypium* species, all attempts to regenerate plants from callus cultures have been either unsuccessful or have involved several time-consuming steps. Davidonis et al. ["Plant Regeneration from Callus Tissue of *Gossypium hirsutum*," L. *Plant Sci. Lett.* 32 89–93 (1983), incorporated herein by reference] reported the eventual formation of embryos two years after the initiation of culture.

Although many growth substances, such as natural phytohormones and synthetic growth regulating compounds have been utilized in tissue culture media to bring about plant regeneration in vitro, no generalization, much less specifics, of the effects of different substances on plant regeneration has been arrived at. Indeed, the same substances, when applied to different plant species, may either inhibit growth, enhance growth, or have no effect whatsoever. Therefore, aside from certain standard procedures, it remains necessarily a difficult task to arrive at a working protocol for plant regeneration for any new species and by many orders of magnitude a more difficult task to achieve plant transformation.

The present invention provides a method for the rapid regeneration of cotton plants from segments excised from seedlings. The method described offers a high degree of repeatability and reliability and it enables genetic transformation of cotton plants.

SUMMARY OF THE INVENTION

The present invention describes a method for producing transformed cotton plants. The method comprises providing cotton explants. The cotton explant is incubated in the presence of a vector comprising a selectable marker to produce treated explants The treated explants are grown to produce callus. The callus is selected for transformed callus.

BRIEF DESCRIPTION OF THE DRAWINGS

FIG. 10 shows somatic embryos developing from the selected antibiotic resistance cells of FIG. 9 on an antibiotic-supplemented medium.

FIG. 11 exemplifies transformed somatic embryos established to have kanamycin resistance and transformed to have resistance to the herbicide glyphosate.

FIG. 12 exemplifies cotton plants obtained by inoculating tissues with Agrobacterium containing a mutant AroA gene and thereafter growing the tissues on a non-selective media.

FIG. 13 shows germinating somatic embryos of variety B1644 obtained from suspension cultures treated with the vector pCIB10/BTA-5, and selected on kanamycin (50 mg/L) or G418 (25 mg/l) supplemented media.

FIG. 14 shows plantlets developed from the embryos of FIG. 13.

FIG. 15 shows a plantlet of the variety Siokra developed from transformed embryos exhibiting a resistance to kanamycin.

Figure 1:
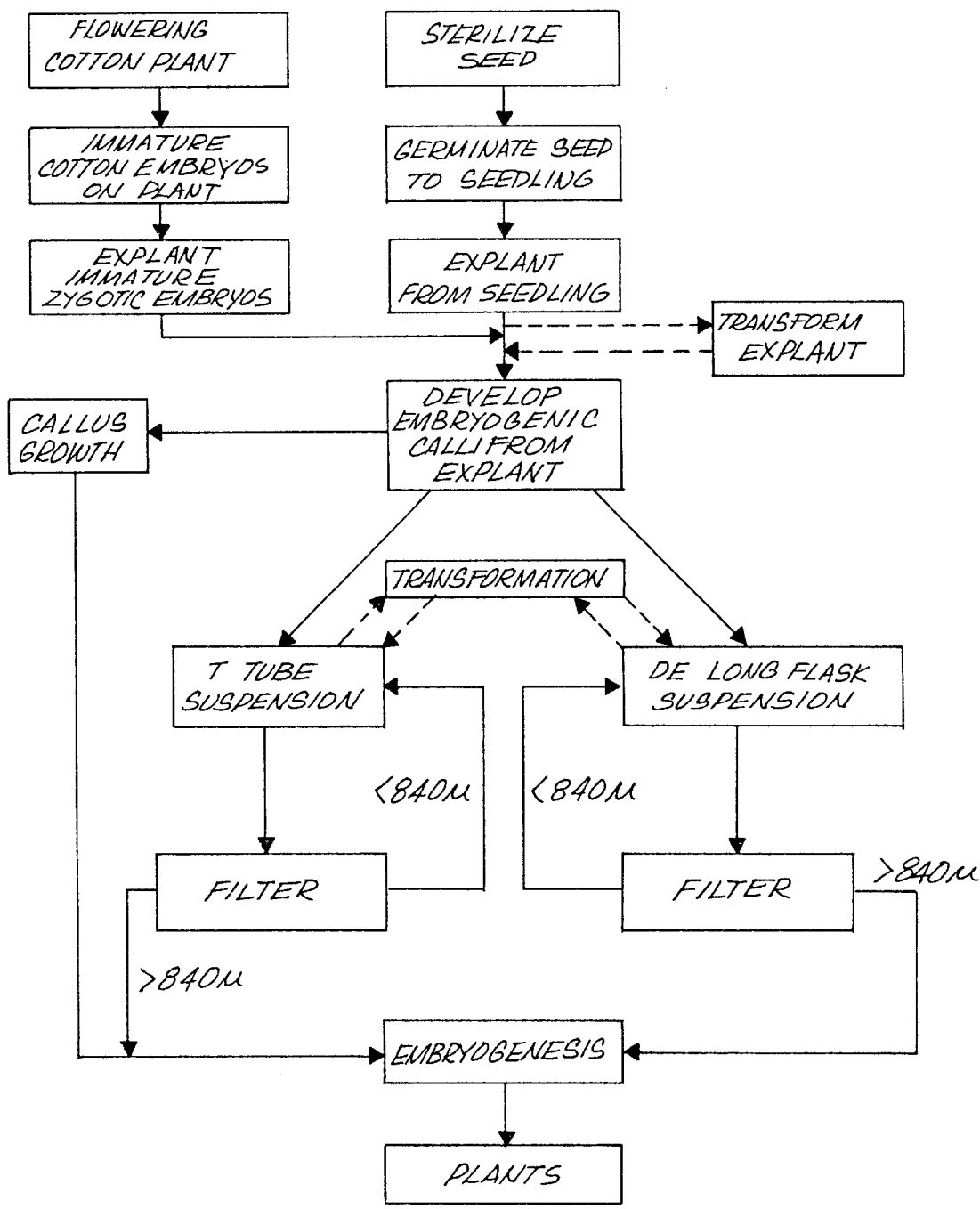
FIG. 1 presents diagrammatically preferred procedures for development of cotton plants from seed by tissue culture techniques with a showing of establishing zones of transformation.

SEED GERMINATION GROWTH MEDIUM COMPOSITION OF MODIFIED WHITE'S STOCK SOLUTION
[Phytomorphology 11 109–127 (1961) incorporated herein by reference]

| Component | Concentration per 1000 ml. | Comments |
|---|---|---|
| $NaH_2PO_4.H_2O$ | 1.65 g | 1000 ml. Label White's A Stock. Use 100 ml/l of final medium. |
| $Ca(NO_3)_2.4H_2O$ | 2.6 g | Dissolve and make up the final volume to 1000 ml. Label White's B Stock. Use 100 ml/l of final medium. |
| $KNO_3$ | 800 mg | |
| KCl | 650 mg | |
| $Na_2MoO_4.2H_2O$ | 2.5 mg | Dissolve and make up the final volume to 100 ml. Label White's C Stock. Use 1.0 ml/l of final medium. |
| $CoCl_2.6H_2O$ | 2.5 mg | |
| $MnSO_4.H_2O$ | 300 mg | |
| $ZnSO_4.7H_2O$ | 50 mg | |
| $CuSO_4.5H_2O$ | 2.5 mg | |
| $H_3BO_3$ | 50 mg | |
| Fe EDTA | | Use 10 ml/l of MSFe EDTA. |
| Organic | | Use 10 ml/l of MS organic. |

CALLUS GROWTH/MAINTENANCE MEDIUM COMPOSITION OF MURASHIGE & SKOOG (MS) STOCK SOLUTIONS
[Physiol. Plant 15 473–497 (1962) incorporated herein by reference]

| Component | Concentration per 1000 ml. of Stock | Comments |
|---|---|---|
| $NH_4NO_3$ | 41.26 g | Dissolve and make up the final volume to 1000 ml. Use 40 ml/l of final medium. |
| $KNO_3$ | 47.50 g | |
| $CaCl_2.2H_2O$ | 11.00 g | |
| $MgSO_4.7H_2O$ | 9.25 g | |
| $KH_2PO_4$ | 4.25 g | |
| KI | 83 mg | Dissolve and make up the final volume to 1000 ml. Label MS-Minor. Use 10 ml/l of final medium. |
| $H_3BO_3$ | 620 mg | |
| $MnSO_4.H_2O$ | 1690 mg | |
| $ZnSO_4.7H_2O$ | 860 mg | |
| $Na_2MoO_4.2H_2O$ | 2.5 mg | |
| $CuSO_4.5H_2O$ | 2.5 mg | |
| $CoCl_2.6H_2O$ | 2.5 mg | |
| Nicotinic acid | 50 mg | Dissolve and make up the final volume to 1000 ml. Label MS-Organic. Freeze in 10 ml aliquots. Use 10 ml/l of final medium. |
| Pyridoxin HCl | 50 mg | |
| Thiamine HCl | 10 mg | |
| Fe EDTA | 2.78 g | Dissolve 2.78 g of $FeSO_4.7H_2O$ in about 200 ml of deionized water. Dissolve 3.73 g of $Na_2$ EDTA.$2H_2O$ (disodium salt of ethylenediaminetetraacetic acid dihydrate) in 200 ml of deionized water in another beaker. Heat the $Na_2$ EDTA solution on a hot plate for about 10 minutes. While constantly stirring, add $FeSO_4$ solution to $Na_2$ EDTA |
| Fe $SO_4.7H_2O$ | 3.73 g | |
| $Na_2$ EDTA.$2H_2O$ | | |

-continued

CALLUS GROWTH/MAINTENANCE MEDIUM COMPOSITION OF MURASHIGE & SKOOG (MS) STOCK SOLUTIONS
[Physiol. Plant 15 473–497 (1962) incorporated herein by reference]

| Component | Concentration per 1000 ml. of Stock | Comments |
|---|---|---|
| | | solution. Cool the solution to room temperature and make up the volume to 1000 ml. Label MS EDTA. Cover bottle with foil and store in refrigerator. Use 10 ml/l of final medium. |
| Thiamine HCl | 50 mg | Dissolve and make up the volume to 500 ml. Label MS - Thiamine. Use 4.0 ml/l of final medium. As if required. |
| Inositol | 10 g | Dissolve and make up the final volume to 1000 ml. Label MS-glycine/inositol. Use 10 ml/l of final medium. |
| Glycine | 0.2 g | |

PLANT GERMINATION MEDIUM COMPOSITION OF BEASLEY AND TING'S STOCK SOLUTIONS
[Am. J. Bot. 60 130–139 (1973) incorporated herein by reference]

| Component | Conc. per 1000 ml. | Comments |
|---|---|---|
| $KH_2PO_4$ | 2.72 g | Dissolve and make up the volume to 100 ml. Label B&T - A Stock. Use 10 ml/l of final medium. |
| $H_3BO_3$ | 61.83 mg | |
| $Na_2MoO_4.2H_2O$ | 2.42 mg | |
| $CaCl_2.2H_2O$ | 4.41 g | Dissolve and make up the volume to 100 ml. Label B&T - B Stock. Use 10 ml/l of final medium. |
| KI | 8.3 mg | |
| $CoCl_2.6H_2O$ | 0.24 mg | |
| $MgSO_4.7H_2O$ | 4.93 g | Dissolve and make up the volume to 100 ml. Label B&T - C Stock. Use 10 ml/l of final medium. |
| $MnSO_4.H_2O$ | 169.02 mg | |
| $ZnSO_4.7H_2O$ | 86.27 mg | |
| $CuSo_4.5H_2O$ | 0.25 mg | |
| $KNO_3$ | 25.275 g | Dissolve and make up the volume to 200 ml. Label B&T - D Stock. Use 40 ml/l of final medium. |
| Nicotinic acid | 4.92 mg | Dissolve and make up the final volume to 100 ml. Label B&T-Organics. Use 10 ml/l of final medium. |
| Pyridoxin HCl | 8.22 mg | |
| Thiamine HCl | 13.49 mg | |
| Fe EDTA | | Use 10 ml/l of MS Fe EDTA. |
| Inositol | | 100 mg/l of final medium. |
| $NH_4NO_3$ (15 $\mu M$) | | 1200.6 mg/l of final medium. |

With any of the above solutions, the following procedure is used to prepare one liter of the medium. There is provided as a base, 200 ml of deionized water and the various stock solutions are added in the amounts stated for 1 liter. For example, if there is to be employed 10 ml of a stock in the final medium, then 10 ml of the stock are added to the 200 ml of the distilled water. To ensure the salts stay in solution, stock solutions are normally added in the order shown in the formulations above. After thoroughly mixing additional deionized water is added to the mixture to bring it to, as required 500 ml, and the mixture adjusted in pH to a value of from about 5.8 to 6.0. The final volume is brought to 1,000 ml and there is normally added tissue culture Agar, or its equivalent to a level of about 0.8% by weight. This is to provide some solidity to solution to reduce flow. The mixture is then autoclaved for about 5 to 20 minutes at a pressure 15–21 lbs/in$^2$ to kill any contaminating organism, and suitably labeled and stored as a sterile medium.

Briefly, cotton seeds are sterilized and germinated on a suitable seed germination medium such as a basal agar medium in the dark for a time sufficient to produce seedlings. The normal period of growth is up to about 4 weeks, typically 7 to 14 days.

Segments of explants are excised from the seedling. It is preferred that the explant come from the hypocotyl or cotyledon. In the alternative, one can equally use immature embryos obtained from the developing fruits of greenhouse or field grown cotton plants as the explant. The explant segments are cultured on a suitable first callus growth medium, preferably a or full Murashige and Skoog (MS) nutrient medium containing glucose. Growth occurs by culturing at a temperature of from about 25 to about 35° C. in a light/dark cycle of about 16 hours of light and above 8 hours of dark. Culturing is the procedure whereby the medium is replaced at periodic intervals as the nutrients are consumed and continued for approximately about 3 to about 4 weeks, or until undifferentiated callus are formed. The callus are transferred to a second callus growth medium, preferably an MS medium supplemented with naphthaleneacetic acid (NAA) and sucrose as the carbon source and cultured for three to four months to produce embryos.

The embryos may then be maintained in the second callus growth medium to maintain an embryo supply or transferred to a plant germination medium such as Beasley and Ting's medium preferably containing casein hydrolysate and source of ammonium cultured for 2 to 3 weeks to produce plantlets.

The plantlets are transferred to soil under high humidity conditions, then transplanted to larger pots in a greenhouse and finally transferred to the field for growth to maturity.

The methods briefly described herein have been successfully employed to induce somatic embryo formation in cotton of the species *Gossypium hirsutum* by tissue and suspension cultures and, ultimately, to obtain mature plants from hypocotyl and cotyledon derived callus cultures of Acala varieties of Gossypium hirsutum including Acala SJ2, Acala SJ4, Acala SJ5, Acala SJ-C1, Acala B1644, Acala B1654-26, Acala B1654-43, Acala B3991, Acala GC356 (plants not obtained), Acala GC510, Acala GAM1, Acala Royale, Acala Maxxa (callus only formed), Acala Prema, Acala B638 (plants not formed), Acala B1810, Acala B2724, Acala B4894, Acala B5002 (plants not formed), non Acala "picker" Siokra, "stripper" variety FC2017, Coker 315, STONEVILLE 506, STONEVILLE 825 (plants not formed), DP50 (callus only formed), DP61 (callus only formed), DP90 (callus only formed), DP77 (callus only formed), DES119 (callus only formed), McN235 (callus only formed), HBX87 (plants not formed), NBX191 (callus only formed), HBX107 (callus only formed), FC 3027, CHEMBRED A1 (callus only formed), CHEMBRED A2 (callus only formed), CHEMBRED A3 (callus only formed), CHEMBRED A4 (callus only formed), CHEMBRED B1 (callus only formed), CHEMBRED B2, CHEMBRED B3 (callus only formed), CHEMBRED C1 (callus only formed), CHEMBRED C2 (callus only formed), CHEMBRED C3 (callus only formed), CHEMBRED C4, PAYMASTER 145 (callus only formed), HS26 (callus only formed), HS46 (callus only formed), SICALA (plants not formed), PIMA S6 (plants not formed) and ORO BLANCO PIMA (plants not formed). Cultures have been transformed to normal plants with novel traits or properties.

The Acala SJ2 was obtained from a the cross AXTE1× NM 2302. The Acala SJ4, SJ5, SJ-C1, B1644, B1654-26, B1654-43, B3991, GC356, GCS10, GAM1 were obtained from the cross C6TE×NM B3080. Acala Royale was obtained from the cross [C6TE×NM B3080]×[AXTE 1-57× TEX E364]. Acala. Maxxa was obtained from the cross [S196×1900-1]×[12302-4×(C6TE×B7378)]. Acala Prema was obtained from the cross [ATE-11×NM49-2]×[C6TE× NM B3080].

More particularly, the procedure involves first the sterilizing of the cotton seeds. Suitable sterilization may be achieved by immersing the seeds in 95ethanol for 2 to 3 minutes, rinsing in sterile water one or more times, then soaking the seeds in a 15% solution of sodium hypochlorite for 15 to 20 minutes, and rinsing several times with sterile water.

The sterilized seeds are then transferred to a first medium, termed a seed germination medium. A seed germination medium is one of normal salt content. A suitable germination medium is a basal agar medium, including White's medium or half-strength MS medium. (One-half ingredient strength). Germination normally occurs in the dark over an about 12 to about 14 day period.

Hypocotyl and/or cotyledons are preferably excised from the germinated seed, subdivided or cut into segments and cultured on a first callus growth medium such as an MS medium supplemented with growth substances. The presently preferred medium is the MS medium supplemented with about 0.4 mg/l thiamine hydrochloride, about 30 g/l glucose, about 2 mg/l NAA, about 1 mg/l kinetin, a common growth regulator, and about 100 mg/l inositol and agar. Thiamine hydrochloride can generally range in concentration from 0.1 to about 0.5 mg/l, glucose about 20 to about 30 g/l, about 1 to about 10 mg/l NAA, about 1 to about 2 mg/l kinetin and about 50 to about 100 mg/l inositol.

The cultures are maintained at a temperature of about 25 to about 35° C., preferably about 30° C. and with a light/dark cycle of about 16 hours of light and about 8 hours of dark. It is preferred to have a light intensity of about 2000 to 4000 lux, more preferably about 3000 to 4000 lux.

The calli formed are periodically subcultured at 3 to 4 week intervals and transferred to a fresh first callus growth medium. In the culturing of the explants, secretions of phenolic compounds from the explants can occur as evidenced by darkening of the cultured medium. In this instance, the medium is changed more regularly. Darkening has been avoided by changing the culture medium every 10 days. Normally, after three to five medium changes, phenolic secretions will disappear. When this occurs, the first callus growth medium can be replaced by fresh callus growth medium containing sucrose or supplemented with sucrose as a carbon source.

After 3 to 4 weeks of culture, active calli develop on the cut surfaces of the explants. The calli are then transferred to a fresh second callus growth maintenance medium which is preferably an MS medium combined with about 1 to about 10 mg/l, preferably about 1 to about 5 mg/l NAA. Cytokinin is employed at a concentration of from 0 to about 1 g/l. A callus growth medium is characterized as a high salt content medium containing as much as 10 times more salt than the seed germination medium. The essential difference between first and second callus growth medium is the carbon source. Glucose is used during period of phenolic secretions. Sucrose is used when secretion have stopped. The balance of the callus growth medium can remain the same or changed.

The calli are transferred in regular intervals to a fresh callus growth medium and, after generally about 5 to 7 passages or until an anthocyanin pigmentation becomes evident in a portion of the calli, which is followed by development of a yellowish-white embryogenic callus.

The embryogenic callus are then selectively subcultured and maintained by regular subculturing. The embryogenic callus contain somatic embryos at various stages of development. Some may have reached the point of development that enables growth into small plantlets. Most, however, require further development. Some may be advanced to germination. Other may be maintained as a source of embryos for future use.

Figure 2:
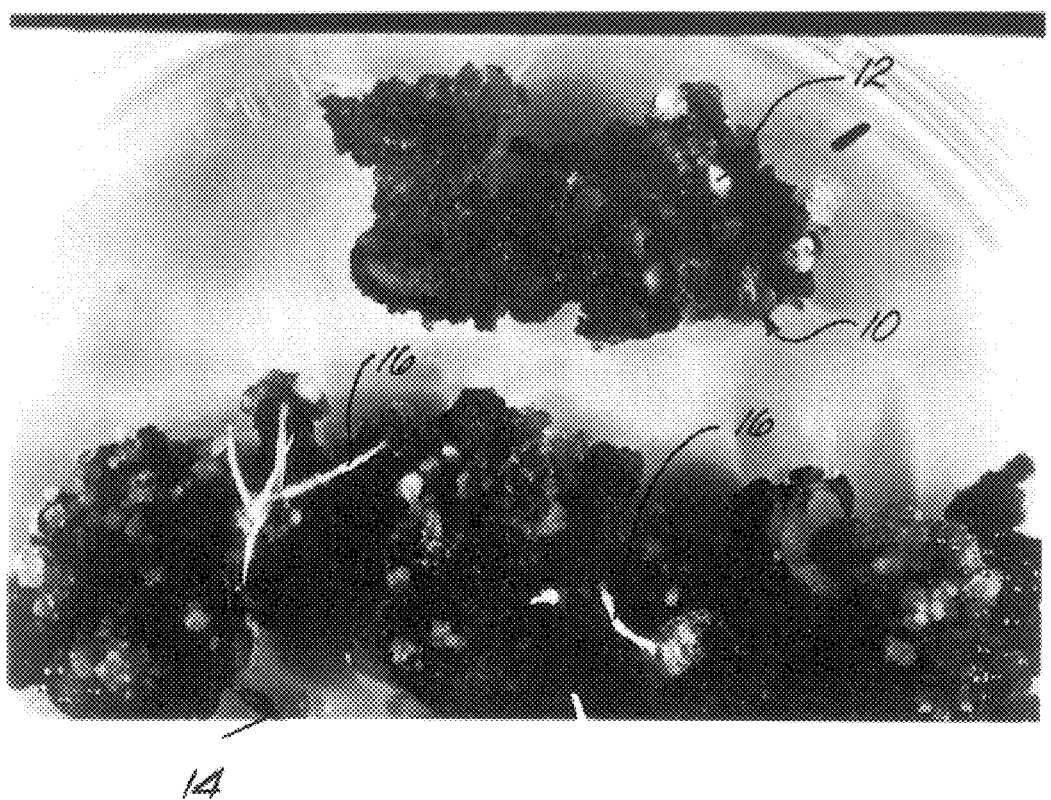
FIG. 2 is a photo illustration of embryogenic callus (10) of cotton with somatic embryos (12) at various stages of development including leaf (14) and root (16).
Figure 3:
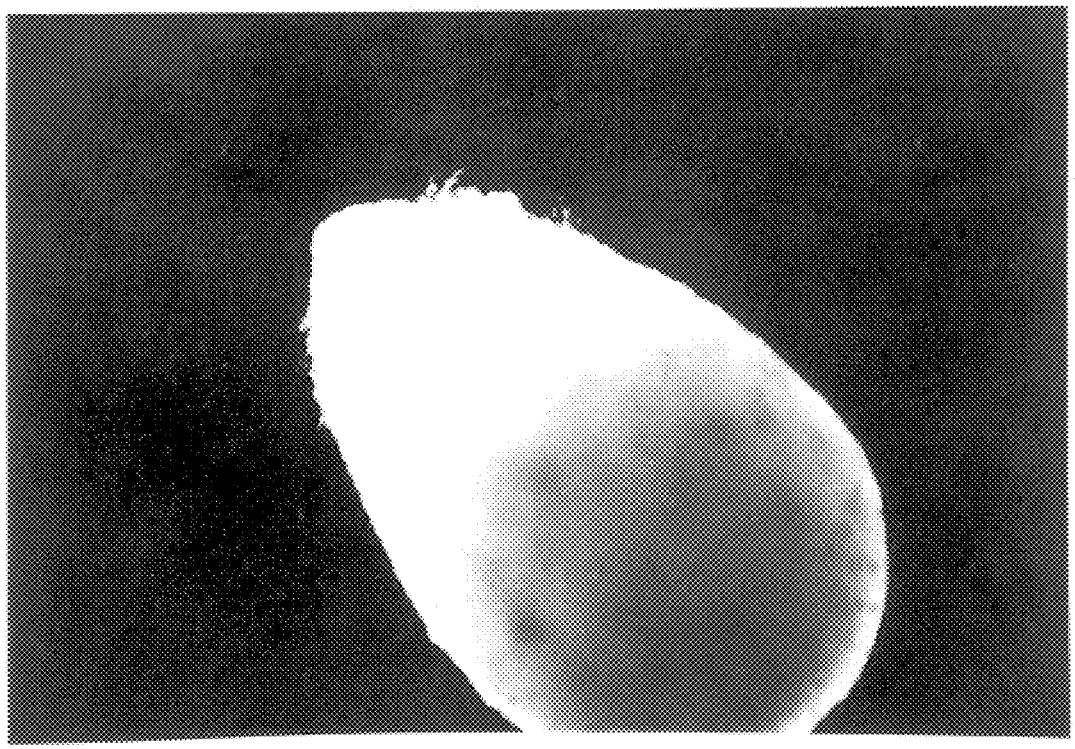
FIG. 3 is a photo illustration of a somatic cotton embryo at a late globular stage isolated to form the embryogenic callus culture as depicted in FIG. 2.

With reference to FIG. 2, there is illustrated this stage of development showing calli of Acala cotton 10 with somatic embryos 12 of differing size with some having emerging leaves 14 and roots 16. FIG. 3 illustrates a somatic embryo isolated at a late globular stage.

Figure 4:
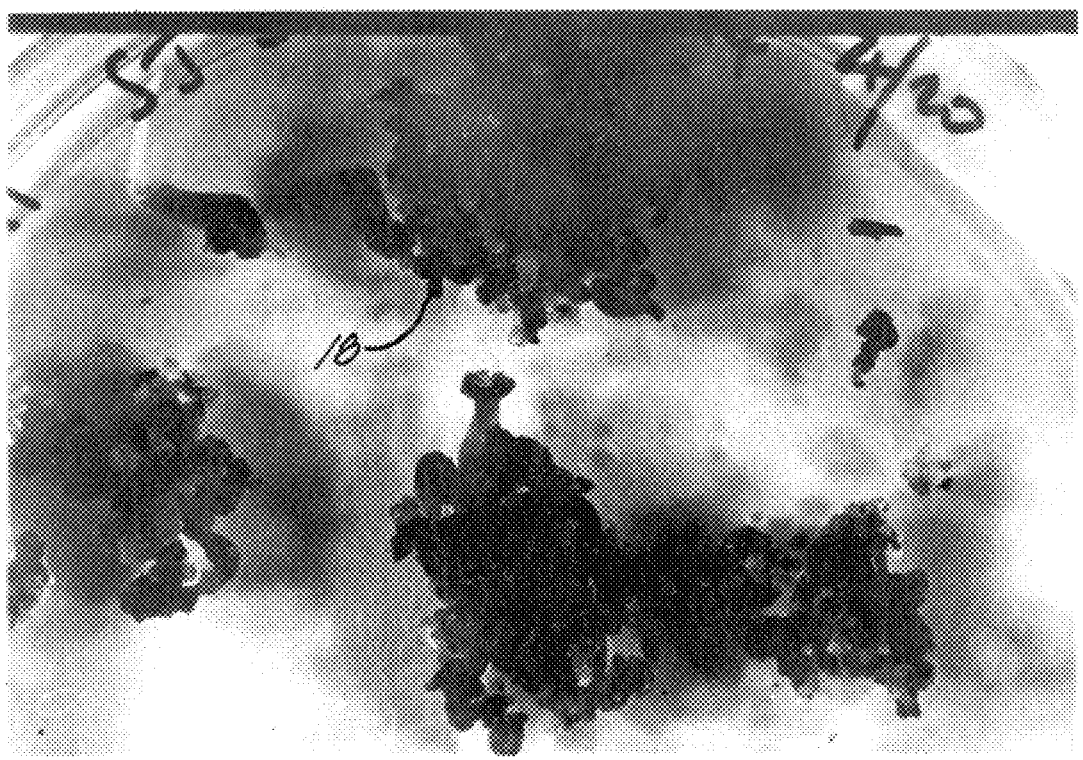
FIG. 4, as with reference to FIG. 2, is a photo illustration of embryos and young plantlets (18) of cotton developing on an embryo germination medium.

With reference to FIG. 4, further development may be achieved by transferring the somatic embryos to a third growth medium termed herein an embryo germination medium, a medium rich in nitrogen usually in the form of ammonia or its equivalent. Suitable media include Beasley and Ting's medium, preferably supplemented with up to about 500 mg/l casein hydrolysate.

Germination occurs from somatic embryos and, within 2 to 3 weeks, a well developed plantlet 18 of up to 6 leaves and good root system is generally formed.

Figure 7:
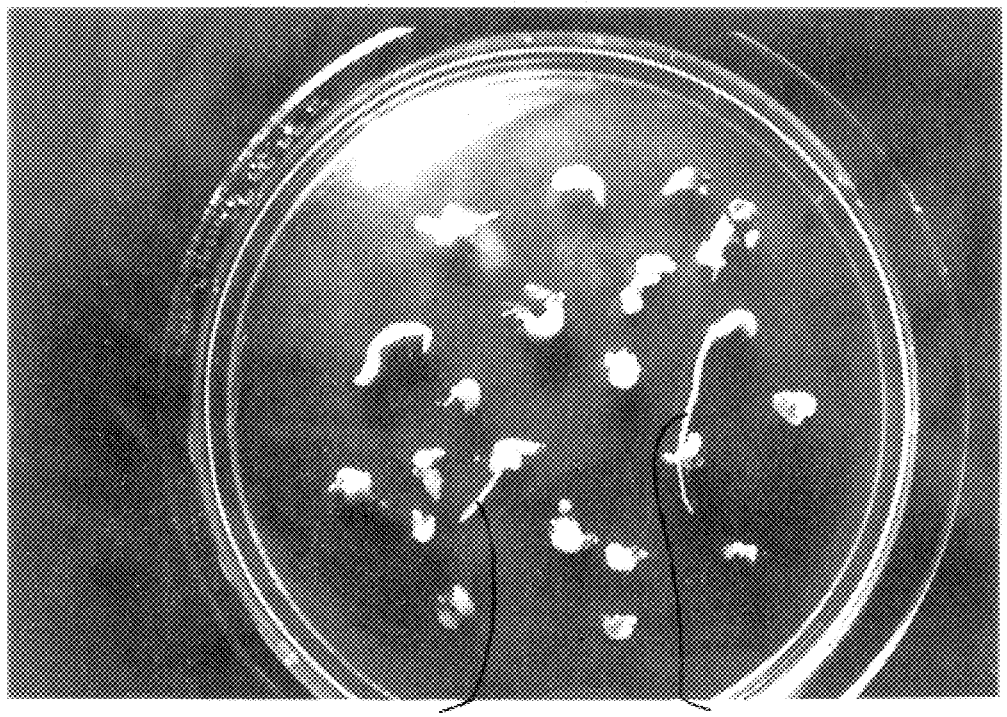
FIG. 7 illustrates germinating embryos obtained from suspension cultures showing emerging leaves (14) and roots (16).
Figure 8:
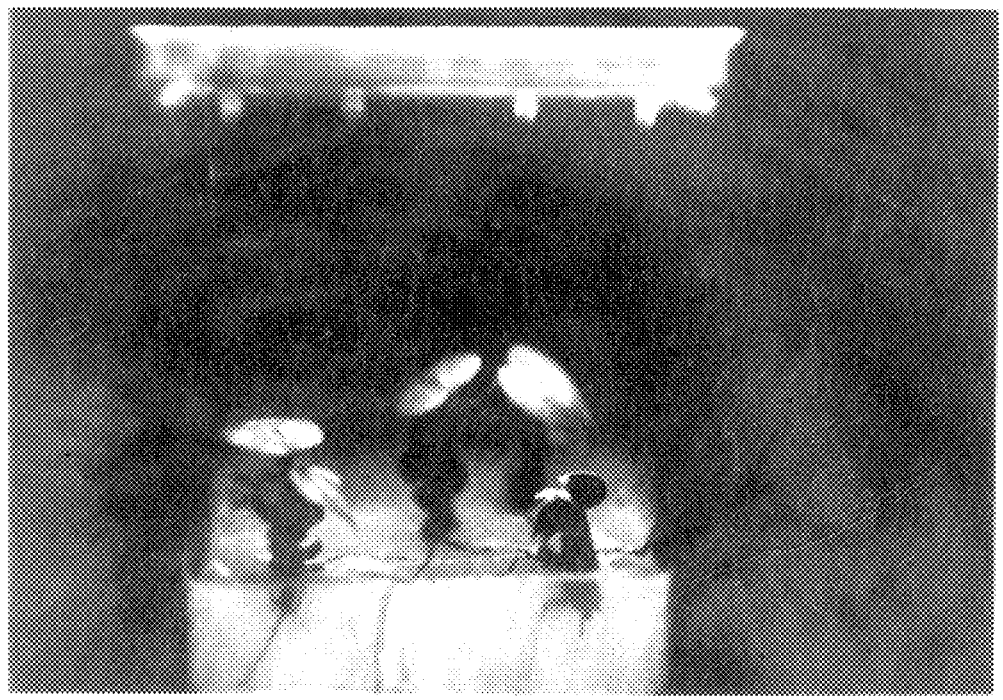
FIG. 8 illustrates the development of plantlets of cotton growing on the embryo germination medium.

At this stage, the plantlets are transferred to soil in small clumps and grown in a standard incubator under conditions of high humidity. Temperature is normally maintained at about 25 to 30° C. (See FIG. 7).

After a period of growth, the small plants are transferred to larger pots in a greenhouse and thereafter transferred to field and grown to maturity. All the regenerated plants are preferably self-pollinated either while growing in the green house or in field conditions and the seeds collected. Seeds are then germinated and 4 to 5 week old seedlings transferred to the field for progeny row trials and other standard plant breeding procedures. Practicing the above procedure produces viable cotton plants from about 35% of the explants in the period of time from about 6 to about 8 months.

Proliferation of Embryogenic Cotton Cells in Suspension Cultures

As an alternative to allowing the growing embryogenic calli to be developed into a plant, the callus may be cut into smaller pieces and further developed using suspension culture techniques.

In this procedure, suspension concentration is normally from about 750 to 1000 mg of callus parts to 8 ml callus growth medium such as the second callus growth medium (MS medium supplemented with NAA), and allowed to grow in suspension. In a preferred embodiment, the suspension of the callus is inserted in T-tubes and placed on a roller drum rotating at about 1.5 rpm under a light regime of about 16 hours of light and about 8 hours of dark. Growth is for about 3 to 4 weeks.

Figure 5:
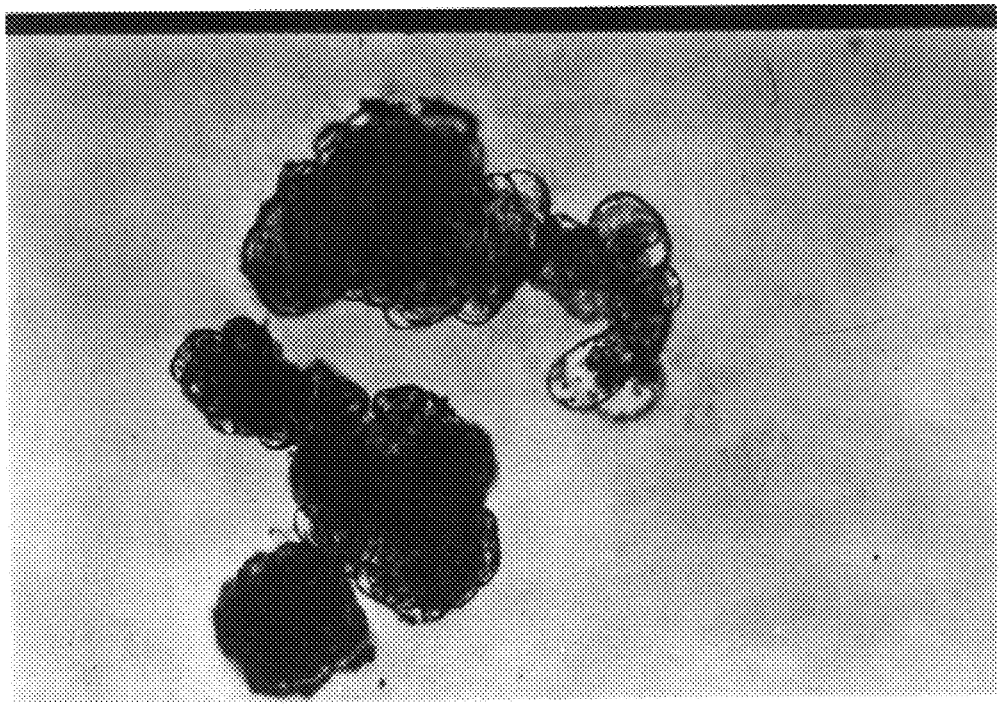
FIG. 5 is a photo illustration of small clumps of embryogenic cells from suspension cultures of cotton.
Figure 6:
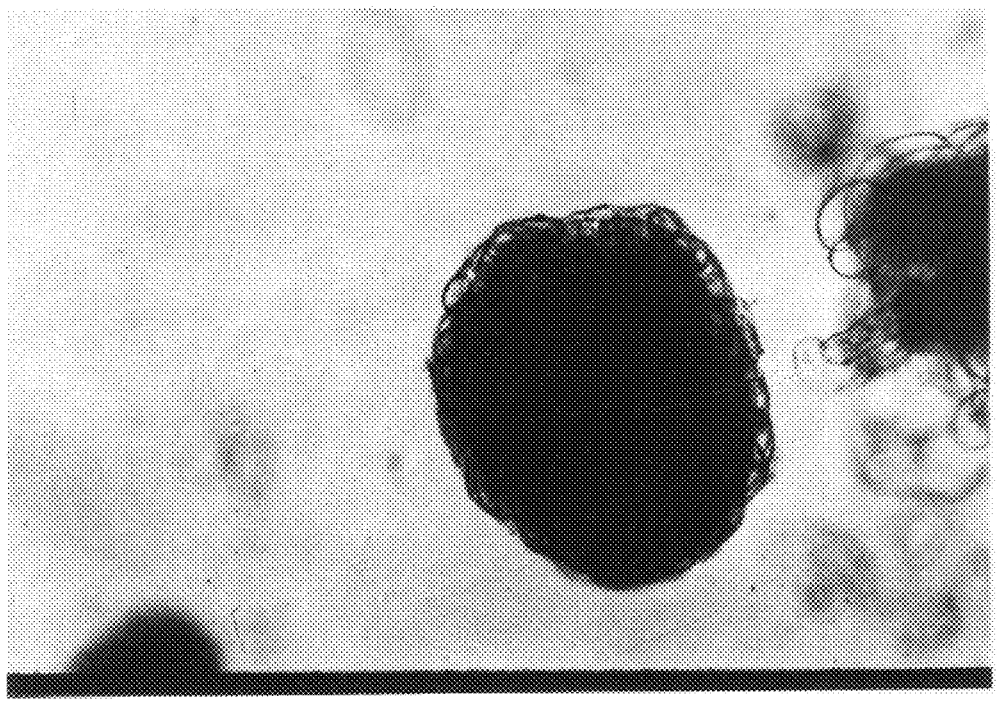
FIG. 6 is a photo illustration of a globular stage embryo from a suspension culture.

After about every 3 to 4 weeks, the suspension is filtered to remove large cell clumps of embryogenic callus depicted in groups in FIG. 5 and as isolated at late globular stages as shown in FIG. 6. The filtrate is returned to a nutrient medium for a 3 to 4 week period of growth. This procedure is repeated over and over with harvesting of large clumps at about 3 to 4 week intervals, at which time the medium is supplanted in whole or in part with fresh callus growth medium. Preferably, about 4 volumes or more of the fresh medium are added to about one volume of residual suspension. It is presently preferred that the filter employed have a mesh size greater than about 600 microns, preferably greater than 800 microns, as it has been observed the cell masses of a particle size less than 600 microns will not develop into plants, whereas cell masses greater than 600 microns and preferably greater than 800 microns have undergone sufficient differentiation so as to become embryogenic and capable of developing into viable plants.

Suspension cultures can also be initiated by transferring of embryogenic calli to a flask, such as a DeLong or Erlenmeyer flask, containing the liquid embryo growth medium in an amount of about 20 ml of MS and NAA at a concentration of 2.0 mg/l. The flask is placed on a gyrotory shaker and is shaken at about 100–110 strokes per minute. After 3 to 4 weeks the suspension is suitable for filtration as described above to remove the large cell clumps for plant development.

More typically, after the third or fourth subculture, the cell suspension from the "T" tube or De Long or Erlenmeyer flask is plated onto agar-solidified MS medium containing NAA (2.0 mg/l) or Beasley & Ting's medium containing casein hydrolysate (500 mg/l) media and a source of nitrogen. Within 3–4 weeks embryogenic calli with developing embryos become visible. Likewise, the larger cell clumps when plated on the above media give rise to embryogenic clumps with developing embryos.

In both suspension growth methods, the MS media is used to promote and/or sustain embryos whereas the germination medium is employed for rapid plant development.

The seedling explants, if desired, can be transformed. In this procedure, cotyledon and/or hypocotyl segments of the sterilized seed can be used. Cotyledons are preferred.

The segments are placed in a medium containing an Agrobacterium vector containing a code (genetic marker) such as resistance to an antibiotic, such as for instance kanamycin for a time sufficient for the vector to transfer the gene to the cells of the explant. Generally, contact times ranging from 1 minute to 24 hours may be used and may be accompanied with intermittent or gentle agitation. The explants are then removed and placed on agar-solidified callus growth medium such as a MS medium supplemented with NAA (2 mg/l) and incubated about 15 to 200 hours at 25 to 35° C., preferably 30° C., on a 16:8 hour light:dark regime.

After incubation, the explants are transferred to the same medium supplemented with the antibiotic cefotaxime preferably in a concentration of 200 mg/l. Cefotaxime is included to prevent any remaining Agrobacterium from proliferating and overgrowing the plant tissues. Alternatively, the explants can be rinsed with MS medium supplemented with NAA (2 mg/l) and incubated an additional 4 to 28 days before rinsing, then incubating the same medium containing cefotaxime. At the end of 4–5 weeks of culture on fresh medium, the developing callus, i.e., primary callus, is separated from the remainder of the primary explant tissue and transferred to MS medium containing NAA (2 mg/l), cefotaxime (200 mg/l) and an antibiotic such as kanamycin sulfate (50 mg/l). Transformed primary callus, identified by virtue of its ability to grow in the presence of the antibiotic (kanamycin), is selected and embryos developed, germinated and plants obtained following the procedure set forth above.

It is also feasible to achieve transformation of a cell suspension. Following a normal subculture growth cycle of 7 to 14 days, usually 7 to 10 days, cells are allowed to settle leaving a supernatant which is removed. The remaining concentrated suspended cells may be centrifuged at 4000×g for 5 minutes and the excess medium is discarded. The concentrated suspension cultures are resuspended in the 8 ml of the same medium which contains the Agrobacterium. The suspension is transferred to "T" tubes and suitably agitated for incubation.

Following about 2 to 24 hours, preferably 3 to 5 hours, of incubation to allow for bacterial attachment and DNA transfer, the suspension is removed and allowed to settle. The supernatant containing the bacteria is discarded and the cells are washed with fresh medium. The suspension may, if desired, be centrifuged for about 5 minutes and the supernatant removed. In either event, the cells are resuspended in the same medium and transferred to a "T" tube or flask and suspension subculture resumed. The object is to minimize the amount of unattached Agrobacterium vector left in the cell suspension.

After about 15 to about 200 hours, typically 15 to about 72 hours, preferably 18 to 20 hours, the suspension is filtered to remove large clumps and washed with fresh liquid medium and allowed to settle. The suspension is resuspended in the fresh liquid medium containing cefotaxime (200 mg/l) plated on a solidified medium in Petri dishes.

Alternatively, the suspension may be resuspended in fresh medium containing cefotaxime and allowed to grow an additional 4 to 28 days prior plating on solidified medium in Petri dishes. Cell concentration is 1 vol. of suspension cells plus 3 vol. of medium with cefotaxime. Kanamycin at 10 to 300 mg/l preferably about 20 to 200 mg/l more preferably about 40 to 80 mg/l is included in the medium for selection of transformed cells expressing the neomycin phosphotransferase (NPT) gene. Cells and embryos proliferating in the selective concentration of kanamycin are further grown as set forth above to mature somatic embryos capable of germinating and regenerating into whole plants according to the procedures described herein.

Figure 9:
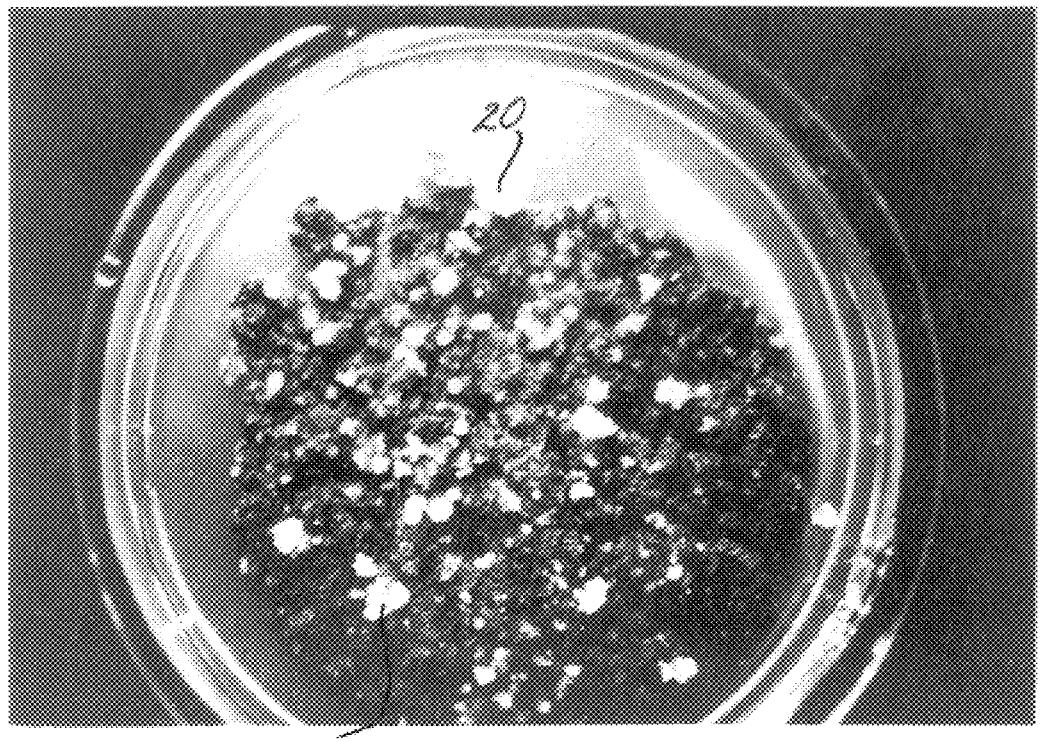
FIGS. 9 to 15 depict the genetic transformation of cotton, with FIG. 9 showing the development of cell colonies (20) from transformed cotton cells containing a gene for kanamycin resistance.
Figure 10:
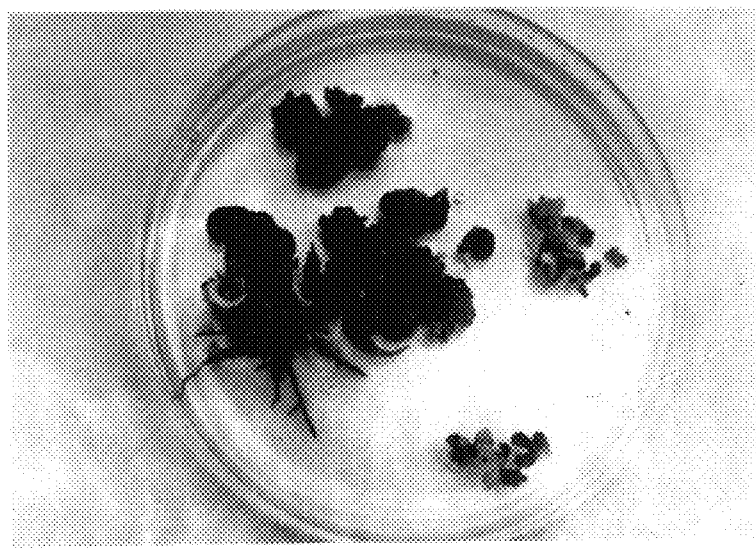
Figure 11:
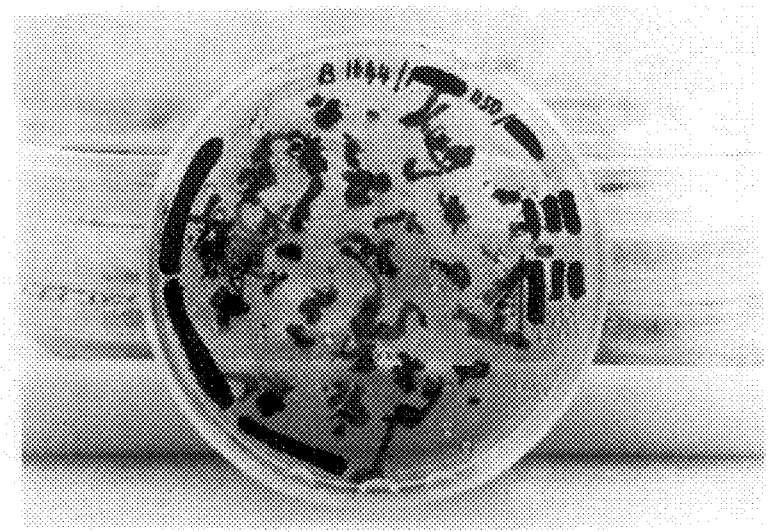
Figure 12:
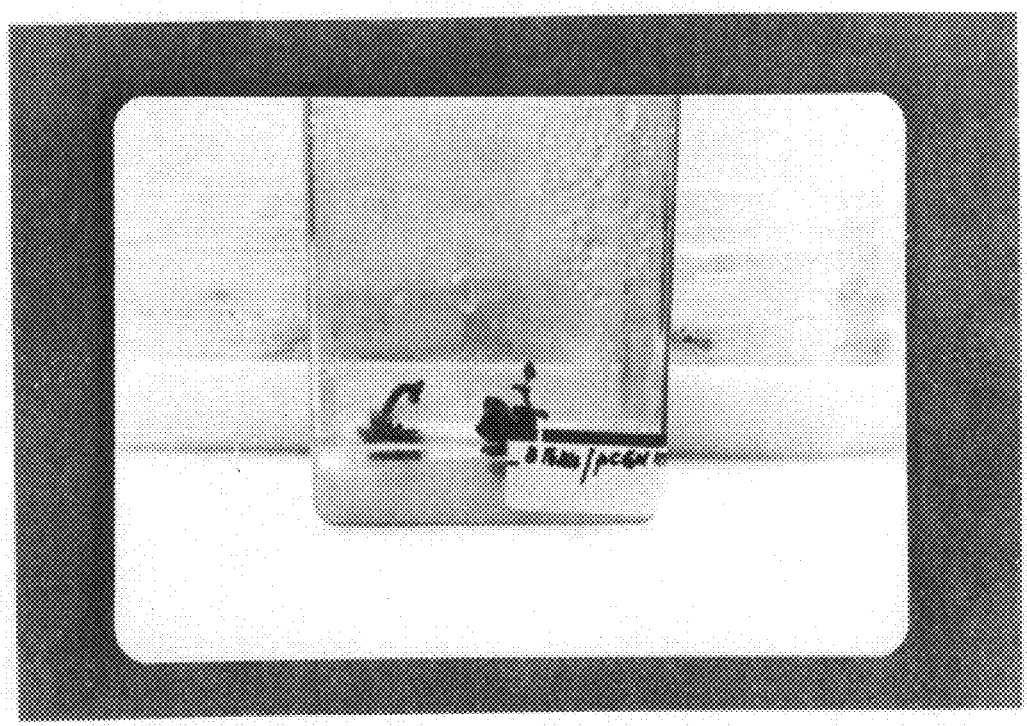
Figure 13:
Figure 14:
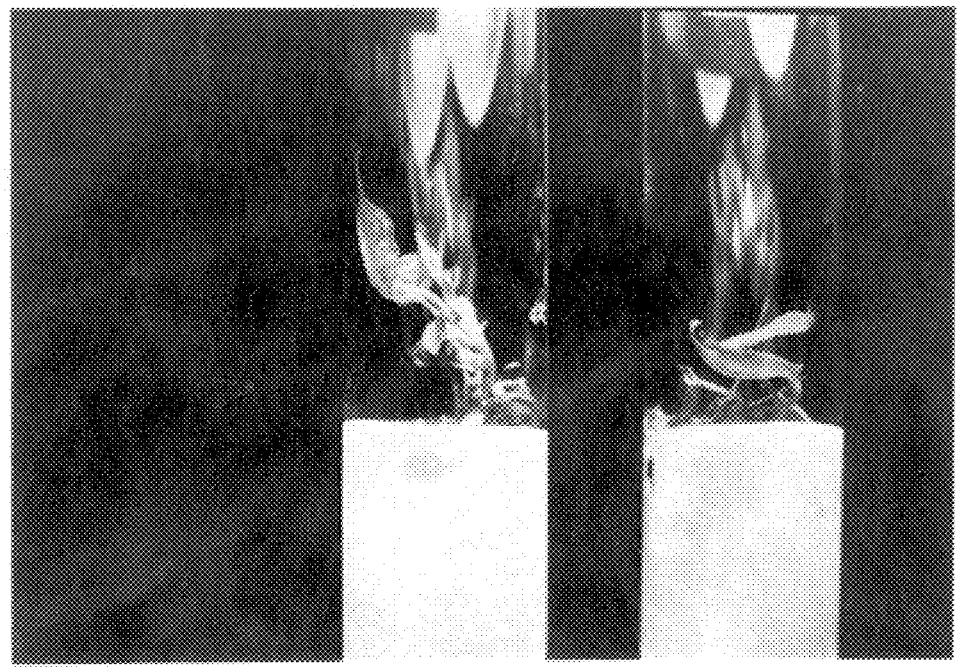
Figure 15:
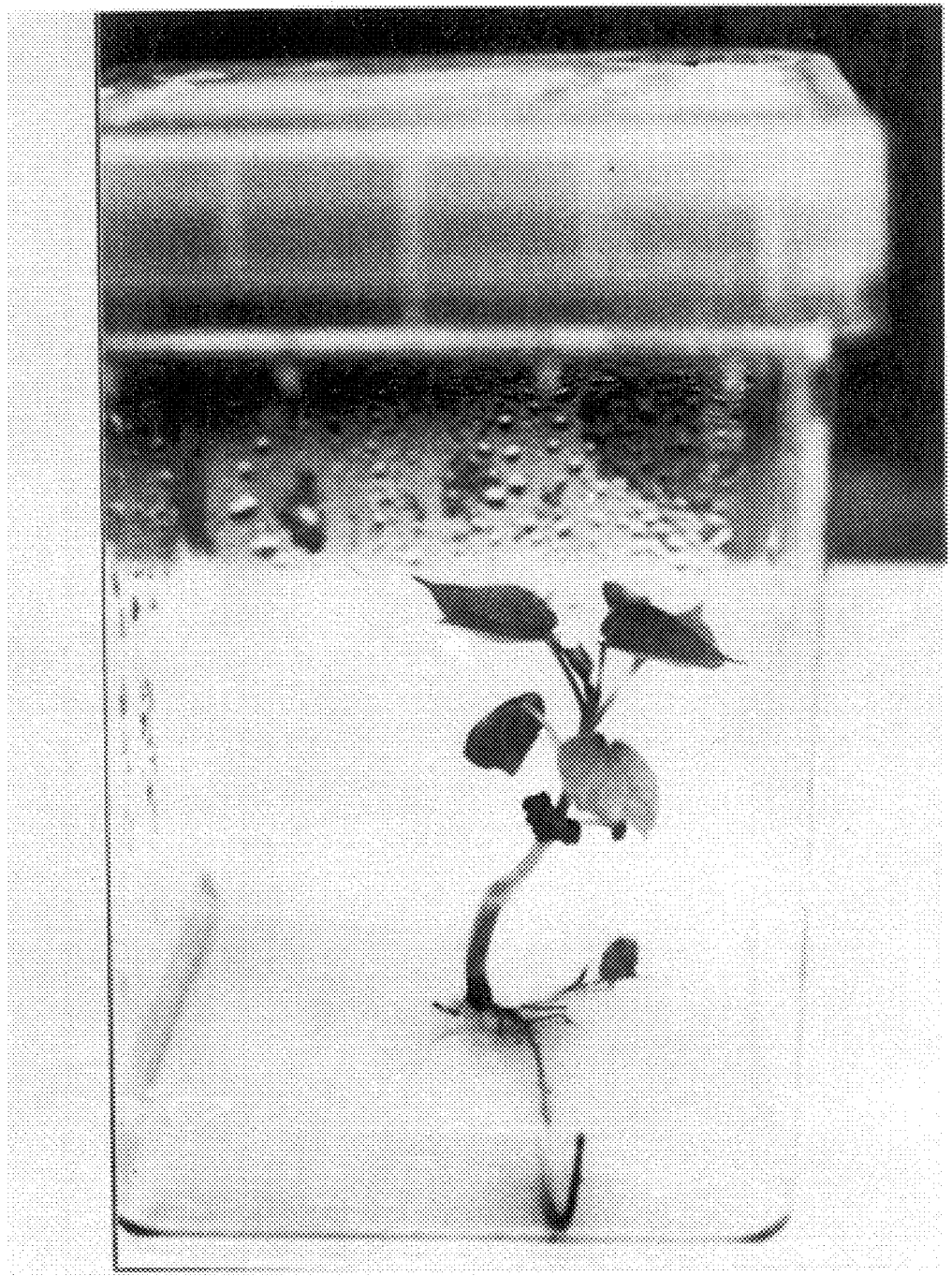

Using the above procedure and with reference to FIG. 9, there is shown variable cell colonies which is consequence of transformation. There exists cotton cells 20 exhibiting resistance to the antibiotic kanamycin. With reference to FIG. 10, transformed calli are shown developing into somatic embryos on an antibiotic MS medium. FIG. 11 exemplifies transformed somatic embryos established to have kanamycin resistance and transformed to have resistance to the herbicide glyphosate. FIG. 12 exemplifies cotton plants obtained by inoculating tissues with Agrobacterium containing a mutant AroA gene and thereafter growing the tissues on non-selective media. FIG. 13 shows germinating somatic embryos of variety B1644 obtained from suspension cultures treated with the vector pCIB10/BTA-5, and selected on kanamycin (50 mg/L) or G418 (25 mg/L) supplemented media. FIG. 14 shows plantlets developed from the embryos of FIG. 13. FIG. 15 shows a plantlet of the variety Siokra developed from transformed embryos exhibiting a resistance to kanamycin.

COTTON REGENERATION

EXAMPLE 1

Regeneration of Plants Starting from Cotyledon Explants

Seeds of Acala cotton variety SJ2 of *Gossypium hirsutum* were sterilized by contact with 95 alcohol for three minutes, then twice rinsed with sterile water and immersed with a 15% solution of sodium hypochlorite for 15 minutes, then rinsed in sterile water. Sterilized seeds were germinated on a basal agar medium in the dark for approximately 14 days to produce a seedling. The cotyledons of the seedlings were cut into segments of 2–4 mm$^2$ which were transferred aseptically to a callus inducing medium consisting of Murashige and Skoog (MS) major and minor salts supplemented with 0.4 mg/l thiamine-HCl, 30 g/l glucose, 2.0 mg/l NAA, 1 mg/l kinetin, 100 mg/l of m-inositol, and agar (0.8% w/v). The cultures were incubated at about 30° C. under conditions of 16 hours light and 8 hours darkness in a Percival incubator with fluorescent lights (cool daylight) providing a light intensity of about 2000–4000 lux.

Calli were formed on the cultured tissue segments within 3 to 4 weeks and were white to gray-greenish in color. The calli formed were subcultured every three to four weeks onto a callus growth medium comprising MS medium containing 100 mg/l m-inositol, 20 g/l sucrose, 2 mg/l NAA and agar. Somatic embryos formed four to six months after first placing tissue explants on a callus inducing medium. The callus and embryos were maintained on a callus growth medium by subculturing onto fresh callus growth medium every three to four weeks.

Somatic embryos which formed on tissue pieces were explanted either to fresh callus growth medium, or to Beasley & Ting's medium (embryo germination medium).

The somatic plantlets which were formed from somatic embryos were transferred onto Beasley and Ting's medium which contained 1200 mg/l ammonium nitrate and 500 mg/l casein hydrolysate as an organic nitrogen source. The medium was solidified by a solidifying agent (Gelrite) and plantlets were placed in Magenta boxes.

The somatic embryos developed into plantlets within about three months. The plantlets were rooted with six to eight leaves and about three to four inches tall and were transferred to soil and maintained in an incubator under high humidity for three to four weeks and then transferred to a greenhouse. After hardening, plants were also transferred to open tilled soil.

EXAMPLE 2

The procedure of Example 1 was repeated using instead half-strength MS medium in which all medium components have been reduced to one-half the specified concentration. Essentially the same results were obtained.

EXAMPLE 3

The procedures of Examples 1 and 2 were repeated except that the explant was the hypocotyl segments. The same results were obtained.

EXAMPLE 4

The procedure of Examples 1 and 2 were repeated except that the explant was the immature zygotic embryo. Essentially the same results were obtained.

EXAMPLE 5

The procedure of Examples 1 and 2 was repeated with Acala cotton varieties SJ4, SJ5, SJ2C-1, GC510, B1644, B2724, B1810, the picker variety Siokra and the stripper variety FC2017. All were successfully regenerated.

EXAMPLE 6

The procedure of Example 1 was repeated to the extent of obtaining callus capable of forming somatic embryos. Pieces of about 750–1000 mg of actively growing embryogenic callus was suspended in 8 ml units of liquid suspension culture medium comprised of MS major and minor salts, supplemented with 0.4 mg/l thiamine HCl, 20 g/l sucrose, 100 mg/l of inositol and naphthaleneacetic acid (2 mg/l) in T-tubes and placed on a roller drum rotating at 1.5 rpm under 16:8 light:dark regime. Light intensity of about 2000–4500 lux was again provided by fluorescent lights (cool daylight).

After four weeks, the suspension was filtered through an 840 micron size nylon mesh to remove larger cell clumps. The fraction smaller than 840 microns were allowed to settle, washed once with about 20–25 ml of fresh suspension culture medium. This suspension was transferred to T-tubes (2 ml per tube) and each tube diluted with 6 ml of fresh suspension culture medium. The cultures were maintained by repeating the above procedure at 10–12 day intervals. Namely, the suspension was filtered and only the fraction containing cell aggregates smaller than 840 microns was transferred to fresh suspension culture medium. In all instances, the fraction containing cell clumps larger than 840 microns was placed onto the callus growth medium to obtain mature somatic embryos.

The somatic embryos that were formed on callus growth medium were removed and transferred to embryo germination medium and using the protocol of Example 1 were germinated, developed into plantlets and then field grown plants.

EXAMPLE 7

The procedure of Example 6 was repeated except that suspension cultures were formed by transferring 750–1000 mg of embryogenic calli to a DeLong flask containing 15–20 ml of the MS liquid medium containing 2 mg/l NAA. The culture containing flask was placed on a gyrotory shaker and shaken at 100–110 strokes/minute. After three weeks the suspension was filtered through an 840 micron nylon mesh to remove the large cell clumps for plant growth, as in Example 4. The less than 840 micron suspension was allowed to settle, washed once in the MS liquid medium and resuspended in 2 to 5 ml of the MS liquid medium. The suspension was subcultured by transfer to fresh medium in a DeLong flask containing 1–2 ml of suspension and 15 ml of fresh MS liquid medium. The cultures are maintained by repeating this procedure at seven to ten day intervals. At each subculture only the less than 840 micron suspension was subcultured and the large clumps (840 microns or greater) were used for plant growth.

EXAMPLE 8

After three or four subcultures using the suspension growth procedure of Examples 6 and 7, 1.5 to 2.0 ml of cell suspension from the T-tube and DeLong flask were in each instance plated onto agar-solidified MS medium containing 2 mg/l NAA and Beasley & Ting medium containing 500 mg/l casein hydrolysate. Within three to four weeks embryogenic calli with developing embryos became visible. Again, the 840 micron or greater cell clumps were plated on the callus growth medium giving rise to embryogenic clumps with developing embryos which ultimately grew into plants.

EXAMPLE 9

The method of Example 1 was repeated with cotton varieties B1654–26, B1654-43, B3991, Acala Royale, B4894, COKER 315, STONEVILLE 506, FC 3027, CHEMBRED B2 and CHEMBRED C4.

EXAMPLE 10

The method of Example 1 was repeated with cotton varieties GC356, GAM1, B638, B5002, STONEVILLE 825, HBX87, SICALA, PIMA S6, ORO BLANCO PIMA except plants were not obtained from the somatic embryos.

EXAMPLE 11

The method of Example 1 was repeated with cotton varieties Acala Maxxa, Acala Prema, B2086, FC 3027, DP50, DP61, DP90, DP77, DES119, McN235, HBX191, HBX107, CHEMBRED A1, CHEMBRED A2, CHEMBRED A3, CHEMBRED A4, CHEMBRED B1, CHEMBRED B3, CHEMBRED C1, CHEMBRED C2, CHEMBRED C3, PAYMASTER 145, HS26 and HS46 except embryos and plants were not developed from the callus.

Below is a summary of the varieties which have been regenerated and the stage to which they have been grown.

| Example No. | VARIETY | $C^1$ | $E^2$ | $P^3$ |
|---|---|---|---|---|
| Example 1 | Acala SJ2 | $+^4$ | + | + |
| Example 5 | Acala SJ4 | + | + | + |
| Example 5 | Acala SJ5 | + | + | + |
| Example 5 | Acala SJ-C1 | + | + | + |
| Example 10 | Acala GC356 | + | + | $-^5$ |
| Example 5 | Acala CG510 | + | + | + |
| Example 5 | Acala B1644 | + | + | + |
| Example 9 | Acala B1654-26 | + | + | + |
| Example 9 | Acala B1654-43 | + | + | + |
| Example 9 | Acala B3991 | + | + | + |
| Example 10 | Acala GAM1 | + | + | – |
| Example 9 | Acala Royale | + | + | + |
| Example 11 | Acala Maxxa | + | – | – |
| Example 11 | Acala Prema | + | – | – |
| Example 10 | Acala B638 | + | + | – |
| Example 5 | Acala B1810 | + | + | + |
| Example 5 | Acala B2724 | + | + | + |
| Example 12 | Acala B2086 | + | – | – |
| Example 9 | Acala B4894 | + | + | + |
| Example 10 | Acala B5002 | + | + | – |
| Example 9 | COKER 315 | + | + | + |
| Example 9 | STONEVILLE 506 | + | + | + |
| Example 10 | STONEVILLE 825 | + | + | – |
| Example 11 | DP50 | + | – | – |
| Example 11 | DP61 | + | – | – |
| Example 11 | DP90 | + | – | – |
| Example 11 | DP77 | + | – | – |
| Example 11 | DES119 | + | – | – |
| Example 11 | McN235 | + | – | – |
| Example 10 | HBX87 | + | + | – |
| Example 11 | HBX191 | + | – | – |
| Example 11 | HBX107 | + | – | – |
| Example 9 | FC 3027 | + | + | + |
| Example 5 | FC 2017 | + | – | – |
| Example 11 | FC 2005 | + | – | – |
| Example 11 | FC C1042-R-9-1 | + | – | – |
| Example 11 | CHEMBRED A1 | + | – | – |
| Example 11 | CHEMBRED A2 | + | – | – |
| Example 11 | CHEMBRED A3 | + | – | – |

-continued

| Example No. | VARIETY | REGENERATION | | |
|---|---|---|---|---|
| | | C[1] | E[2] | P[3] |
| Example 11 | CHEMBRED A4 | + | − | − |
| Example 11 | CHEMBRED B1 | + | − | − |
| Example 9 | CHEMBRED B2 | + | + | + |
| Example 11 | CHEMBRED B3 | + | − | − |
| Example 11 | CHEMBRED C1 | + | − | − |
| Example 11 | CHEMBRED C2 | + | − | − |
| Example 11 | CHEMBRED C3 | + | − | − |
| Example 9 | CHEMBRED C4 | + | + | + |
| Example 11 | PAYMASTER 145 | + | − | − |
| Example 11 | HS26 | + | − | − |
| Example 11 | HS46 | + | − | − |
| Example 5 | SIOKRA | + | + | + |
| Example 10 | SICALA | + | + | − |
| Example 10 | PIMA S6 | + | + | − |
| Example 10 | ORO BLANCO PIMA | + | + | − |

[1]Callus
[2]Embryos
[3]Plants
[4]+ indicates that the indicated tissue was obtained
[5]− indicates that the indicated tissue was not obtained

COTTON TRANSFORMATION

EXAMPLE 12

Transformation to Form Tumorous-phenotype With Agrobacteria LBA 4434

An Acala cotton suspension culture was subcultured for three to four months in T-tubes with the medium (MS medium containing 2 mg/l NAA) being changed every seven to ten days. After any medium change thereafter the cells can be allowed to settle and harvested for transformation. The supernatant was removed by pipeting and cells transformed with the Agrobacterium strain LBA 4434. The Agrobacterium strain LBA 4434 [described in Hoekema et al., Nature 303 179–180 (1983), incorporated herein by reference] contains a Ti plasmid-derived binary plant transformation system. In such binary systems, one plasmid contains the T-DNA of a Ti-plasmid, the second plasmid contains the vir-region of a Ti-plasmid. The two plasmids cooperate to effect plant transformation. In the strain LBA 4434, the T-DNA plasmid, pAL1050, contains $T_L$ of pTiAch5, an octopine Ti-plasmid and the vir-plasmid in strain LBA4434, pAL4404, contains the intact virulence regions of pTiAch5 [Ooms et al., Plasmid 7 15–29 (1982), incorporated herein by reference]. Strain LBA 4434 is available from Dr. Robert Schilperoort of the Department of Biochemistry, University of Leiden, The Netherlands.

The transforming Agrobacterium strain was taken from a glycerol stock, inoculated in a small overnight culture, from which a 50-ml culture was inoculated the following day. Agrobacteria was grown on YEB medium containing per liter in water adjusted to pH 7.2 with NaOH, 5 g beef extract, 1 g yeast extract, 5 g peptone, 5 g sucrose. After autoclaving, 1 ml of 2 M $MgCl_2$ is added after which antibiotics, as required to kill other strains. The absorbance at 600 nm of the 50 ml overnight culture is read, the culture centrifuged and the formed pellet resuspended in the plant cell growth medium (MS medium plus NAA at 2 mg/l) to a final absorbance at 600 nm of 0.5.

Eight ml of this bacterial suspension of Agrobacterium LBA 4434 was added to each T-tube containing the suspension plant cells after removal of the supernatant liquid. The T-tube containing the plant and bacteria cells was agitated to resuspend the cells and returned to a roller drum for three hours to allow the Agrobacteria to attach to the plant cells. The cells were then allowed to settle and the residual supernatant removed. A fresh aliquot of growth medium was added to the T-tube and the suspension allowed to incubate on a roller drum for a period of 18 to 20 hours in the presence of any residual Agrobacteria which remained. After this time, the cells were again allowed to settle, the supernatant removed and the cells washed twice with a solution of growth medium containing cefotaxime (200 μg/ml). After washing, the cells from each T-tube were resuspended in 10 ml growth medium containing cefotaxime (200 μg/ml in all cases) and 1 ml aliquots of the suspension plated on petri dishes.

Infected cells grew on the growth medium to which no phytohormones were added establishing the tissue had received the wild-type phytohormone genes in T-DNA. The cells developed tumors, further indicating transformation of the cultures.

EXAMPLE 13

Transformation of Cotton to Form a Kanamycin-resistant Non-tumorous Phenotype

The suspension culture as obtained in Example 12 is transformed using an Agrobacteria containing the T-DNA which contains binary vector pCIB10 [Rothstein et al., Gene 53 153–161 (1987), incorporated herein by reference] as well as the pAI4404 vir-plasmid. The T-DNA of pCIB10 contains a chimeric gene composed of the promoter from nopaline syntliase, the coding region Crom Tn5 encoding the enzyme neomycin phosphotransferase, and the terminator from nopaline synthase. The Agrobacteria containing pCIB10 are grown on YEB medium containing kanamycin (50 μg/ml). Transformation is accomplished in the same manner as in Example 12 except that the 1 ml aliquots resulting in cells and Agrobacteria are immediately plated on selective media containing either kanamycin (50 μg/ml) or G418 (25 μg/ml). Expression of the nos/nco/nos chimeric gene in transformed plant tissue allows the selection of this tissue in the presence of both antibiotics. The existence of transformed tissue is apparent on the selection plates in two to four weeks. Uninfected tissue as well as added control tissue will show no signs of growth, turn brown and die. Transformed tissue grows very well in the presence of both kanamycin and G418.

At this time, tissue pieces which are growing well are subcultured to fresh selection medium. Somatic embryos form on these tissue pieces and are explanted to fresh non-selective growth media. When the embryos begin to differentiate and germinate, i.e., at the point where they begin to form roots and have two or three leaves, they are transferred to Magenta boxes containing growth medium described in Example 1. Growth is allowed to proceed until the plantlet has six to eight leaves, at which time it is removed from the agar medium.

The plantlets are now placed in potting soil, covered with a beaker to maintain humidity and placed in a Percival incubator for four to eight weeks. At this time, the plant is removed from the beaker and transferred to a greenhouse. The plants grow in the greenhouse, flower and set seed.

EXAMPLE 14

The procedure of Example 13 was followed, except that the transforming Agrobacteria used contained the T-DNA vector DEI PEP10 as well as the pAL4404 vir plasmid. DEI PEP10, shown in FIG. 33, utilizes two T-DNA PstI cleaved right border sequences from *A. tumefaciens* (strain C-58) which had been further subdivided with BamHI for integration in the plant genome, a passenger maize phosphoenolpyruvate carboxylase gene (Pepcase gene), and a chimeric gene (NOS/NPT/TK) capable of expression in plants and conferring resistance to the antibiotics kanamycin and G418. This chimeric gene utilizes a nopaline synthetase promoter, the neomycin phosphotransferase II coding region from Tn5, and the terminator from the herpes simplex virus thymidine kinase gene. Following transformation, embryogenic callus and embryos were obtained by selection on kanamycin (50 mg/l). No resistant callus was obtained from the control (non-transformed callus) plated on kanamycin at this level (50 mg/l).

EXAMPLE 15

Transformation of Cotton Suspension Culture Cells to a Glyphosate-tolerant Phenotype The procedure of Example 13 was followed, except that the transforming Agrobacteria used contained the T-DNA vector pPMG85/587 [Fillatti et al., *Mol. Gen. Genet.* 206 192–199 (1987) incorporated herein by reference] as well as the pAL4404 vir plasmid. The plasmid pPMG85/587 carries three chimeric genes capable of expression in plants. Two genes code for neomycin phosphotransferase (NPT) which confers resistance to the antibiotics kanamycin and G418. The third chimeric gene, containing the coding sequence from a mutant aroA gene of *S. typhimurium*, confers tolerance to the herbicide glyphosate [Comai et al., *Science* 221 370–371 (1983), incorporated herein by reference] . The Agrobacteria containing pPMG85/587 were grown on medium containing kanamycin (100 μg/ml). Transformation is accomplished as detailed in Example 13 except that the suspension is allowed to grow for 28 days at which time 1 ml aliquots were plated on medium containing selective antibiotics. Expression of the NPT chimeric gene in transformed plant tissue allowed selection of this tissue on both antibiotics. In this instance the selective antibiotic was kanamycin (50 μg/ml).

In two to four weeks, transformed tissue became apparent on the selection plates. Plant tissue, individual embryos and callus were then placed on growth medium containing the herbicide glyphosate 1 mM and transformed tissue continued to grow well. Extraction and analysis of the proteins of both callus and embryos confirmed the presence of the product of the glyphosate tolerance gene.

EXAMPLE 16

Transformation of Cotton Suspension Culture Cells to a Hygromycin-resistant Non-tumorous Phenotype The transformation procedure of Example 13 was followed except there was used as the transforming Agrobacteria one containing the T-DNA binary vector pCIB715 [Rothstein et al. *Gene* 53 153–161 (1987)] as well as the vir plasmid. The T-DNA of pCIB715 contains a chimeric gene composed of the promoter and terminator from the cauliflower mosaic virus (CaMV) 35S transcript [Odell et al., *Nature* 313 810–812 (1985), incorporated herein by reference] and the coding sequence for hygromycin B phosphotransferase [Gritz et al., *Gene* 25 179–188 (1983) incorporated herein by reference]. Agrobacteria containing pCIB715 was grown on YEB containing kanamycin (50 μg/ml).

Transformation was accomplished as detailed in Example 14 again with the change that the 1 ml aliquots were plated immediately on medium containing as the selective antibiotic 50 μg/ml hygromycin. Expression of the chimeric hygromycin gene in transformed plant tissue allows the selection of this tissue on the medium containing hygromycin. Transformed tissue was grown in the manner described in Example 8 on the selection growth medium establishing transformation had occurred.

EXAMPLE 17

Transformation of Cotton Suspension Culture Cells to Confer Resistance to Lepidopteran Insects The procedure of Example 14 was followed except where changes are noted below. Different transforming Agrobacteria were used. Also, after plant tissue was selected on an antibiotic for the selection of transformed material, it was further selected for expression of the BT gene as defined herein.

Figure 16:
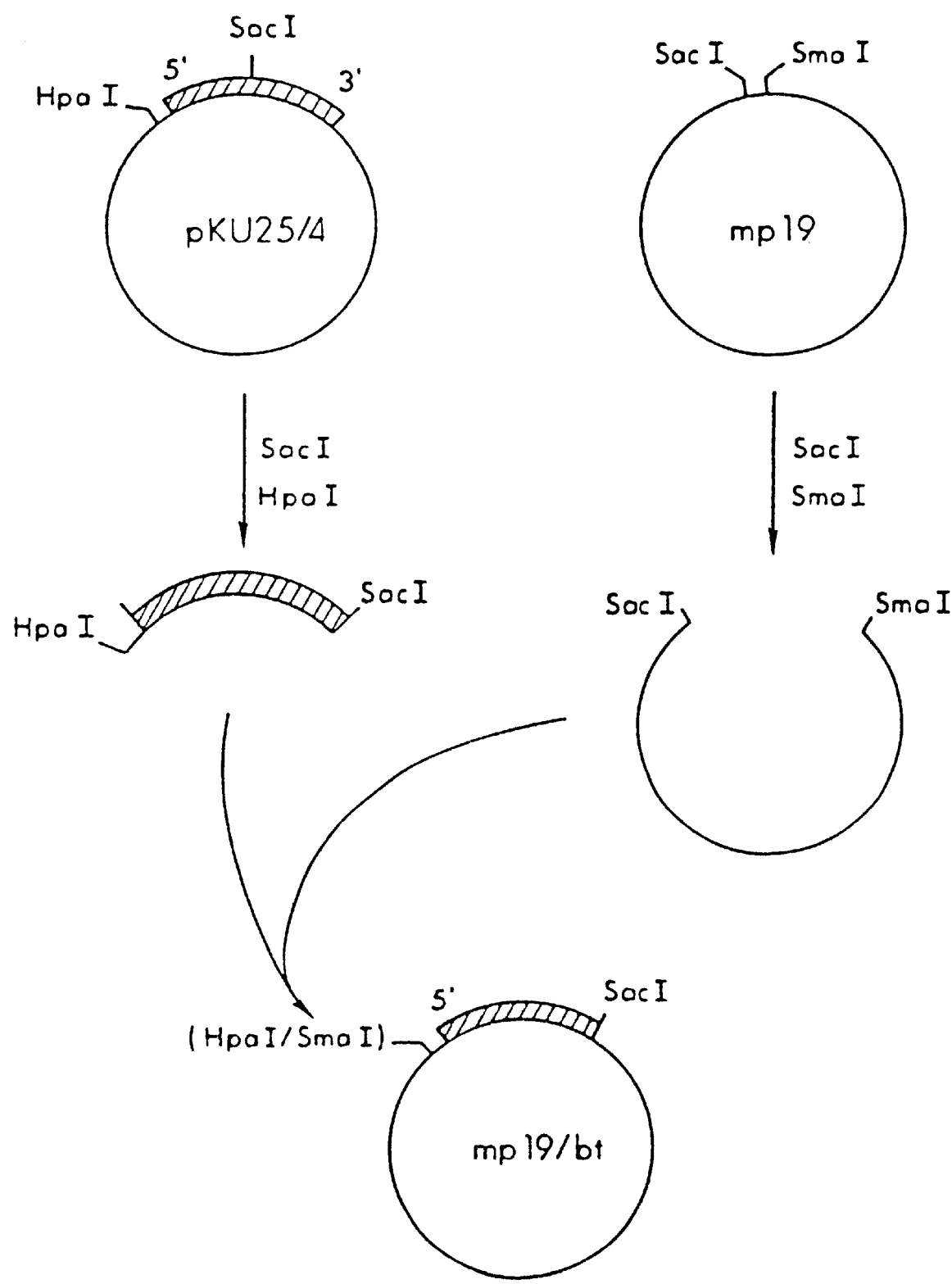
FIG. 16 shows the construction of mp19/bt, a plasmid containing the 5' end of the Bt protoxin gene.
Figure 17:
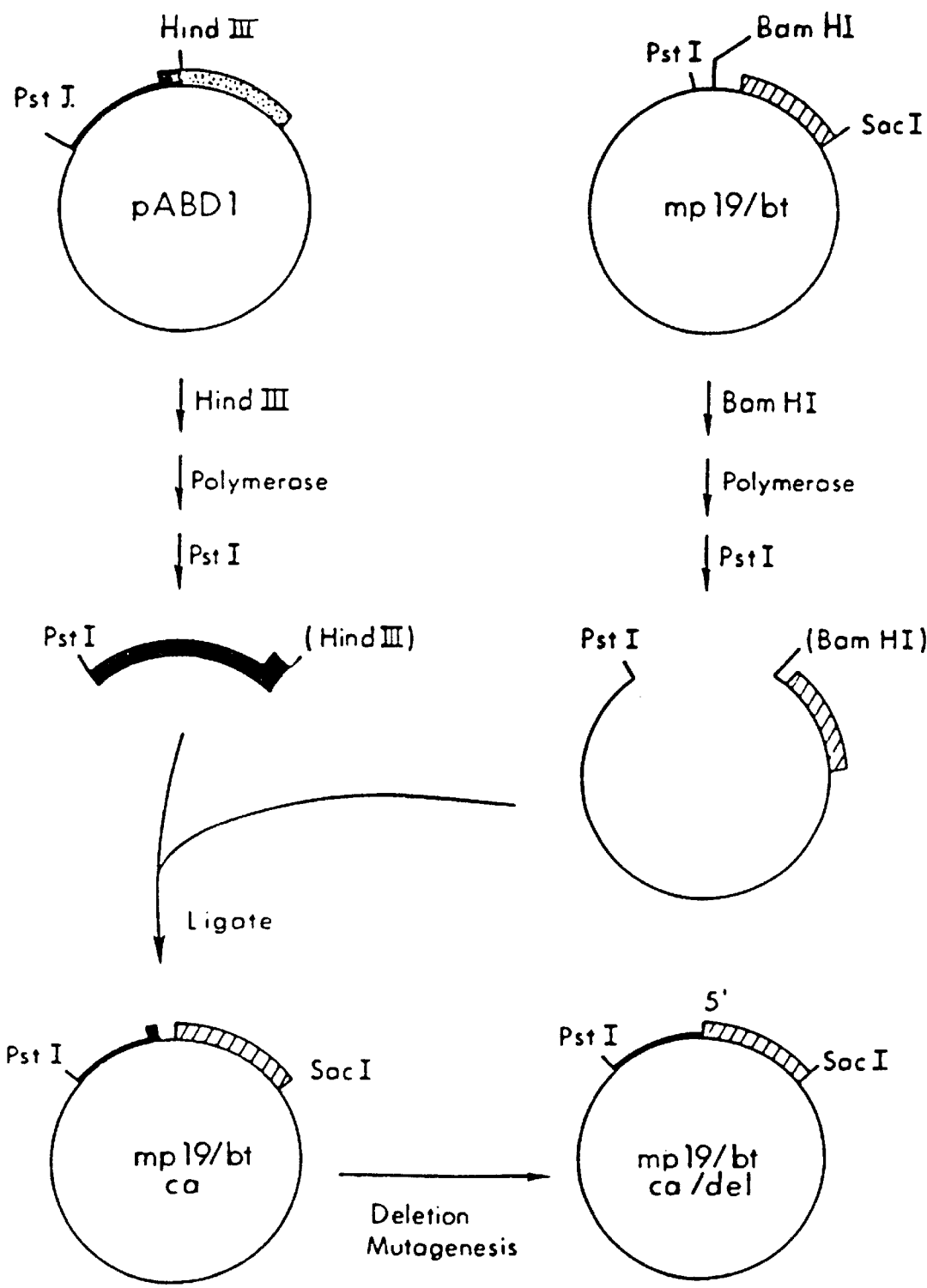
FIG. 17 shows the construction of mp19/bt ca/del, a plasmid containing the CaMV gene VI promotor fused to the 5' end of Bt protoxin co -continued
Figure 18:
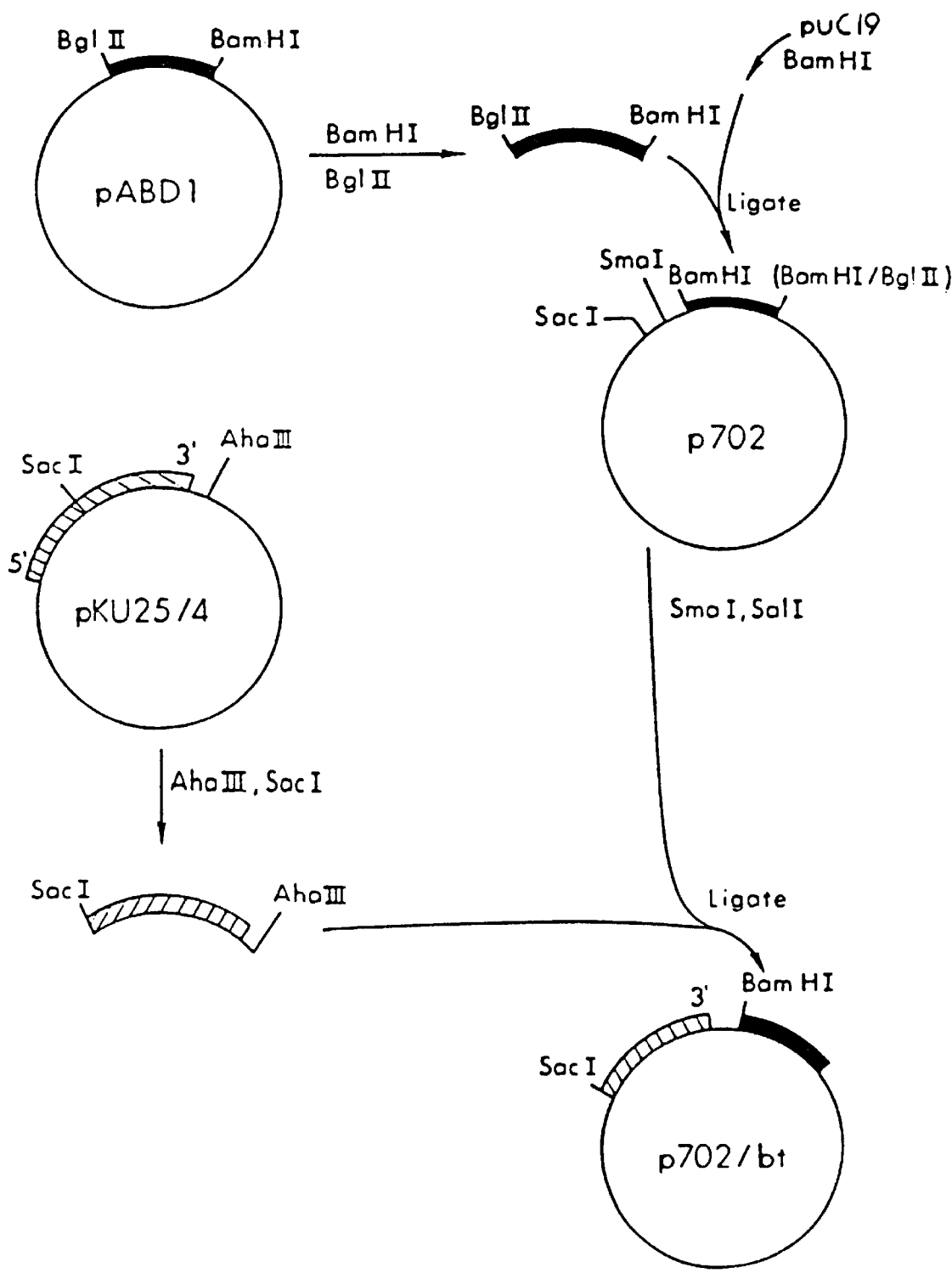
Figure 19:
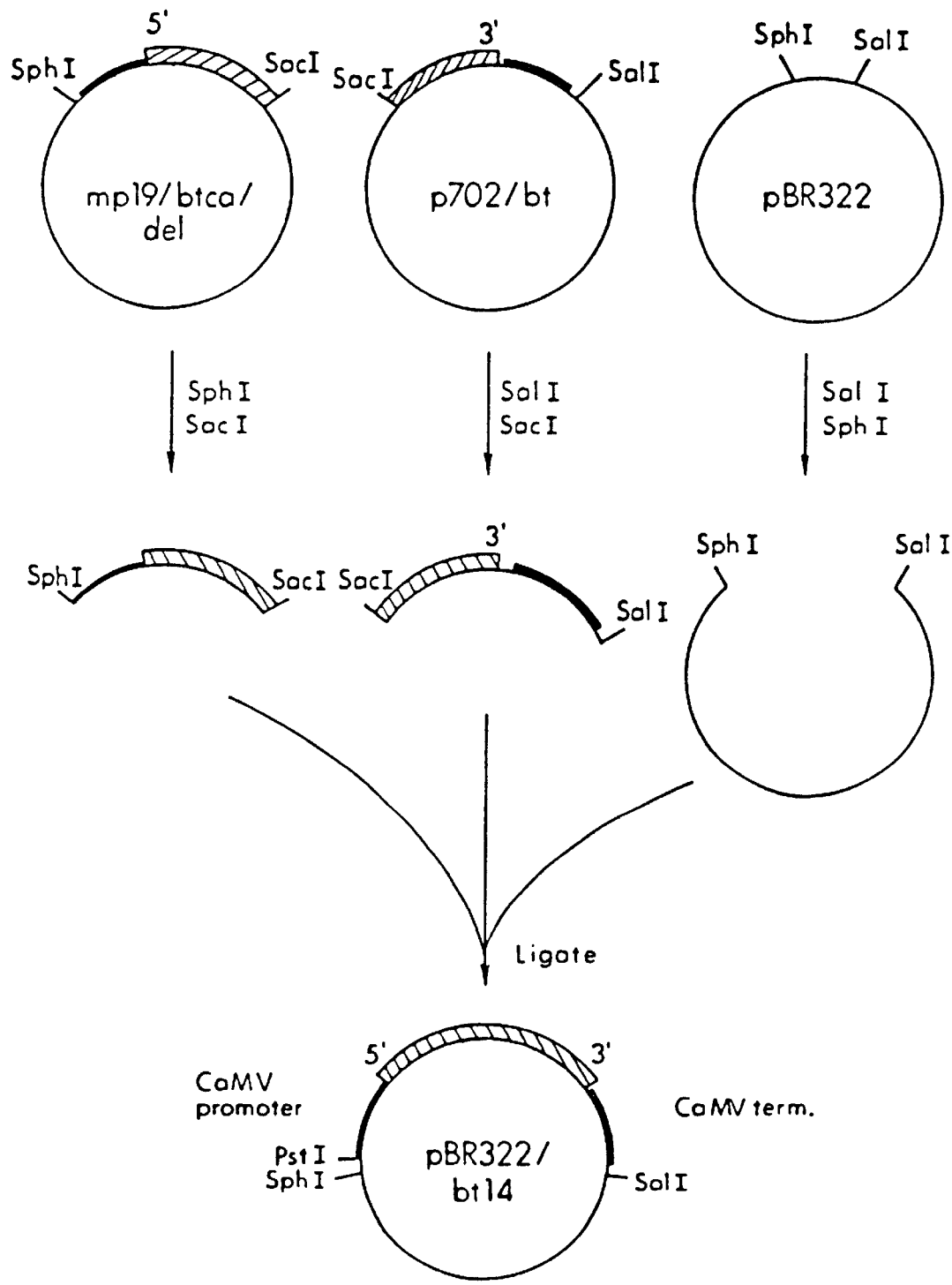

The Agrobacteria used contained the T-DNA vector pCIB10 [Rothstein et al., *Gene* 53 153–161 (1987) incorporated herein by reference] into which had been inserted the following chimeric *Bacillus thuringiensis* endotoxin genes ("BT Genes"):

To prepare the Agrobacterium vector there was fused the CaMV gene VI promotor and protoxin coding sequences. A derivative of phage vector mp19 [Yanish-Perron et al., 1985] was first constructed. The steps are shown in FIGS. 16 and 17. First, a DNA fragment containing approximately 155 nucleotides 5' to the protoxin coding region and the adjacent approximately 1346 nucleotides of coding sequence are inserted into mp19. Phage mp19 ds rf (double-stranded replicative form) DNA was digested with restriction endonucleases SacI and SmaI and the approximately 7.2-kb (kilobase pairs) vector fragment was purified after electrophoresis through low-gelling temperature agarose by standard procedures. Plasmid pKU25/4, containing approximately 10 kb of *Bacillus thuringiensis* DNA, including the protoxin gene, was obtained from Dr. J. Nueesch, CIBA-S Geigy Ltd., Basle, Switzerland. The nucleotide sequence of the protoxin gene present in plasmid pKU25/4 is shown in SEQ ID NO: 1 below. Plasmid pKU25/4 DNA was digested with endonucleases HpaI and SacI, and a 1503 bp fragment containing nucleotides 2 to 1505 of SEQ ID NO: 1 and purified. This fragment contains approximately 155 bp of bacteria promotor sequences and approximately 1346 bp of the start of the protoxin coding sequence. Approximately 100 ng of each fragment is then mixed, T4 DNA ligase added, and incubated at 15° C. overnight. The resulting mixture was transformed into *E. coli* strain HB101, mixed with indicator bacteria *E. coli* JM101 and plated. One phage (mp19/bt) was used for further construction below.

Figure 21:
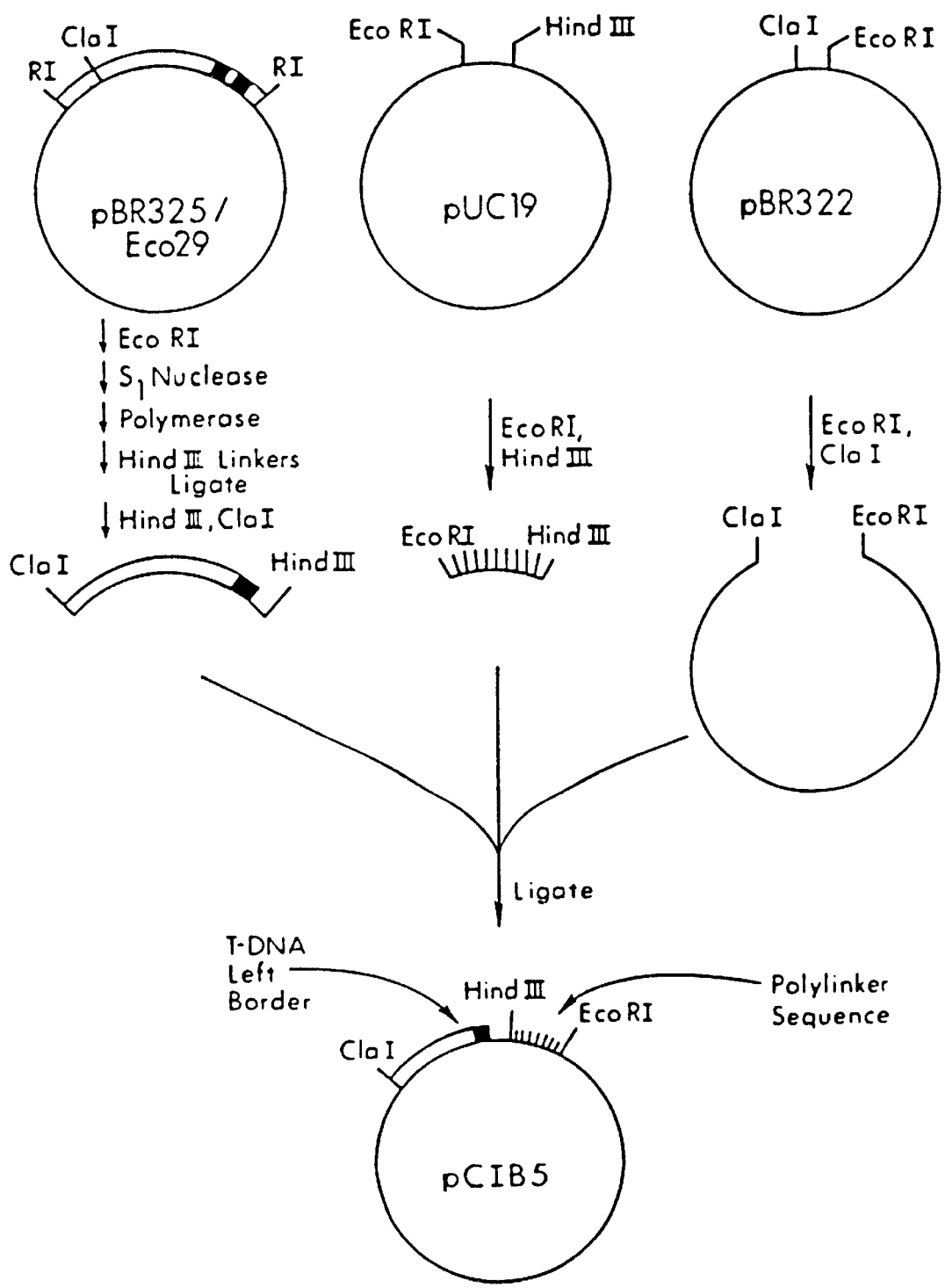

Next, a fragment of DNA containing the CaMV gene VI promotor, and some of the coding sequences for gene VI, was inserted into mp19/bt. Phage mp19/bt ds rf DNA is digested with BamHI, treated with the large fragment of DNA polymerase to create flush ends and recleaved with endonuclease PstI. The larger vector fragment was purified by electrophoresis as described above. Plasmid pABD1 [described in Paszkowski et al., *EMBO J.* 3 2717–2722 (1984) incorporated herein by reference]. Plasmid pABD1 DNA is digested with PstI and HindIII. The fragment approximately 465 bp long containing the CaMV gene VI promotor and approximately 75 bp of gene VI coding sequence was purified. The two fragments were ligated and plated as described above. One of the resulting recombinant phages, mp19/btca contained the CaMV gene VI promotor sequences, a portion of the gene VI coding sequence, approximately 155 bp of *Bacillus thuringiensis* DNA upstream of the protoxin coding sequence, and approximately 1346 bp of the protoxin coding sequence. To fuse the CaMV promotor sequences precisely to the protoxin coding sequences, the intervening DNA was deleted using oligonucleotide-directed mutagenesis of mp19/btca DNA. A DNA oligonucleotide with the sequence 5'-TTCGGATTGTTATCCATGGTTGGAGGTCTGA-3' was synthesized by routine procedures using an Applied Biosystems DNA Synthesizer. This oligonucleotide is complimentary to those sequences in phage mp19/btca DNA at the 3' end of the CaMV promotor [nucleotides 5762 to 5778 see *Hohn Current Topics in Microbiology and Immunology* 96 193–235 (1982) incorporate herein by reference] and the beginning of the protoxin coding sequence (nucleotides 156 to 172 in formula I above). The general procedure for the mutagenesis is that described in Zoller et al. [*Methods in Enzymology* 100 468–500 (1983) incorporated herein by reference]. Approximately five micrograms of single-stranded phage mp19/btca DNA was mixed with 0.3 mg of phosphorylated oligonucleotide in a volume of 40 μl. The mixture was heated to 65° C. for 5 min, cooled to 50° C., and slowly cooled to 4° C. Next, buffer, nucleotide triphosphates, ATP, $T_4$ DNA ligase and large fragment of DNA polymerase were added and incubated overnight at 15° C. as described by Zoller et al. [*Methods in Enzymology* 100 468–500 (1983) incorporated herein by reference] . After agarose gel electrophoresis, circular double-stranded DNA was purified and transfected into *E. coli* strain JM101. The resulting plaques are screened for sequences that hybridize with 32P-labeled oligonucleotide, and phage are analyzed by DNA restriction endonuclease analysis. Among the resulting phage clones were ones which have correctly deleted the unwanted sequences between the CaMV gene VI promotor and the protoxin coding sequence. This phage is called mp19/btca/del (see FIG. 17).

Next, a plasmid was constructed in which the 3' coding region of the protoxin gene was fused to CaMV transcription termination signals. The steps are shown in FIG. 18. First, plasmid pABDI DNA was digested with endonucleases BamHI and BglII and a 0.5 kb fragment containing the CaMV transcription terminator sequences isolated. Next plasmid pUC19 [Yanisch-Perron et al., *Gene* 33 103–119 (1985) incorporated herein by reference] was digested with BamHI, mixed with the 0.5 kb fragment and incubated with $T_4$ DNA ligase. After transformation of the DNA into *E. coli* strain HB101, one of the resulting clones, called plasmid p702, was obtained which has the structure shown in FIG. 18. Next, plasmid p702 DNA was cleaved with endonucleases SacI and SmaI, and the larger, approximately 3.2 kb fragment isolated by gel electrophoresis. Plasmid pKU25/4 DNA was digested with endonucleases AhaIII and SacI, and the 2.3-kb fragment (nucleotides 1502 to 3773 of SEQ ID NO: 1) containing the 3' portion of the protoxin coding sequence (nucleotides 1504 to 3773 of SEQ ID NO: 1) was isolated after gel electrophoresis. These two DNA fragments are mixed, incubated with $T_4$ DNA ligase and transformed into *E. coli* strain HB101. The resulting plasmid was p702/bt (FIG. 18).

Finally, portions of phage mp19/btca/del ds rf DNA and plasmid p702/bt were joined to create a plasmid containing the complete protoxin coding sequence flanked by CaMV promoter and terminator sequences (see FIG. 18). Phage mp19/btca/del DNA was digested with endonucleases SacI and SphI, and a fragment of approximately 1.75 kb is purified following agarose gel electrophoresis. Similarly, plasmid p702/bt DNA is digested with endonucleases SacI and SalI and a fragment of approximately 2.5 kb is isolated. Finally, plasmid pBR322 DNA [Bolivar et al., *Gene* 2 95–113 (1977) incorporated herein by reference] was digested with SalI and SphI and the larger 4.2-kb fragment isolated. All three DNA fragments were mixed and incubated with T4 DNA ligase and transformed into *E. coli* strain HB101. The resulting plasmid, pBR322/bt14 is a derivative of PBR322 containing the CaMV gene VI promoter and translation start signals fused to the *Bacillus thuringiensis* crystal protein coding sequence, followed by CaMV transcription termination signals (shown in FIG. 19).

The vector pCIB10 is a Ti-plasmid-derived vector useful for transfer of the chimeric gene to plants via *Agrobacterium tumefaciens*. The vector is derived from the broad host range plasmid pRK252, which may be obtained from Dr. W. Barnes, Washington University, St. Louis, Mo. The vector also contains a gene for kanamycin resistance in Agrobacterium, from Tn903, and left and right T-DNA border sequences from the Ti plasmid pTiT37. Between the border sequences are the polylinker region from the plasmid pUC18 and a chimeric gene that confers kanamycin resistance in plants.

First, plasmid pRK252 was modified to replace the gene conferring tetracycline-resistance with one conferring resistance to kanamycin from the transposon Tn903 [Oka et al., *J. Mol. Biol.* 147 217–226 (1981) incorporated herein by reference], and was also modified by replacing the unique EcoRI site in pRK252 with a BglII site (see FIG. 20 for a summary of these modifications). Plasmid pRK252 was first digested with endonucleases SalI and SmaI, then treated with the large fragment of DNA polymerase I to create flush ends, and the large vector fragment purified by agarose gel electrophoresis. Next, plasmid p368 was digested with endonuclease BamHI, treated with the large fragment of DNA polymerase, and an approximately 1050-bp fragment isolated after agarose gel electrophoresis; this fragment containing the gene from transposon Tn903 which confers resistance to the antibiotic kanamycin [Oka et al., *J. Mol. Biol.* 147 217–226 (1981) incorporated herein by reference]. Both fragments were then treated with the large fragment of DNA polymerase to create flush ends. Both fragments are mixed and incubated with T4 DNA ligase overnight at 15° C. After transformation into *E. coli* strain HB101 and selection for kanamycin resistant colonies, plasmid pRK252/Tn903 is obtained (see FIG. 19).

Plasmid pRK252/Tn903 was digested at its EcoRI site, followed by treatment with the large fragment of *E. coli* DNA polymerase to create flush ends. This fragment was added to synthetic BglII restriction site linkers, and incubated overnight with $T_4$ DNA ligase. The resulting DNA was digested with an excess of BglII restriction endonuclease and the larger vector fragment purified by agarose gel electrophoresis. The resulting fragment was again incubated with T4 DNA ligase to recircularize the fragment via its newly-added BglII cohesive ends. Following transformation into *E. coli* strain HB101, plasmid pRK252/Tn903/BglII is obtained (see FIG. 20).

A derivative of plasmid pBR322 was constructed which contains the Ti plasmid T-DNA borders, the polylinker region of plasmid pUC19, and the selectable gene for kanamycin. resistance in plants (see FIG. 21). Plasmid pBR325/Eco29 contains the 1.5-kb EcoRI fragment from the nopaline Ti plasmid pTiT37. This fragment contains the T-DNA left border sequence [Yadav et al., *Proc. Natl. Acad.*

Sci. USA 79 6322–6326 (1982) incorporated herein by reference]. To replace the EcoRI ends of this fragment with HindIII ends, plasmid pBR325/Eco29 DNA was digested with EcoRI, then incubated with nuclease Sl, followed by incubation with the large fragment of DNA polymerase to create flush ends, then mixed with synthetic HindIII linkers and incubated with T4 DNA ligase. The resulting DNA was digested with endonucleases ClaI and an excess of HindIII, and the resulting 1.1-kb fragment containing the T-DNA left border purified by gel electrophoresis. Next, the polylinker region of plasmid pUC19 was isolated by digestion of the plasmid DNA with endonucleases EcoRI and HindIII and the smaller fragment (approximately 53 bp) isolated by agarose gel electrophoresis. Next, plasmid pBR322 was digested with endonucleases EcoRI and ClaI, mixed with the other two isolated fragments, incubated with T4 DNA ligase and transformed into E. coli strain HB101. The resulting plasmid, pCIB5, contains the polylinker and T-DNA left border in a derivative of plasmid pBR322 (see FIG. 21).

Figure 22:
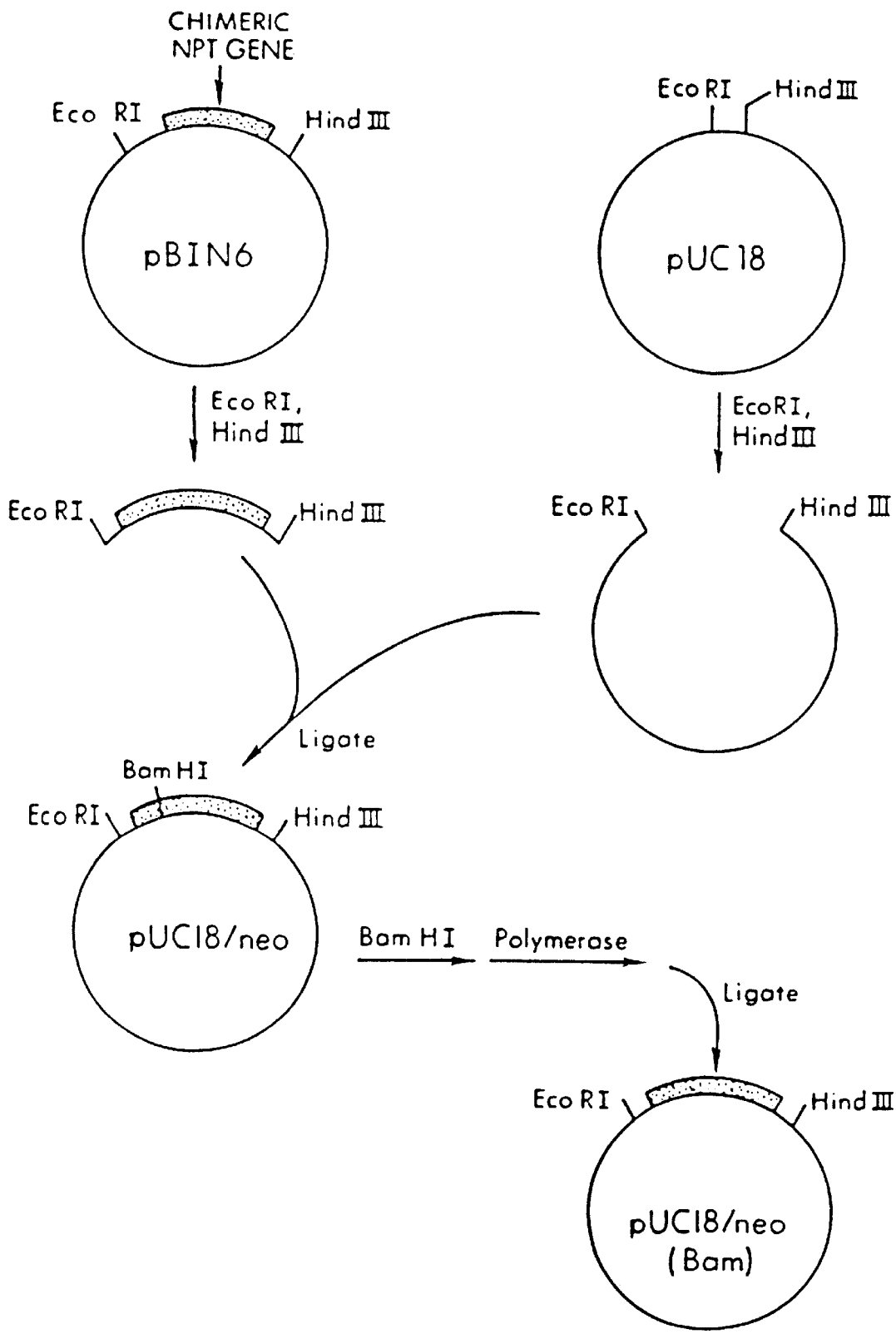
Figure 23:
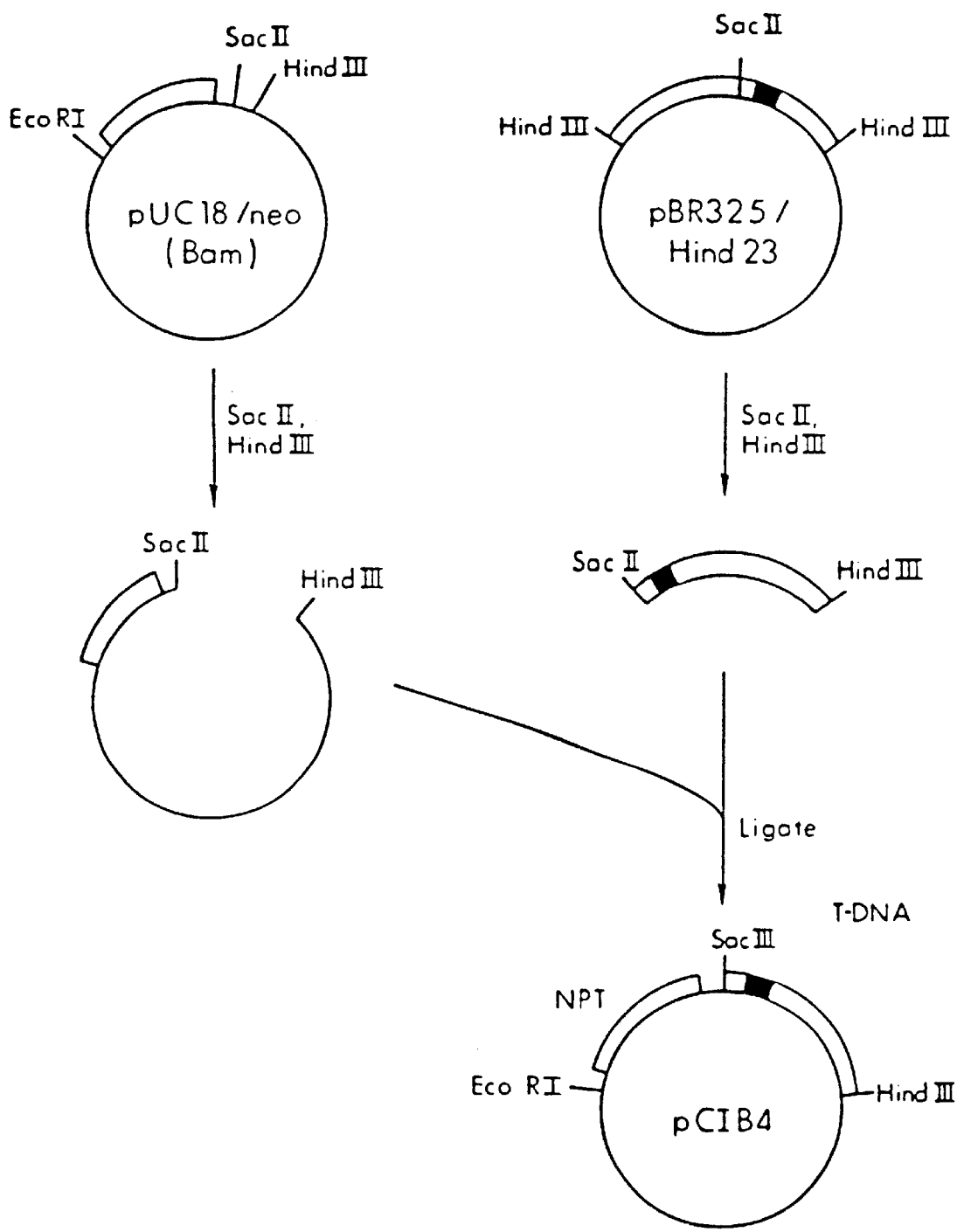

A plasmid containing the gene for expression of kanamycin resistance in plants was constructed (see FIGS. 22 and 23). Plasmid Bin6 obtained from Dr. M. Bevan, Plant Breeding Institute, Cambridge, UK. This plasmid is described in the reference by Bevan [Nucl. Acids Res. 12 8711–8721 (1984) incorporate herein by reference]. Plasmid Bin6 DNA was digested with EcoRI and HindIII and the fragment approximately 1.5 kb in size containing the chimeric neomycin phosphotransferase (NPT) gene is isolated and purified following agarose gel electrophoresis. This fragment was then mixed with plasmid pUC18 DNA which had been cleaved with endonucleases EcoRI and HindIII. Following incubation with T4 DNA ligase, the resulting DNA was transformed into E. coli strain HB101. The resulting plasmid is called pUC18/neo. This plasmid DNA containing an unwanted BamHI recognition sequence between the neomycin phosphotransferase gene and the terminator sequence for nopaline synthase [see *Bevan Nucl. Acids Res.* 12 8711–8721 (1984) incorporated herein by reference]. To remove this recognition sequence, plasmid pUC18/neo was digested with endonuclease BamHI, followed by treatment with the large fragment of DNA polymerase to create flush ends. The fragment was then incubated with T4 DNA ligase to recircularize the fragment, and transformed into E. coli strain HB101. The resulting plasmid, pUC18/neo(Bam) has lost the BamHI recognition sequence.

Figure 24:
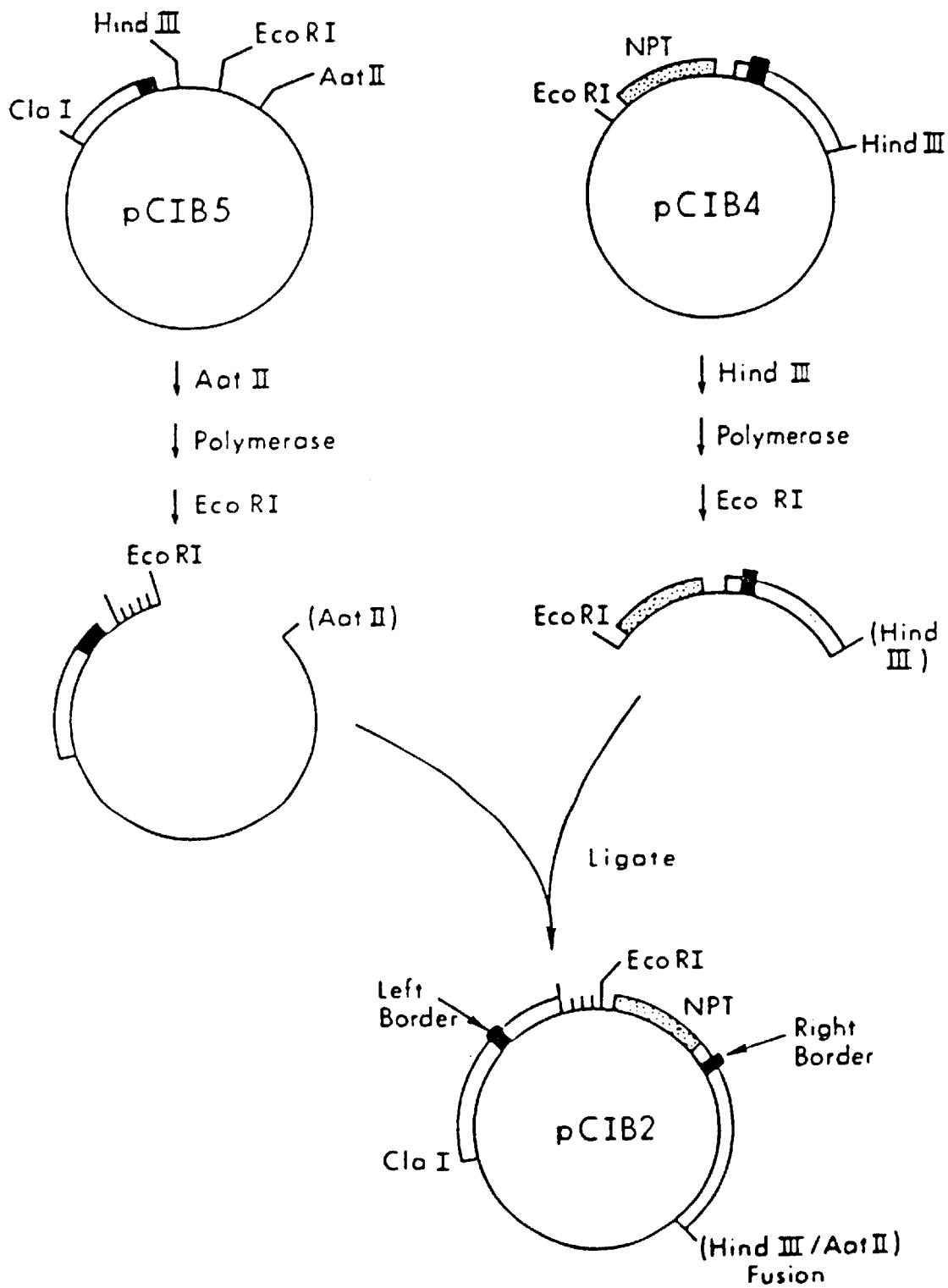

The T-DNA right border sequence was then added next to the chimeric NPT gene (see FIG. 24). Plasmid pBR325/Hind23 contains the 3.4-kb HindIII fragment of plasmid pTiT37. This fragment contains the right T-DNA border sequence [Bevan et al., *Nucl. Acids Res.* 11 369–385 (1983) incorporated herein by reference]. Plasmid pBR325/Hind23 DNA was cleaved with endonucleases SacII and HindIII, and a 1.0 kb fragment containing the right border isolated and purified following agarose gel electrophoresis. Plasmid pUC18/neo(Bam) DNA was digested with endonucleases SacII and HindIII and the 4.0 kb vector fragment isolated by agarose gel electrophoresis. The two fragments were mixed, incubated with T4 DNA ligase and transformed into E. coli strain HB101. The resulting plasmid, pCIB4 (shown in FIG. 23), contains the T-DNA right border and the plant-selectable marker for kanamycin resistance in a derivative of plasmid pUC18.

Figure 28:
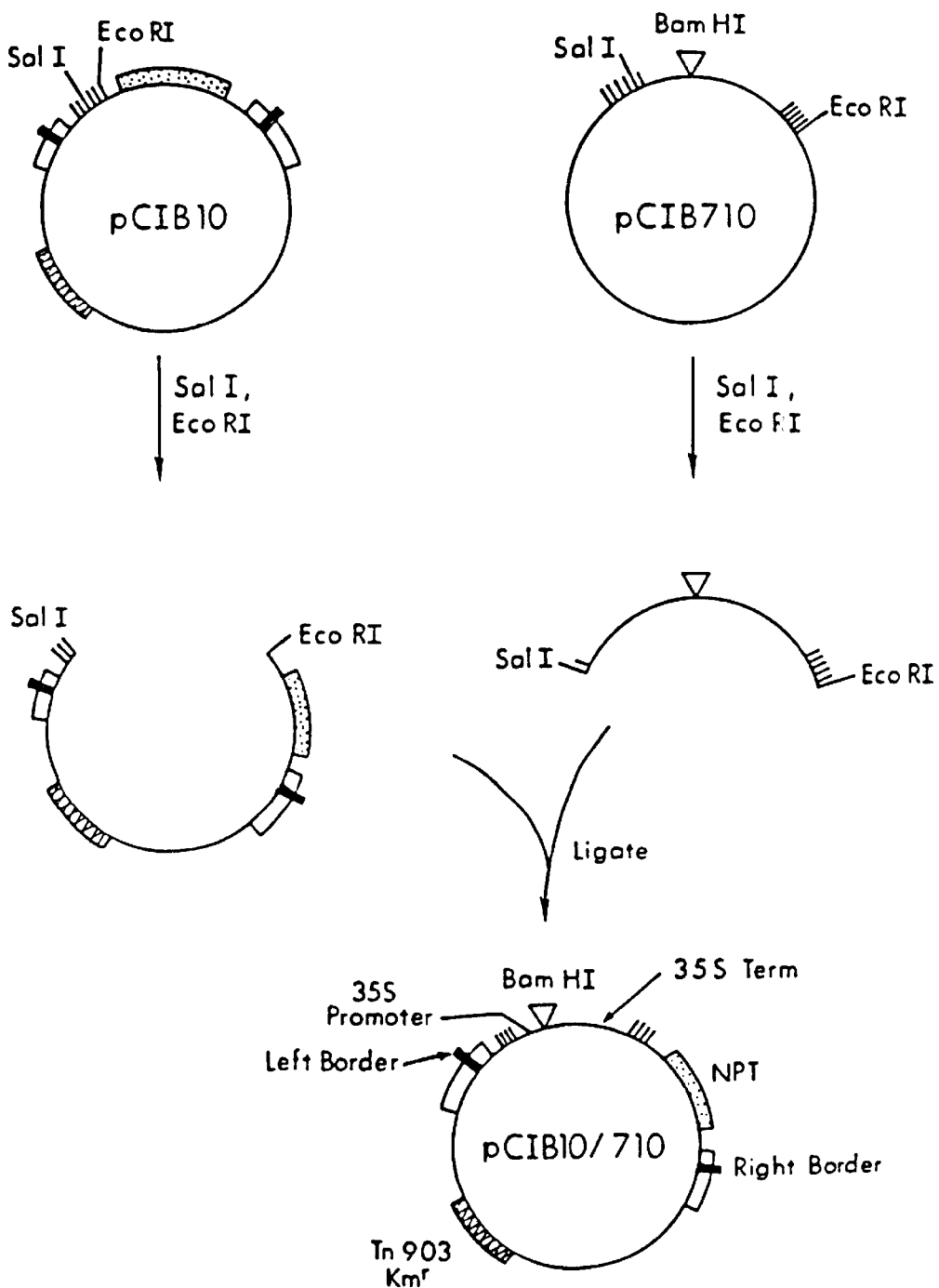

Next, a plasmid was constructed which contains both the T-DNA left and right borders, with the plant selectable kanamycin-resistance gene and the polylinker of pUC18 between the borders (see FIG. 28). Plasmid pCIB4 DNA was digested with endonuclease HindIII, followed by treatment with the large fragment of DNA polymerase to create flush ends, followed by digestion with endonuclease EcoRI. The 2.6-kb fragment containing the chimeric kanamycin-resistance gene and the right border of T-DNA was isolated by agarose gel electrophoresis. Plasmid pCIB5 DNA was digested with endonuclease AatII, treated with T4 DNA polymerase to create flush ends, then cleaved with endonuclease EcoRI. The larger vector fragment was purified by agarose gel electrophoresis, mixed with the pCIB4 fragment, incubated with T4 DNA ligase, and transformed into E. coli strain HB101. The resulting plasmid, pCIB2 (shown in FIG. 24) is a derivative of plasmic pBR322 containing the desired sequences between the two T-DNA borders.

Figure 20:
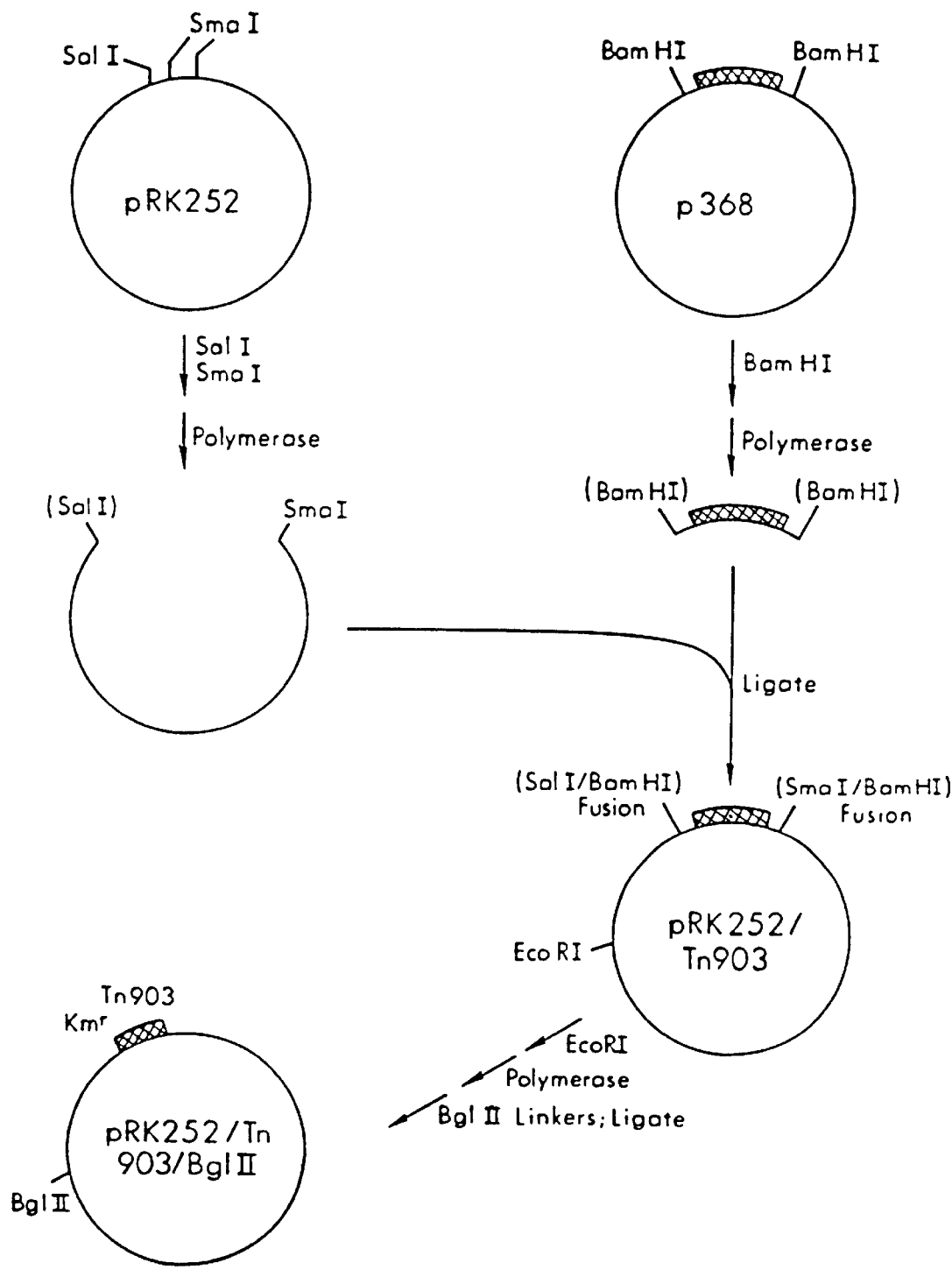
Figure 25:
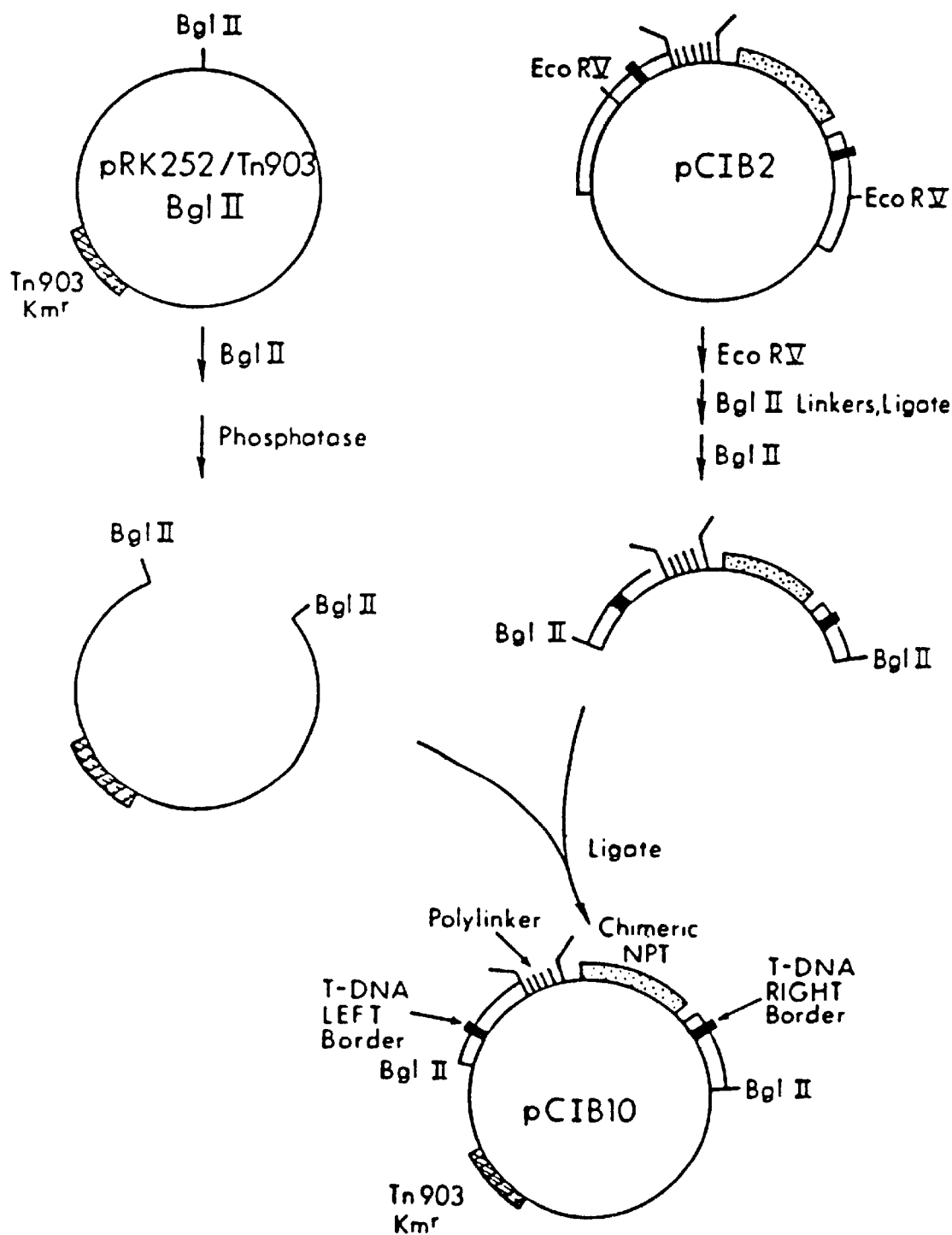

The following steps complete construction of the vector pCIB10, and are shown in FIG. 25. Plasmid pCIB2 DNA was digested with endonuclease EcoRV, and synthetic linkers containing BglII recognition sites are added as described above. After digestion with an excess of BglII endonuclease, the approximately 2.6-kb fragment was isolated after agarose gel electrophoresis. Plasmid pRK252/Tn903/BglII, described above (see FIG. 20) was digested with endonuclease BglII and then treated with phosphatase to prevent recircularization. These two DNA fragments are mixed, incubated with T4 DNA ligase and transformed into E. coli strain HB101. The resulting plasmid is the completed vector, pCIB10.

Figure 26:
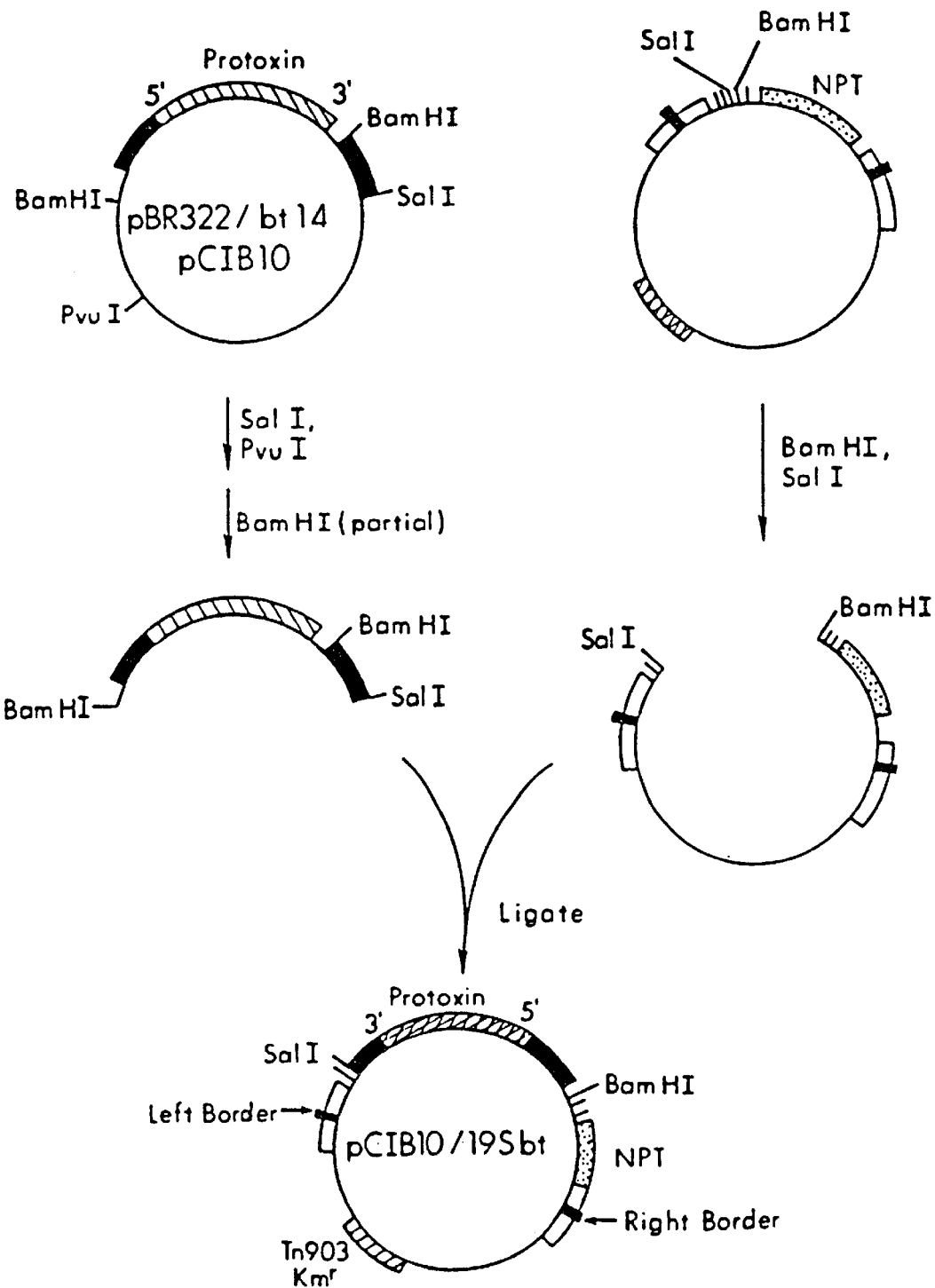

Insertion of the chimeric protoxin gene into vector pCIB10 is by the steps shown in FIG. 26. Plasmid pBR322/btl4 DNA was digested with endonucleases PvuI and SalI, and then partially digested with endonuclease BamHI. A BamHI-SalI fragment approximately 4.2 kb in size, containing the chimeric gene, was isolated following agarose gel electrophoresis, and mixed with plasmid pCIB10 DNA which had been digested with endonucleases BamHI and SalI. After incubation with T4 DNA ligase and transformation into E. coli strain HB101, plasmid shown in FIG. 26 and contained the chimeric protoxin gene in the plasmid vector pCIB10.

In order to transfer plasmid pCIB10/19Sbt from E. coli HB101 to Agrobacterium, an intermediate E. coli host strain S17-1 was used. This strain, obtainable from Agrigenetics. Research Corp., Boulder, Co. contains mobilization functions that transfer plasmid pCIB10 directly to Agrobacterium via conjugation, thus avoiding the necessity to transform naked plasmid DNA directly into Agrobacterium [reference for strain S17-1 is Simon et al., "Molecular Genetics of the Bacteria-Plant Interaction", A Puhler, ed., Springer Verlag, Berlin, pages 98–106 (1983) incorporated herein by reference]. First, plasmid pCIB10/19Sbt DNA is introduced into calcium chloride-treated S17-1 cells. Next, cultures of transformed S17–1 cells and *Agrobacterium tumefaciens* strain LBA4404 [Ooms et al., *Gene* 14 33–50 (1981) incorporated herein by reference] were mixed and mated on an N agar (Difco) plate overnight at room temperature. A loopful of the resulting bacteria are streaked onto AB minimal media [Chilton et al., *Proc. Natl. Acad. Sci. USA* 77 7347–7351 (1974) incorporated herein by reference] plated with 50 μg/ml kanamycin and incubated at 28° C. Colonies were restreaked onto the same media, then restreaked onto NB agar plates. Slow-growing colonies were picked, restreaked onto AB minimal media with kanamycin and single colonies isolated. This procedure selects for Agrobacteria containing the pCIB10/19SBt plasmid.

Figure 27:
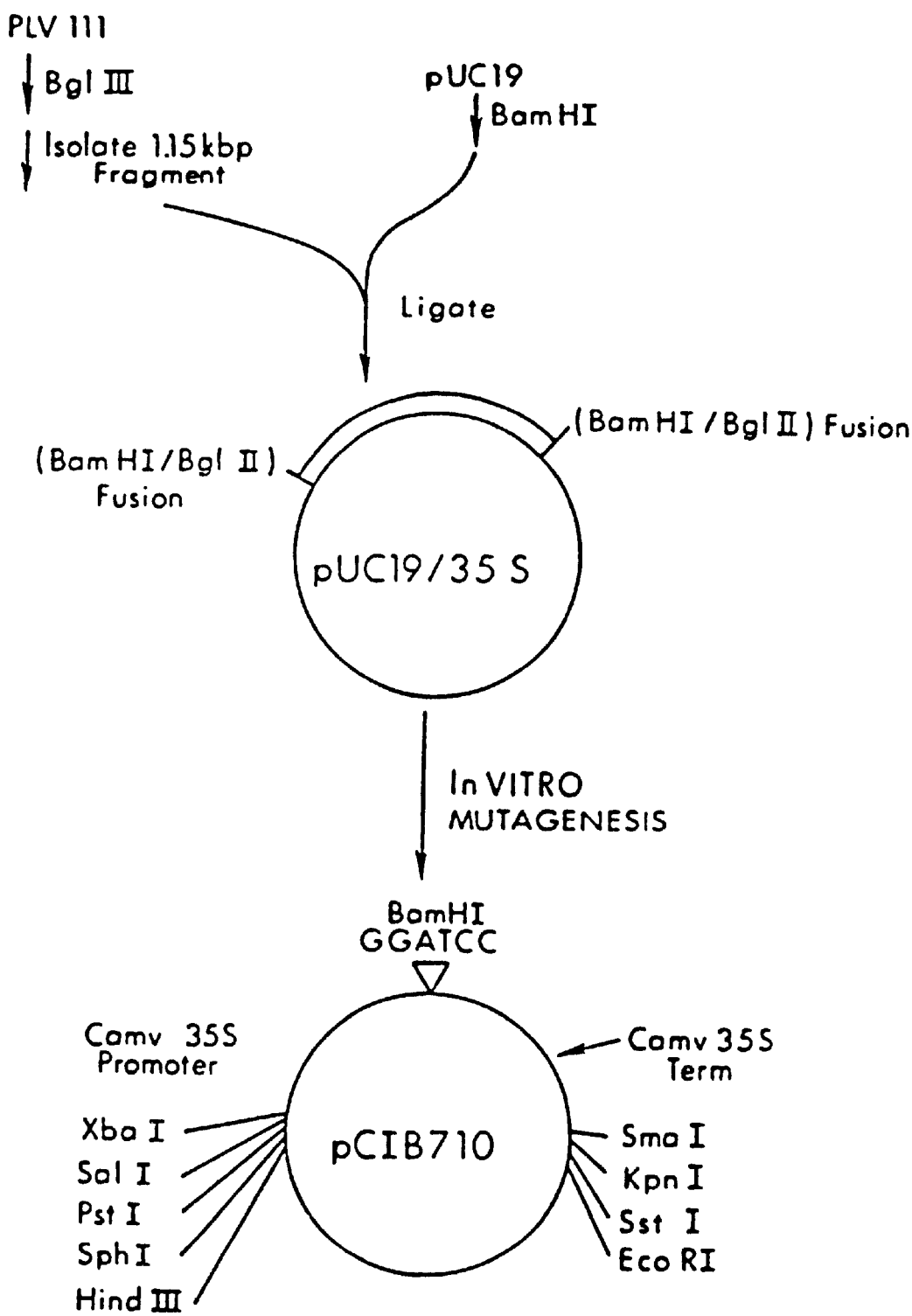

Construction of a *Bacillus thuringiensis* protoxin chimeric gene with the CaMV 35S promoter was achieved by construction of a CaMV 35S Promoter Cassette Plasmid pCIB710 was constructed as shown in FIG. 27. This plasmid contained CaMV promoter and transcription termination sequences for the 35S RNA transcript [Covey et al., *Nucl. Acids Res.* 9 6735–6747 (1981) incorporated herein by reference]. A 1149-bp BglII restriction fragment of CaMV DNA [Hohn et al. In: Current Topics in Microbiology and Immunology 96 194–220 and Appendices A to G (1982) incorporated herein by reference] was isolated from plasmid pLVlll (obtained from Dr. S. Howell Univ. California-San Diego; alternatively, the fragment can be isolated directly from CaMV DNA) by preparative agarose gel electrophoresis as described earlier and mixed with BamHI-cleaved plasmid pUC19 DNA, treated with T4 DNA ligase, and transformed into *E. coli*. The BamHI restriction site in the resulting plasmid has been destroyed by ligation of the BglII cohesive ends to the BamHI cohesive ends. The resulting plasmid, called pUC19/35S, was then used in oligonucleotide-directed in vitro mutagenesis to insert the BamHI recognition sequence GGATCC immediately following CaMV nucleotide 7483 in the Hohn reference. The resulting plasmid, pCIB710, contains the CaMV 35S promotor region and transcription termination region separated by a BamHI restriction site. DNA sequences inserted into this BamHI site will be expressed in plants by the CaMV transcription regulation sequences. pCIB710 does not contain any ATG translation initiation codons between the start of transcription and the BamHI site.

Insertion of the CaMV-35S promoter/Terminator Cassette into pCIB10 occurred by the steps outlined in FIG. 28. Plasmids pCIB10 and pCIB710 DNAs were digested with EcoRI and SalI, mixed and ligated. The resulting plasmid, pCIB10/710 has the CaMV 35S promoter/terminator cassette inserted into the plant transformation vector pCIB10. The CaMV 35S sequences are between the T-DNA borders in pCIB$_{10}$, and thus will be inserted into the plant genome in plant transformation.

Figure 29:
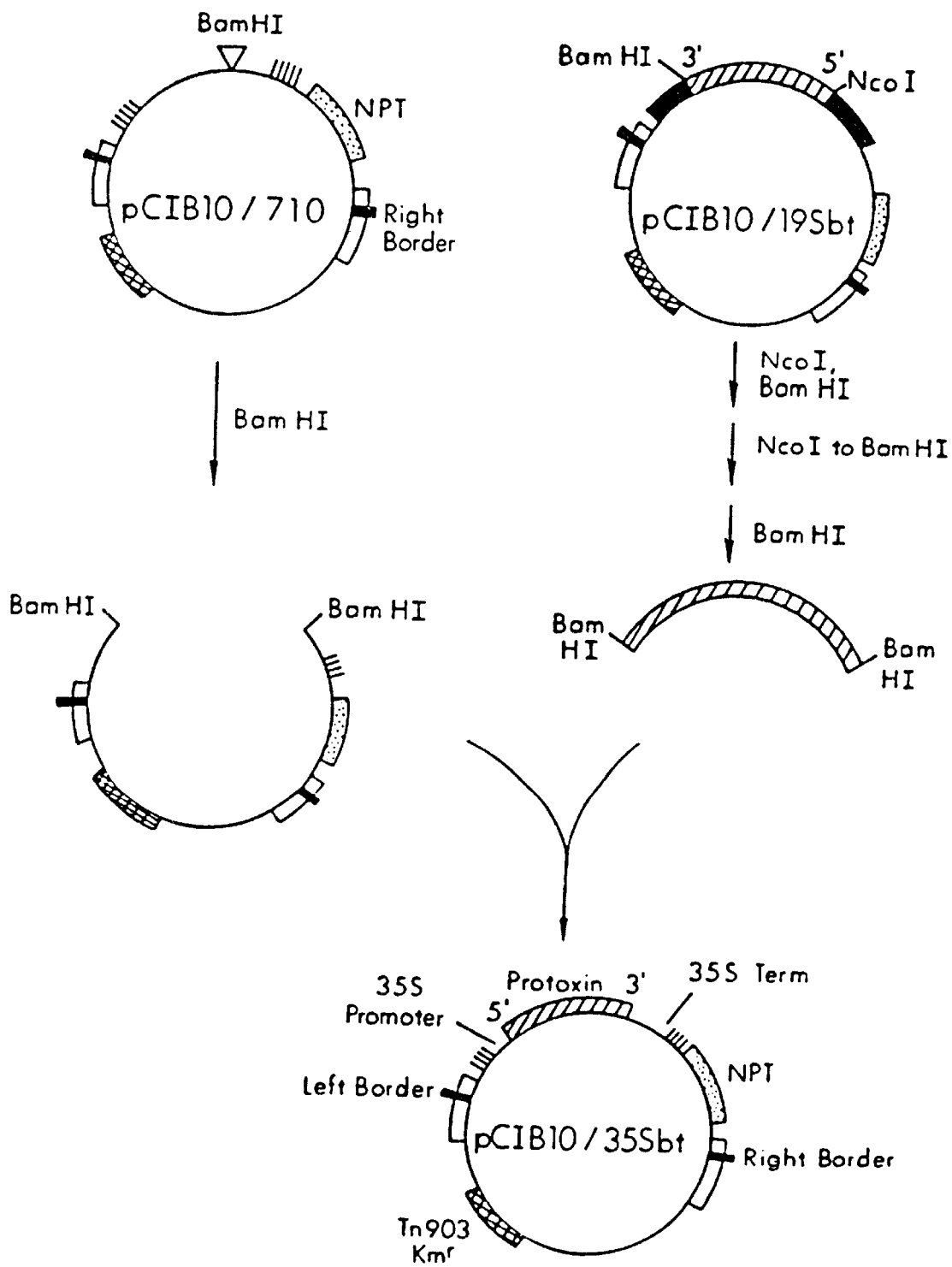
Figure 30:
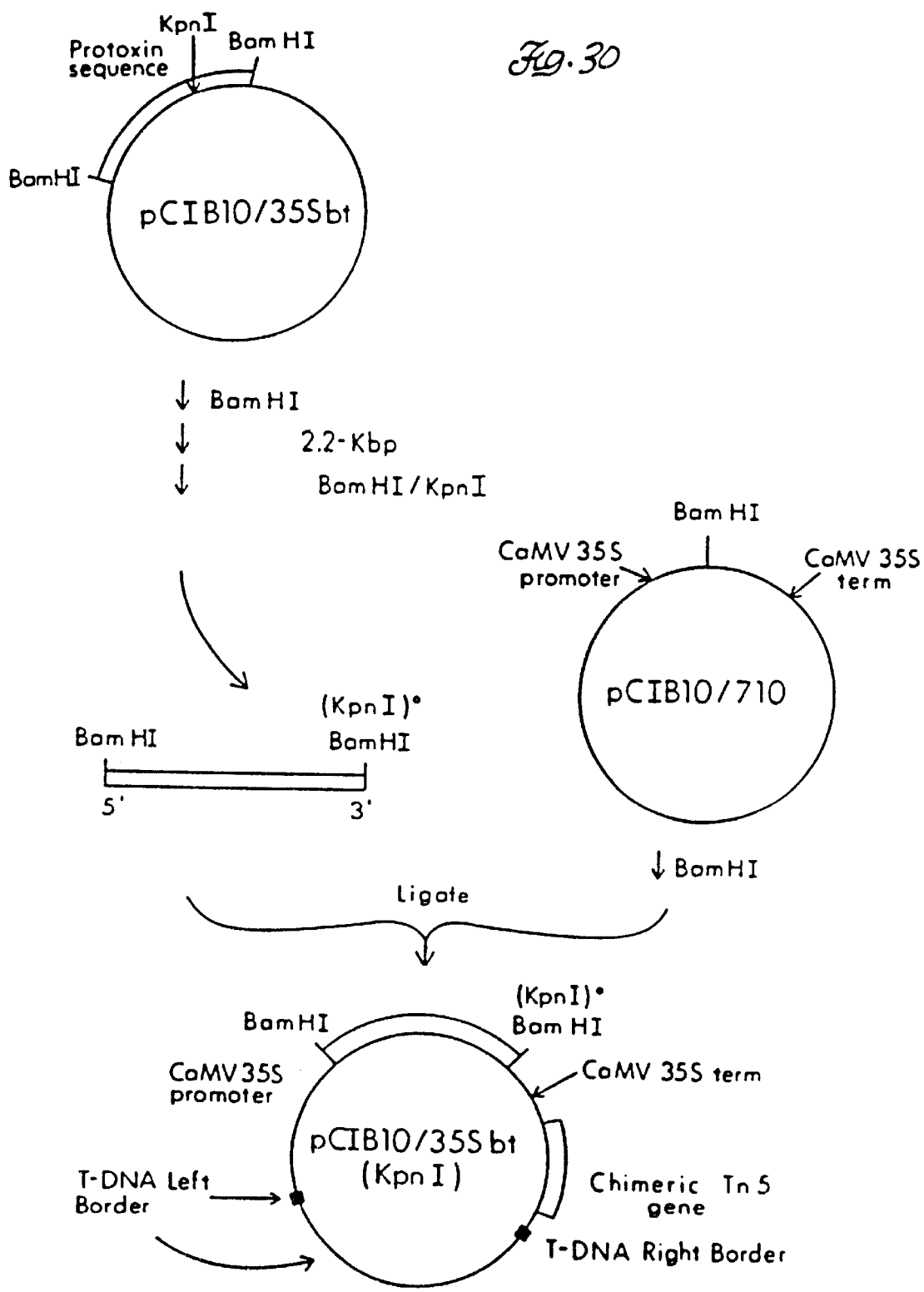
Figure 31:
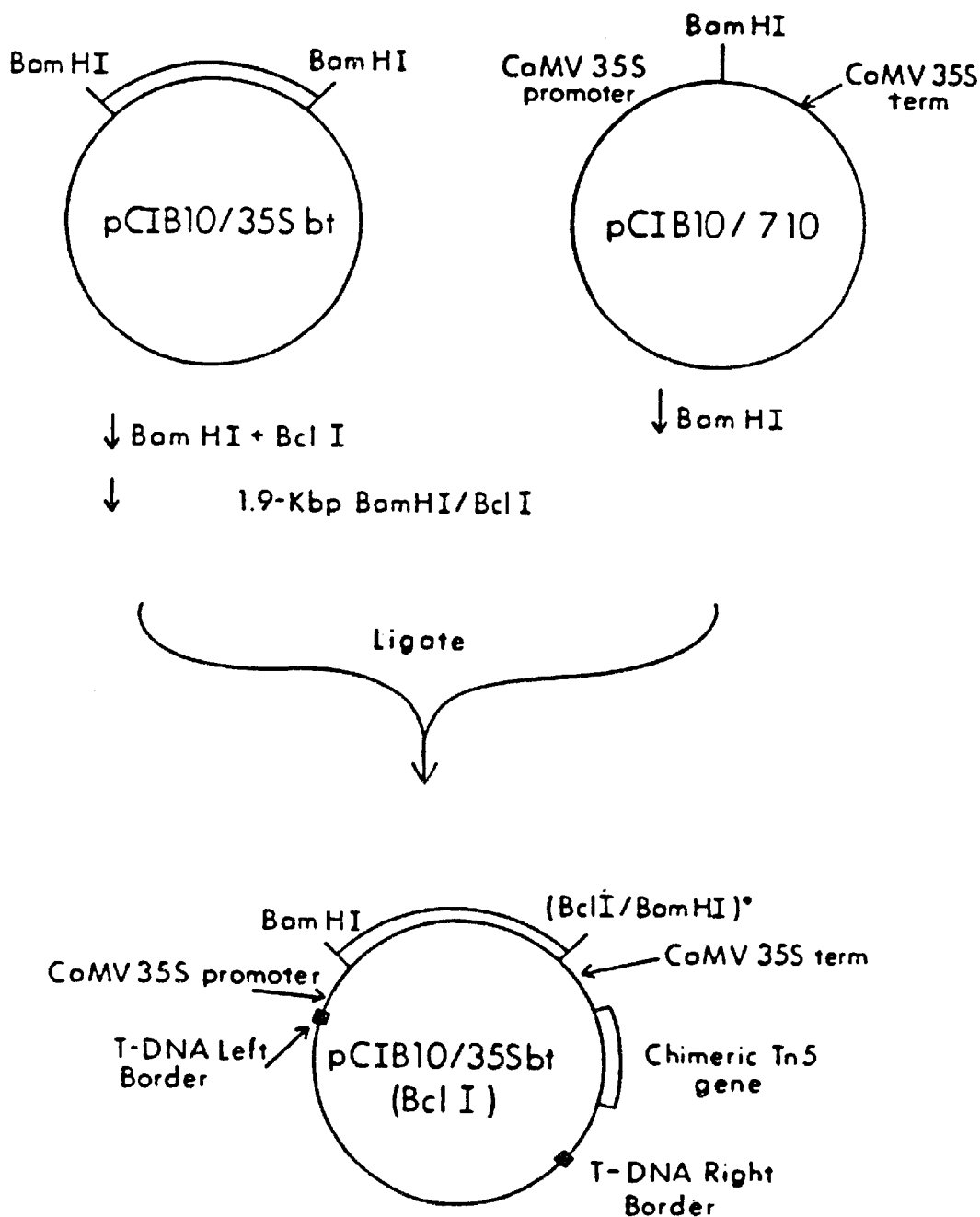
Figure 32:
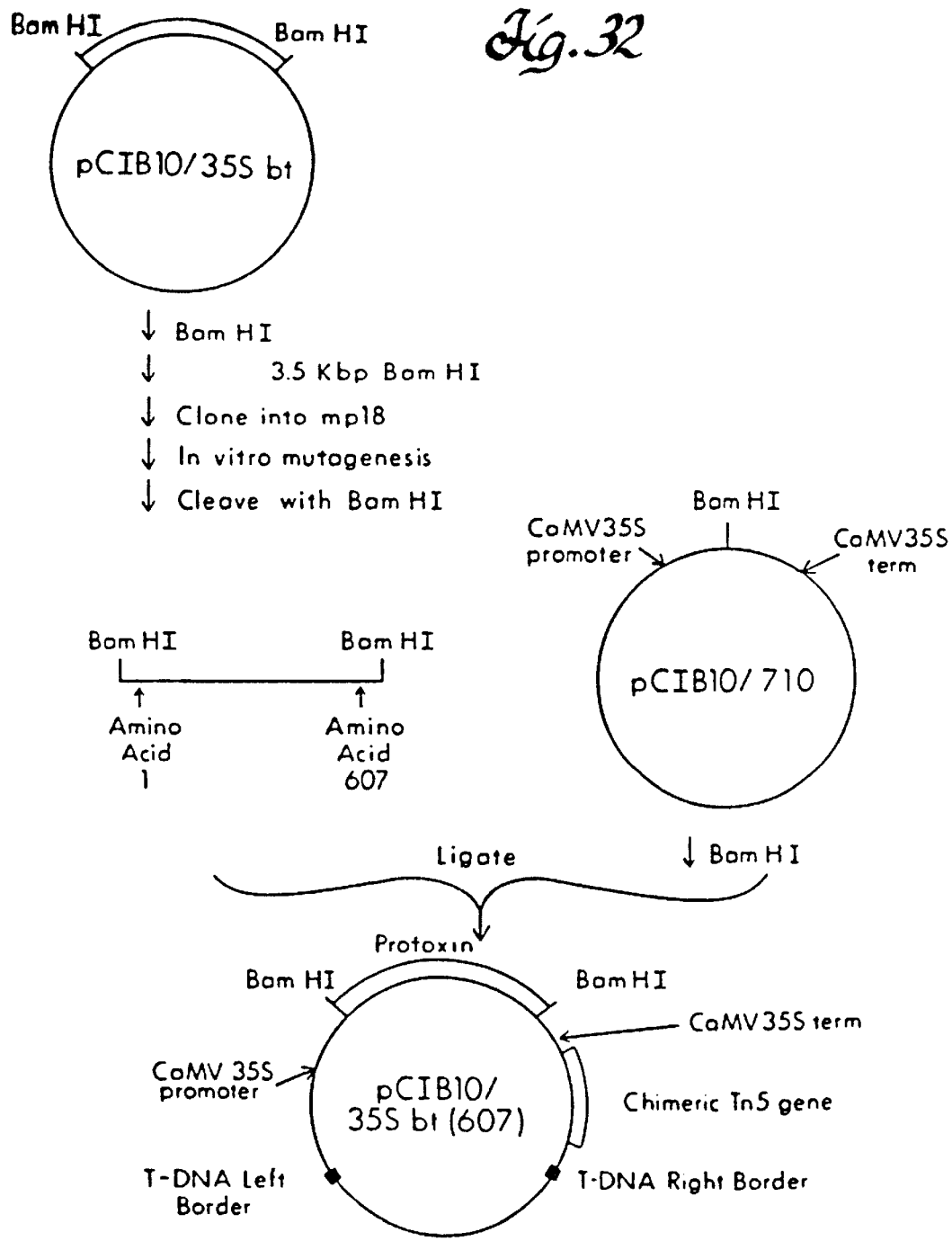

Insertion of the *Bacillus thuringiensis* protoxin gene into pCIB10/710 occurred by the steps outlined in FIG. 29. As a source of the protoxin gene, plasmid pCIB10/19Sbt was digested with BamHI and NcoI, and the 3.6-kb fragment containing the protoxin gene was isolated by preparative gel electrophoresis. The fragment was then mixed with synthetic NcoI-BamHI adapter with the sequence 5' -CATGGCCGGATCCGGC-3', then digested with BamHI. This step creates BamHI cohesive ends at both ends of the protoxin fragment. This fragment was then inserted into BamHI-cleaved pCIB10/710. The resulting plasmid, pCIB10/35Sbt, shown in FIG. 29, contains the protoxin gene between the CaMV 35S promoter and transcription termination sequences.

Transfer of the plasmid pCIB10/35Sbt into *Agrobacterium tumefaciens* strain LBA4404 was as described above.

Construction of a deleted *Bacillus thuringiensis* protoxin gene containing approximately 725 amino acids, and construction of a chimeric gene containing this deleted gene with the CaMV 35S promoter was made by removing the COOH-terminal portion of the gene by cleaving at the KpnI restriction endonuclease site at position 2325 in the sequence shown in SEQ ID NO: 1. Plasmid pCIB10/35Sbt (FIG. 29) was digested with BamHI and KpnI, and the approximately 2.2-kb BamHI/KpnI fragment containing the deleted protoxin gene isolated by preparative agarose gel electrophoresis. To convert the KpnI site at the 3' end to a BamHI site, the fragment was mixed with a KpnI/BamHI adapter oligonucleotide and ligated. This fragment is then mixed with BamHI-cleaved pCIB10/710 (FIG. 28).

A deleted protoxin gene containing approximately 645 amino acids was made by removing the COOH-terminal portion of the gene by cleaving at the BclI restriction endonuclease site at position 2090 in the sequence shown in SEQ ID NO: 1. Plasmid. pCIB10/35Sbt (FIG. 29) was digested with BamHI and BclI, and the approximately 1.9-kb BamHI/BclI fragment containing the deleted protoxin gene isolated by preparative agarose gel electrophoresis. Since BclI creates a cohesive end compatible with BamHI, no further manipulation is required prior to ligating this fragment into BamHI-cleaved pCIB10/710 (FIG. 28). The resulting plasmid, which has the structure pCIB10/35Sbt(BclI) shown in FIG. 31 was selected on kanamycin.

The resulting transformants, designated pCIB10/35Sbt (KpnI) and shown in FIG. 30, contain the deleted protoxin gene of approximately 725 amino acids. These transformants are selected on kanamycin.

A deleted protoxin gene was made by introducing a BamHI cleavage site (GGATCC). This is done by cloning the BamHI fragment containing the protoxin sequence from pCIB10/35Sbt into mp18, and using standard oligonucleotide mutagenesis. procedures described above. After mutagenesis, double-stranded replicative form DNA is prepared from the M13 clone, which is then digested with BamHI. The approximately 1.9-kb fragment containing the deleted protoxin gene is inserted into BamHI-cleaved pCIB10/710. The resulting plasmid, which the structure pCIB10/35Sbt(607) shown in FIG. 32 is selected for on kanamycin.

The pCIB10/Sbt 607 was used. Transformation was accomplished as detailed in Example 7 with the change that the 1 ml aliquots were plated immediately on medium containing selective antibiotics. This selection medium contained kanamycin (50 μg/ml) or G418 (25 μg/ml). Expression of the NPT chimeric gene in both transformed plant tissue allows the selection of this tissue on either antibiotic.

In 2–4 weeks, transformed tissue became apparent on the selection plates. Plant material was selected on kanamycin or G418. Plant tissue (either individual embryos or callus) was then extracted with buffer and assayed for expression of the BT gene product by ELISA assay. The conditions of extraction are as follows: per 100 mg of tissue, homogenize in 0.1 ml of extraction buffer containing 50 mM $NaCO_3$ (pH 9.5), 0.050% Triton, 0.05% Tween, 100 mM NaCl, 10 mM EDTA, 1 mM leupeptine, and 1 mM PMSF. The leupeptine and PMSF are added immediately prior to use from 100× stock solutions. The tissue was ground with a motor driven pestle. After extraction, 2 M Tris pH 7 was added to adjust pH to 8.0–8.5 then centrifuged at 12,000 RPM in a Beckman microfuge 12 (10 minutes at 4° C.), and the supernatant saved for enzyme linked immunosorbent assay ("ELISA"). ELISA techniques are a general tool [described by Clark et al., *Methods in Enzymology* 118 742–766 (1986) incorporated by reference].

An ELISA for the Bt toxin-was developed using standard procedures and used to analyze transgenic plant material for expression of Bt sequences. For this procedure, an ELISA plate is pretreated with ethanol and affinity-purified rabbit anti-Bt antiserum (50 μl) at a concentration of 3 μg/ml in borate-buffered saline (see below) is added to the plate. This was allowed to incubate overnight at 4° C. Antiserum was produced in response to immunizing rabbits with gradient-purified Bt crystals [Ang et al., *Appl. Environ. Microbiol*. 36 625–626 (1978)), incorporated herein by reference] solubilized with sodium dodecyl sulfate and washed with ELISA Wash Buffer (see below). It was then treated for 1 hour at room temperature with Blocking Buffer (see below) washed with ELISA Wash Buffer. Plant extract was added in an amount to give 50 μg of protein (this is typically about 5 microliters of extract). Leaf extraction buffer as protein is determined by the Bradford method [Bradford *Anal. Biochem.* 72 248 (1976) incorporated herein by reference] using a commercially available kit obtained from Bio-Rad, Richmond, Calif. If dilution of the leaf extract is necessary, ELISA Diluent (see below)] is used. Allow this to incubate overnight at 4° C. After a wash with ELISA Wash Buffer, 50 μl affinity-purified goat anti-Bt antiserum is added at a concentration of 3 μg/ml protein in ELISA Diluent. This is allowed to incubate for 1 hour at 37° C., then washed with ELISA Wash Buffer. 50 μl rabbit anti-goat antibody bound to alkaline phosphatase [commercially available from Sigma Chemicals, St. Louis, Mo.] is diluted 1:500 in ELISA Diluent and allowed to incubate for 1 hour at 37° C., then washed with ELISA Wash Buffer. 50 microliters substrate [0.6 mg/ml p-nitrophenyl phosphate in ELISA Substrate Buffer (see below) are added and incubated for 30 minutes at room temperature. Reaction is terminated by adding 50 μl of 3 M NaOH. Absorbance is read at 405 nm in modified ELISA reader [Hewlett Packard, Stanford, Calif.]

Plant tissue transformed with the pCIB10/35SBt(BclI) when assayed using this ELISA procedure showed a positive reaction, indicating expression of the Bt gene.

EPBS (ELISA Phosphate Buffered Saline)
10 mM NaPhosphate: $Na_2HPO_4$ 4.68 grams/4 liters
  $NaH_2PO_4.H20$ 0.976 grams/4 liters
140 mM NaCl NaCl 32.7 grams/4 liters
pH should be approximately 7.4
Borate Buffered Saline
100 mM Boric acid
25 mM Na Borate
75 mM NaCl
  Adjust pH to 8.4–8.5 with HCl or NaOH as needed.
ELISA Blocking Buffer
In EPBS,
1% BSA
0.02% Na azide
ELISA Wash Buffer
10 mM Tris-HCl pH 8.0
0.05% Tween 20
0.02% Na Azide
2.5 M TRIS
ELISA Diluent
In EPBS:
0.05% Tween 20
1% BSA
0.02% Na Azide
ELISA Substrate Buffer
In 500 ml,
48 ml Diethanolamine,
24.5 mg $MgCl_2$;
adjust to pH 9.8 with HCl.
ELISA Substrate
15 mg p-nitrophenyl phosphate in 25 ml Substrate Buffer.

For bioassays, cell suspensions from antibiotic-resistant cell cultures obtained from transformations with these A grobacierin were initiated. Suspensions were grown in medium supplemented with G418 (25 mg/l), and subcultured into fresh antibiotic-containing medium on 7–10 day intervals. Samples of these cultures are used in bioassays to test for toxicity to lepidopterous insects. Twenty ml aliquots of these cultures were allowed to settle (cell volume is about 3–4 ml), and resuspended in medium lacking antibiotics. Suspensions were then allowed to grow for an additional two days in this medium to deplete the cells of any residual antibiotic. Two circles of wet Whatman 2.3 cm filter paper were placed in the bottom of a ¾ oz portion cup. A layer of transformed suspension culture cells 0.2 cm deep was placed onto the filter paper disk. A newly-hatched *Manduca sexta* or *Ileliothis virescens* larva was placed into each portion cup. Controls were made up of larvae fed on non-transformed suspension culture cells. Discs were replenished on 2-day intervals or as needed. Manduca larvae generally require more plant material. The growth rate and mortality of the lavae feeding on transformed cells compared with the growth rate of larvae feeding on untransformed cells is scored after 5 days, and clearly affirms the toxicity of the BT gene product in transformed cotton cells.

EXAMPLE 18

Transformation of Cotton Plants

Plant segments were placed in a medium containing an Agrobacterium vector containing a selectable marker such as resistance to an antibiotic, kanamycin, for 1 minute to 24 hours to transfer the gene to the cells of the explant. The explants were then removed and placed on agar-solidified callus growth medium (MS medium supplemented with 2 mg/l NAA and incubated for 15 to 200 hours at 30° C., on a 16:8 hour light:dark regime.

After incubation, the explants were transferred to the same medium supplemented with 200 mg/l cefotaxime to kill any Agrobacterium present in the culture. At the end of 4–5 weeks of culture on fresh medium, the developing callus was separated from the remainder of the primary explant tissue and transferred to MS medium containing 2 mg/l NAA, 200 mg/ml cefotaxime and 50 mg/l kanamycin sulfate. Transformed primary callus was selected.

EXAMPLE 19

Transformation of Cotton Embryos

Embryos were placed in a medium containing an Agrobacterium vector containing resistance to kanamycin for 1 minute to 24 hours to transfer the gene to the cells of the embryos. The embryos were then removed and placed on agar-solidified callus growth medium (MS medium supplemented with 2 mg/l NAA and incubated for 15 to 200 hours at 30° C., on a 16:8 hour light:dark regime.

After incubation, the embryos were transferred to the same medium supplemented with 200 mg/l cefotaxime. At the end of 4–5 weeks of culture on fresh medium, the embryos were transferred to MS medium containing 2 mg/l NAA, 200 mg/ml cefotaxime and 50 mg/l kanamycin sulfate. Transformed embryos were selected.

EXAMPLE 20

Transformation of Cotton Callus

Callus was placed in a medium containing an Agrobacterium vector containing resistance to kanamycin for 1 minute to 24 hours to transfer the gene to the cells of the embryos. The callus was then removed and placed on agar-solidified callus growth medium (MS medium supplemented with 2 mg/l NAA and incubated for 15 to 200 hours at 30° C., on a 16:8 hour light:dark regime.

After incubation, the callus is transferred to the same medium supplemented with 200 mg/l cefotaxime. At the end of 4–5 weeks of culture on fresh medium, the developing callus was transferred to MS medium containing 2 mg/l NAA, 200 mg/ml cefotaxime and 50 mg/l kanamycin sulfate. Transformed callus was selected.

EXAMPLE 21

The method of Examples 18, 19 and 20 were used to transform plants, embryos and callus of the following cotton varieties: SJ2, SJ5, SJ-C1, GC510, B1644, B1654-26, B1654-43, B1810, B2724, COKER 315, STONEVILLE 506, CHEMBRED B2, CHEMBRED C4 and SIOKRA.

EXAMPLE 22

The method of Examples 19 and 20 were used to transform embryos and callus of the following cotton varieties: Acala Royale, FC 3027 and SICALA.

EXAMPLE 23

The method of Example 20 was used to transform callus of the following cotton varieties: GC356, Acala Maxxa, Acala Prema, B4894, DP50, DP61, DP90 and ORO BLANCO PIMA.

EXAMPLE 24

The method of Example 18 was repeated except kanamycin was used at a concentration of 5 mg/l.

EXAMPLE 25

The method of Example 18 was repeated except kanamycin was added when the explants were transferred to the MS medium supplemented with 200 mg/l cefotamine.

EXAMPLE 26

The method of Example 18 was repeated except G418 at a concentration of 25 mg/l was used in place of kanamycin.

The transformations are summarized in the Table below.

|  | VARIETY | TRANSFORMATION | | |
|---|---|---|---|---|
|  |  | $C^1$ | $E^2$ | $P^3$ |
| Example 18 | Acala SJ2 | + | + | + |
| Example 18 | Acala SJ5 | + | + | + |
| Example 18 | Acala SJ-C1 | + | + | + |
| Example 20 | Acala GC356 | + | − | − |
| Example 18 | Acala CG510 | + | + | + |
| Example 18 | Acala B1644 | + | + | + |
| Example 18 | Acala B1654-26 | + | + | + |
| Example 18 | Acala B1654-43 | + | + | + |
| Example 19 | Acala Royale | + | + | − |
| Example 20 | Acala Maxxa | + | − | − |
| Example 21 | Acala Prema | + | − | − |
| Example 18 | Acala B1810 | + | + | + |
| Example 18 | Acala B2724 | + | + | + |
| Example 20 | Acala B4894 | + | − | − |
| Example 18 | COKER 315 | + | + | + |
| Example 18 | STONEVILLE 506 | + | + | + |
| Example 20 | DP50 | + | − | − |
| Example 20 | DP61 | + | − | − |
| Example 20 | DP90 | + | − | − |
| Example 19 | FC 3027 | + | + | − |
| Example 18 | CHEMBRED B2 | + | + | + |
| Example 18 | CHEMBRED C4 | + | + | + |
| Example 18 | SIOKRA | + | + | + |
| Example 19 | SICALA | + | + | − |
| Example 20 | ORC BLANCO PIMA | + | − | − |

[1] Callus
[2] Embryos
[3] Plants
[4] + indicates that transformation of the tissue was performed
[5] + indicates that transformation of the tissue was not obtained

EXAMPLE 27

*Heliothis virescens* eggs laid on sheets of cheesecloth are obtained from the Tobacco Insect Control Laboratory at North Carolina State University, Raleigh, N.C. The cheesecloth sheets are transferred to a large covered glass beaker and incubated at 29° C. with wet paper towels to maintain humidity. The eggs hatched within three days. As soon as possible after hatching, the larvae (one larva per cup) are transferred to covered ¾ oz. plastic cups. Each cup contains cotton leaf discs. Larvae are transferred using a fine bristle paint brush.

Leaf discs one centimeter in diameter are punched from leaves of cotton plants and placed on a circle of wet filter paper in the cup with the larva. At least 6–10 leaf discs, representing both young and old leaves, are tested from each plant. Leaf discs are replaced at two-day intervals, or as necessary to feed the larvae. Growth rates [size or combined weight of all replica worms] and mortality of larvae feeding on leaves of transformed plants are compared with those of larva feeding on untransformed cotton leaves.

Larvae feeding on discs of cotton transformed with pCIB10/35SB5(BclI) show a decrease in growth rate and increase in mortality compared with controls.

It was observed that a certain number of our regenerated plants (5–10%) appeared to have acquired genetically heritable phenotypic variations as a consequence of the process of regeneration. This variation is known as somaclonal variation. The following examples illustrate how somaclonal variation as a consequence of our regeneration procedure has been used to introduce commercially useful new traits into cotton varieties.

EXAMPLE 28

Cotton Regenerants Tolerant to Fungal Pathogens

The procedure of Example 1 was followed, and regenerated cotton plants obtained of the variety SJ5 and SJ4 were hardened and placed in the soil. These plants were self-pollinated and the seed, representing the F1 generation, collected.

Figure 33:
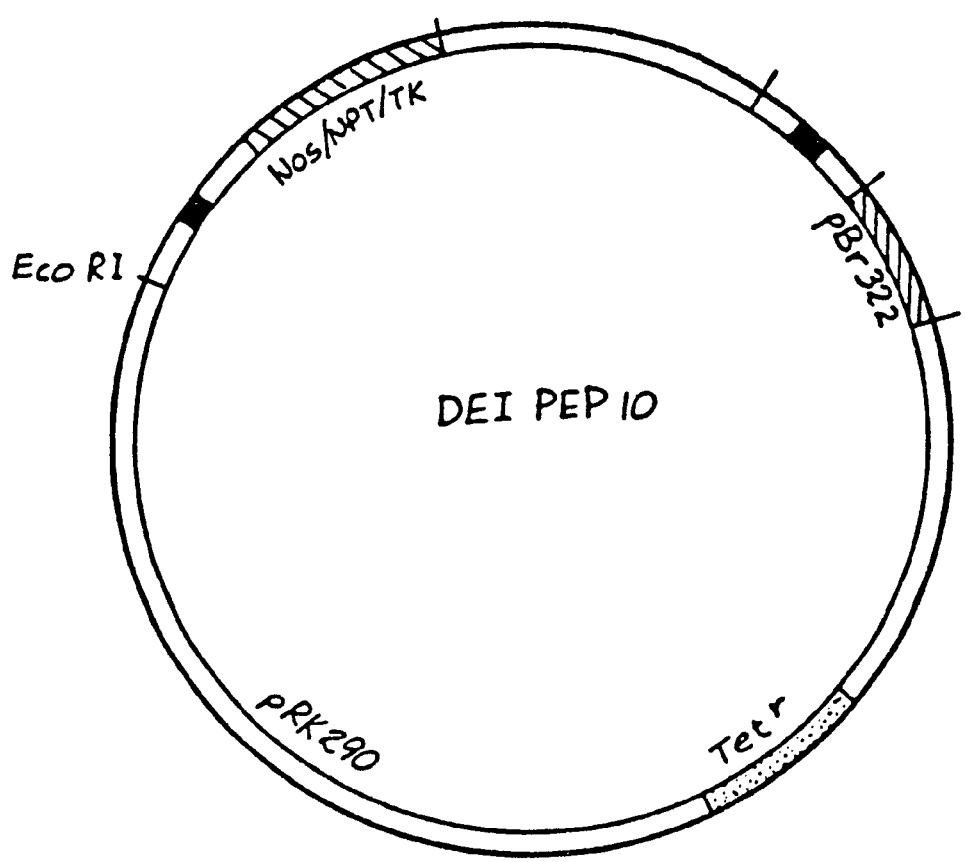
Figure 34:
Figure 35:

To obtain regenerants (somaclonal variants) more tolerant to Verticillium, the f1 generation was planted in a Verticillium infested field for progeny row analysis. Seed of the varieties SJ4 and SJ5 were planted in the field as controls. Somaclonal variants more tolerant than the parental varieties to the Verticillium fungus were identified in a few of the progeny rows (5%) by assessing overall plant vigor, yield, and the absence of foliar symptoms associated with the disease. FIG. 33 shows the progeny rows of regenerants planted in a Verticillium infested field. FIG. 34 shows a Verticillium tolerant somaclonal variant of variety SJ4. This improvement in tolerance to the fungal pathogen was found to be genetically stable and passed on to subsequent generations.

EXAMPLE 29

Cotton Regenerants With Altered Growth Habits

The procedure of Example 28 was followed except that, rather than planting in disease-infested soil, the F1 generation was planted in a cotton breeding nursery. The overall growth habit of the F1 regenerated progeny was compared to that of the control varieties. Somaclonal variants were identified which were more uniform in growth habit and shorter in stature than the parental variety. One SJ5 regenerant, identified in our trials as Phy 6, was 20% shorter in stature than the parental variety. This kind of growth habit is desirable in cotton grown under narrow row (30" row spacing) cultural conditions. These traits were found to be genetically stable and passed on to subsequent generations.

EXAMPLE 30

Cotton Regenerants With Improved Fiber Traits

The procedure of Example 28 was followed except that the F1 progeny of regenerants were planted in a cotton breeding nursery and allowed to set fruit. When the bolls were mature, the cotton was harvested and subjected to an analysis of several fiber quality traits including length, uniformity, tensile strength, elasticity, and micronaire. Somaclonal variants were identified which were improved significantly over the parental variety in one or more of these traits. Representative data from F2 progeny (cell pollination of the F1) are included in the following Table 1. Values marked with an asterisk represent improvements in SJ5 regenerants which are statistically significant and have been found to breed true in subsequent generations.

TABLE 1

| | Fiber Properties | | | | |
|---|---|---|---|---|---|
| Variety or strain | Length | Uniformity Index | Tensile Strength | Elasticity | Micronaire |
| SJ5 | 1.13 | 48.7 | 24.7 | 6.8 | 4.27 |
| 3SP16 | 1.27* | 51.2 | 24.6 | 8.0* | 4.10* |
| 3SP20 | 1.28* | 53.1* | 23.1 | 7.6* | 4.13* |
| 5SP10 | 1.11 | 53.2* | 25.7* | 6.2 | 4.55 |
| 5SP17 | 1.18 | 51.7 | 26.7* | 7.1 | 4.43 |

EXAMPLE 31

Cotton Regenerants With Improved Yield

The procedure of Example 28 was followed except that the F1 progeny of regenerants of the variety SJ4 were planted in replicated yield trials along with nonregenerated controls. One variant, which exhibited a more uniform growth habit and more vigorous growth habit, yielded 4% more cotton than the parental variety in the same trial. The data are given in Table 2 below.

TABLE 2

| Variety or Strain | Ave Yield per plot (lb) | Ave Yield lbs/Acre | % Increase |
|---|---|---|---|
| SJ4 Control | 28.0 | 3049 | |
| Phy 4 | 29.1 | 3169 | 4%* |

*This difference was significant at the 95% confidence level.

A 4% increase in yield would represent a return of almost $20 per acre to the average cotton grower in California, where over one million acres of cotton are grown annually.

EXAMPLE 32

Cotton Regenerants Tolerant to a Herbicide (Kanamycin)

Suspension cultures of the cotton variety B1644 were developed according to the method of Example 5. Suspension cultures were then plated onto an agar medium as described in Example 6, but supplemented with the herbicide (antibiotic) kanamycin (25 mg/l). Most of the cells in the population died, but a few (1 to 5%) were tolerant and survived. These were selectively subcultured onto agar-solidified media supplemented with increasing concentrations of kanamycin, until the final concentration reached 50 mg/l. Embryos were then developed from this callus, and those resistant embryos were germinated into kanamycin resistant plants.

What is claimed is:

1. A method for producing a transformed cotton plant comprising the steps of:
   providing a cotton explant from a source selected from the group consisting of cotyledon, immature zygotic embryos and mixtures thereof;
   incubating the cotton explant in the presence of a vector comprising DNA encoding a selectable marker to produce a treated explant;
   growing the treated explant to produce callus;
   selecting transformed embryogenic callus; and
   regenerating a transformed cotton plant therefrom.

2. The method as recited in claim 1, wherein the vector is derived from an Agrobacterium plasmid.

3. The method as recited in claim 1, further comprising the step of incubating the treated explant in a callus growth medium toxic to Agrobacterium but non-toxic to the explant or callus.

4. The method as recited in claim 1, wherein the treated explant is grown under illumination cycles of 16 hours of light and 8 hours of dark.

5. The method as recited in claim 4, wherein the treated explant is grown in a light intensity of 2,000 to 4,000 lux during the hours of light of the illumination cycles.

6. The method as recited in claim 4, wherein the treated explant is grown in a light intensity of 3,000 to 4,000 lux during the hours of light of the illumination cycles.

7. The method as recited in claim 1, wherein the treated explant is grown at a temperature of 25° C. to 35° C.

8. The method as recited in claim 1, wherein the treated explant is grown at a temperature of 30° C.

9. The method as recited in claim 1, wherein the treated explant is grown for about 3 to 4 weeks to produce callus.

10. The method as recited in claim 1, wherein treated explant is grown in a sucrose-free, first callus growth medium supplemented with thiamine, kinetin, inositol and naphthaleneacetic acid and glucose as the primary carbon source until the secretion of phenolic compounds ceases and callus is formed.

11. The method as recited in claim 1, further comprising the step of, after the secretion of phenolic compounds ceases, transferring the callus to a second callus growth medium for the formation of embryogenic callus.

12. The method as recited in claim 11, wherein sucrose is the primary carbon source in the second callus growth medium.

13. The method as recited in claim 12, wherein the second callus growth medium is supplemented with thiamine, kinetin, inositol and naphthaleneacetic acid.

14. The method as recited in claim 1, further comprising the steps of:
   obtaining a transformed embryo from the transformed embryogenic callus,
   transferring the transformed embryo to an embryo germination medium, and
   culturing the transformed embryo on the embryo germination medium until a plantlet is formed from the transformed embryo.

15. The method as recited in claim 14, wherein the embryo germination medium is supplemented with casein hydrolysate and a source of ammonia.

16. The method as recited in claim 14, wherein the transformed embryo is cultured under illumination cycles of 16 hours of light and 8 hours of dark.

17. The method as recited in claim 16, wherein the transformed embryo is cultured in a light intensity of 2,000 to 4,000 lux during the hours of light of the illumination cycles.

18. The method as recited in claim 16, wherein the transformed embryo is cultured in a light intensity of 3,000 to 4,000 lux during the hours of light of the illumination cycles.

19. The method as recited in claim 14, wherein the transformed embryo is cultured at a temperature of 25° C. to 35° C.

20. The method as recited in claim 14, wherein the transformed embryo is cultured at a temperature of 30° C.

21. The method as recited in claim 14, further comprising the step of culturing the transformed embryo for about 2 to 3 weeks to produce plantlets.

22. The method as recited in claim 14, further comprising the steps of transferring the plantlet to soil and growing the plantlet until the plantlet is sufficiently matured to withstand transfer to a greenhouse or field for growth to final maturity.

23. The method as recited in claim 1, further comprising the steps of:
   sterilizing a cotton seed;
   transferring the seed to a seed germination medium;
   growing the seed in the seed germination medium until a seedling is produced; and
   preparing explants from the seedling.

24. The method as recited in claim 3, wherein the callus growth medium toxic to Agrobacterium comprises cefotaxime.

25. The method as recited in claim 1, wherein the treated explant is grown on a first callus growth medium that is a Murashige and Skoog medium supplemented with naphthaleneacetic acid in an amount of 1 to 10 mg/l.

26. The method as recited in claim 1, wherein the selectable marker confers resistance to a compound toxic to wild type callus.

27. The method as recited in claim 1, wherein the selectable marker is neomycin phosphotransferase.

28. The method as recited in claim 1, wherein the vector further comprises heterologous DNA, in addition to the DNA encoding the selectable marker, wherein the heterologous DNA encodes a protein that, when expressed, confers a desired trait to transformed embryogenic callus or plants derived from transformed enbryogenic callus.

29. The method as recited in claim 28, wherein the heterologous DNA encodes a protein that confers antibiotic resistance.

30. The method as recited in claim 29, wherein the antibiotic resistance is kanamycin resistance or G418 resistance.

31. The method as recited in claim 28, wherein the heterologous DNA encodes neomycin phosphotransferase.

32. The method as recited in claim 28, wherein the heterologous DNA encodes a protein that confers herbicide resistance.

33. The method as recited in claim 32, wherein the herbicide resistance is glyphosate resistance.

34. The method as recited in claim 28, wherein the heterologous DNA comprises a mutant aroA gene.

35. The method as recited in claim 28, wherein the heterologous DNA encodes an altered form of 5-enolpyruvyl shikimate 3-phosphate synthase.

36. The method as recited in claim 1, wherein the transformed callus is selected by growing the transformed callus in a medium supplemented with a compound toxic to non-transformed callus but non-toxic to the transformed callus.

37. The method as recited in claim 36, wherein the transformed callus is selected by growing the callus in a medium supplemented with kanamycin or G418.

38. A method for transforming cotton plant material comprising the steps of:
   providing a cotton explant from a source selected from the group consisting of cotyledon, immature zygotic embryos and mixtures thereof;
   culturing the explant in a sucrose-free first callus growth medium supplemented with thiamine, kinetin, inositol, naphthaleneacetic acid and glucose until secretion of phenolic compounds ceases and undifferentiated callus is formed from the explant;
   culturing the undifferentiated callus in a glucose-free second callus growth medium supplemented with inositol, naphthaleneacetic acid and sucrose until embryogenic callus is formed from the undifferentiated callus;
   incubating the enbryogenic callus in the presence of a plasmid vector derived from an Agrobacterium plasmid comprising DNA encoding a selectable marker to produce treated callus;
   incubating the treated callus in a callus growth medium toxic to Agrobacterium but non-toxic to callus to produce callus; and
   selecting transformed embryogenic callus.

39. The method as recited in claim 38, further comprising the steps of:
   suspending the embryogenic callus in a suspension medium formed of the glucose-free second callus growth medium to form a suspension culture; and
   growing the embryogenic callus in the suspension culture.

40. The method as recited in claim 38, further comprising the steps of:
   obtaining a transformed embryo from the transformed enbryogenic callus;
   transferring the transformed embryo to an embryo germination medium which is a Beasley and Ting's medium containing about 500 mg/l casein hydrolysate and about 1200 mg/l ammonium nitrate; and culturing the transformed embryo on the embryo germination medium until a transformed plantlet is formed from the transformed embryo.

41. The method as recited in claim 15, wherein said germination medium comprises a Beasley and Ting's medium containing about 500 mg/l casein hydrolysate and about 1200 mg/l ammonium nitrate.

42. The method as recited in claim 40, wherein said germination medium comprises a Beasley and Ting's medium containing about 500 mg/l casein hydrolysate and about 1200 mg/l ammonium nitrate.

43. A method for producing a transformed cotton plant comprising the step of:

providing an embryogenic cotton callus in or on a medium;

incubating the embryogenic cotton callus in the presence of an Agrobacterium comprising a vector comprising DNA encoding a selectable marker to produce a treated embryogenic cotton callus;

selecting transformed embryogenic cotton callus; and regenerating a transformed cotton plant therefrom.

44. The method as recited in claim 43, wherein the selectable marker confers resistance to a compound toxic to non-transformed callus.

45. The method as recited in claim 44, wherein the selectable marker is neomycin phosphotransferase.

46. The method a recited in claim 45, wherein the vector further comprises heterologous DNA, in additional to the DNA encoding the selectable marker, wherein the heterologous DNA encodes a protein that, when expressed, confers a desired trait to transformed enbryogenic callus or plants derived from transformed embryogenic callus.

47. The method as recited in claim 46, wherein the heterologous DNA encodes a protein that confers antibiotic resistance.

48. The method as recited in claim 47, wherein the antibiotic resistance is kanamycin resistance or G418 resistance.

49. The method as recited in claim 46, wherein the heterologous DNA encodes neomycin phosphotransferase.

50. The method as recited in claim 46, wherein the heterologous DNA encodes a protein that confers herbicide resistance.

51. The method as recited in claim 50, wherein the herbicide resistance is glyphosate resistance.

52. The method as recited in claim 46, wherein the heterologous DNA comprises a mutant aroA gene.

53. The method as recited in claim 46, wherein the heterologous DNA encodes an altered form of 5-enolpyruvyl shikimate 3-phosphate synthase.

54. A method for producing embryogenic cotton callus comprising the steps of:

providing a cotton explant from a source selected from the group consisting of cotyledon, immature zygotic embryos and mixtures thereof;

incubating the cotton explant in the presence of a vector comprising DNA encoding a selectable marker to produce a treated explant;

growing the treated explant to produce callus; and selecting transformed embryogenic callus.

55. The method as recited in claim 54, wherein the vector is derived from an Agrobacterium plasmid.

56. The method as recited in claim 54, further comprising the step of incubating the treated explant in a callus growth medium toxic to Agrobacterium but non-toxic to the explant or callus.

57. The method as recited in claim 54, wherein the treated explant is grown under illumination cycles of 16 hours of light and 8 hours of dark.

58. The method as recited in claim 57, wherein the treated explant is grown in a light intensity of 2,000 to 4,000 lux during the hours of light of the illumination cycles.

59. The method as recited in claim 57, wherein the treated explant is grown in a light intensity of 3,000 to 4,000 lux during the hours of light of the illumination cycles.

60. The method as recited in claim 54, wherein the treated explant is grown at a temperature of 25 ° C. to 35° C.

61. The method as recited in claim 54, wherein the treated explant is grown at a temperature of 30° C.

62. The method as recited in claim 54, wherein the treated explant is grown for about 3 to 4 weeks to produce callus.

63. The method as recited in claim 54, wherein treated explant is grown in a sucrose-free, first callus growth medium supplemented with thiamine, kinetin, inositol and naphthaleneacetic acid and glucose as the primary carbon source until the secretion of phenolic compounds ceases and callus is formed.

64. The method as recited in claim 54, further comprising the step of, after the secretion of phenolic compounds ceases, transferring the callus to a second callus growth medium for the formation of embryogenic callus.

65. The method as recited in claim 64, wherein sucrose is the primary carbon source in the second callus growth medium.

66. The method as recited claim 65, wherein the second callus growth medium is supplemented with thiamine, kinetin, inositol and naphthaleneacetic acid.

67. The method as recited in claim 58, further comprising the steps of:

obtaining a transformed embryo from the transformed embryogenic callus, transferring the transformed embryo to an embryo germination medium, and culturing the transformed embryo on the embryo germination medium until a plantlet is formed from the transformed embryo.

68. The method as recited in claim 67, wherein the embryo germination medium is supplemented with casein hydrolysate and a source of ammonia.

69. The method as recited in claim 67, wherein the transformed embryo is cultured under illumination cycles of 16 hours of light and 8 hours of dark.

70. The method as recited in claim 69, wherein the transformed embryo is cultured in a light intensity of 2,000 to 4,000 lux during the hours of light of the illumination cycles.

71. The method as recited in claim 69, wherein the transformed embryo is cultured in a light intensify of 3,000 to 4,000 lux during the hours of light of the illumination cycles.

72. The method as recited in claim 67, wherein the transformed embryo is cultured at a temperature of 25° C. to 35° C.

73. The method as recited in claim 67, wherein the transformed embryo is cultured at a temperature of 30° C.

74. The method as recited in claim 67, further comprising the step of culturing the transformed embryo for about 2 to 3 weeks to produce plantlets.

75. The method as recited in claim 67, further comprising the steps of transferring the plantlet to soil and growing the plantlet until the plantlet is sufficiently matured to withstand transfer to a greenhouse or field for growth to final maturity.

76. The method as recited in claim 54, further comprising the steps of:

sterilizing a cotton seed;

transferring the seed to a seed germination medium;

growing the seed in the seed germination medium until a seedling is produced; and preparing explants from the seedling.

77. The method as recited in claim 56, wherein the callus growth medium toxic to Agrobacterium comprises cefotaxime.

78. The method as recited in claim 54, wherein the treated explant is grown on a first callus growth medium that is a Murashige and Skoog medium supplemented with naphthaleneacetic acid in an amount of 1 to 10 mg/l.

79. The method as recited in claim 54, wherein the selectable marker confers resistance to a compound toxic to wild type callus.

80. The method recited in claim 54, wherein the selectable marker is neomycin phosphotransferase.

81. The method as recited in claim 54, wherein the vector further comprises heterologous DNA in addition to the DNA encoding the selectable marker, wherein the heterologous DNA encodes a protein that, when expressed, confers a desired trait to transformed embryogenic callus or plants derived from transformed embryogenic callus.

82. The method as recited in claim 81, wherein the heterologous DNA encodes a protein that confers antibiotic resistance.

83. The method as recited in claim 82, wherein the antibiotic resistance is kanamycin resistance or G418 resistance.

84. The method as recited in claim 81, wherein the heterologous DNA encodes neomycin phosphotransferase.

85. The method as recited in claim 81, wherein the heterologous DNA encodes a protein that confers herbicide resistance.

86. The method as recited in claim 85, wherein the herbicide resistance is glyphosate resistance.

87. The method as recited in claim 81, wherein the heterologous DNA comprises a mutant aroA gene.

88. The method as recited in claim 81, wherein the heterologous DNA encodes an altered form of 5-enolpyruvyl shikimate 3-phosphate synthase.

89. The method as recited in claim 54, wherein the transformed callus is selected by growing the transformed callus in a medium supplemented with a compound toxic to non-transformed callus but non-toxic to the transformed callus.

90. The method as recited in claim 89, wherein the transformed callus is selected by growing the callus in a medium supplemented with kanamycin or G418.

91. A method for producing transgenic embryogenic cotton callus comprising the steps of:

providing an embryogenic cotton callus in or on a medium;

incubating the embryogenic cotton callus in the presence of an Agrobacterium comprising a vector comprising DNA encoding a selectable marker to produce a treated embryogenic cotton callus; and selecting transformed embryogenic cotton callus.

92. The method as recited in claim 91, wherein the selectable marker confers resistance to a compound toxic to non-transformed callus.

93. The method as recited in claim 92, wherein the selectable marker is neomycin phosphotransferase.

94. The method as recited in claim 91, wherein the vector further comprises heterologous DNA, in addition to the DNA encoding the selectable marker, wherein the heterologous DNA encodes a protein that, when expressed, confers a desired trait to transformed embryogenic callus or plants derived from transformed enbryogenic callus.

95. The method as recited in claim 94, wherein the heterologous DNA encode a protein that confers antibiotic resistance.

96. The method as recited in claim 95, wherein the antibiotic resistance is kanamycin resistance or G418 resistance.

97. The method as recited in claim 94, wherein the heterologous DNA encodes neomycin phosphotransferase.

98. The method as recited in claim 94, wherein the heterologous DNA encodes a protein that confers herbicide resistance.

99. The method as recited in claim 98, wherein the herbicide resistance is glyphosate resistance.

100. The method as recited in claim 94, wherein the heterologous DNA comprises a mutant aroA gene.

101. The method as recited in claim 94, wherein the heterologous DNA encodes an altered form of 5-enolpyruvyl shikimate 3-phosphate synthase.

\* \* \* \* \*

UNITED STATES PATENT AND TRADEMARK OFFICE
CERTIFICATE OF CORRECTION

PATENT NO. : 6,620,990 B1
DATED : September 16, 2003
INVENTOR(S) : Thirumale Srinivasa Rangan et al.

It is certified that error appears in the above-identified patent and that said Letters Patent is hereby corrected as shown below:

Column 1,
Line 57, "in vitro somatic." should read -- in vitro somatic --.

Column 2,
Lines 32 and 33, "germinating seed lings" should read -- germinating seed-lings --.

Column 5,
Line 46, "$Na_2MoO_4.2H_2O$   2.5mg" should read -- $Na_2MoO_4.2H_2O$   25mg --.

Column 6,
Line 50, "$CuSo_4.5H_2O$" should read -- $CuSO_4.5H_2O$ --.

Column 8,
Line 16, "B3991, GC356, GCS10" should read -- B3991, GC356, GC510 --.

Column 14,
Line 29, "which they have been grown." should read -- which they have been: --.

Column 15,
Lines 22 and 23, "+ indicates                    -- + indicated
                 - indicates"     should read    - indicated --.

Column 16,
Line 30, "well as the pAI4404" should read -- as well as the pAL4404 --.
Line 30, "nopaline syntliase" should read -- nopaline synthase --.
Line 32, "region Crom Tn5" should read -- region from Tn5 --.
Line 40, "Expression of the nos/nco/nos" should read -- Expression of the nos/neo/nos --.

Column 18,
Lines 41 and 42, "Dr. J. Nueesch, CIBA-S Geigy, Ltd." should read
Dr. J. Nueesch, CIBA-Geigy, Ltd. --.

Column 25,
Lines 57 and 58, "these A grobracierin were intiated" should read -- these
*Agrobacteria* were initiated --.

Column 26,
Lines 3 and 4, "*Manduca sexta* or *IIeliothis virescens*" should read
-- *Manduca sexta* or *Heliothis virescens* --.

UNITED STATES PATENT AND TRADEMARK OFFICE
CERTIFICATE OF CORRECTION

PATENT NO.    : 6,620,990 B1
DATED         : September 16, 2003
INVENTOR(S)   : Thirumale Srinivasa Rangan et al.

It is certified that error appears in the above-identified patent and that said Letters Patent is hereby corrected as shown below:

<u>Column 27,</u>
Line 58, "ORC BLANCO PIMA" should read -- ORO BLANCO PIMA --.

<u>Column 36,</u>
Line 65, "transformed enbryogenic callus;" should read -- transformed embryogenic callus; --.

<u>Column 37,</u>
Line 14, "comprising the step of:" should read -- comprising the step of: --.
Line 28, "The method a recited in" should read -- The method as recited in --.
Line 29, "DNA, in additional to the DNA" should read -- DNA, in addition to the DNA --.

<u>Column 38,</u>
Line 51, "a light intensify of 3,000" should read -- a light intensity of 3,000 --.

<u>Column 39,</u>
Line 15, "The method recited in" should read -- The method as recited in --.

<u>Column 40,</u>
Line 26, "heterologous DNA encode a protein" should read -- heterologous DNA encodes a protein --.

Signed and Sealed this

Twenty-seventh Day of January, 2004

JON W. DUDAS
*Acting Director of the United States Patent and Trademark Office*

```
                         SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
          (A) LENGTH: 4360 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: Bacillus thuringiensis (xi) SEQUENCE DESCRIPTION: SEQ ID NO:1:

GTTAACACCC TGGGTCAAAA ATTGATATTT AGTAAAATTA GTTGCACTTT GTGCATTTTT     60

TCATAAGATG AGTCATATGT TTTAAATTGT AGTAATGAAA AACAGTATTA TATCATAATG    120

AATTGGTATC TTAATAAAAG AGATGGAGGT AACTTATGGA TAACAATCCG AACATCAATG    180

AATGCATTCC TTATAATTGT TTAAGTAACC CTGAAGTAGA AGTATTAGGT GGAGAAAGAA    240

TAGAAACTGG TTACACCCCA ATCGATATTT CCTTGTCGCT AACGCAATTT CTTTTGAGTG    300

AATTTGTTCC CGGTGCTGGA TTTGTGTTAG GACTAGTTGA TATAATATGG GGAATTTTTG    360
```

```
GTCCCTCTCA ATGGGACGCA TTTCCTGTAC AAATTGAACA GTTAATTAAC CAAAGAATAG     420

AAGAATTCGC TAGGAACCAA GCCATTTCTA GATTAGAAGG ACTAAGCAAT CTTTATCAAA     480

TTTACGCAGA ATCTTTTAGA GAGTGGGAAG CAGATCCTAC TAATCCAGCA TTAAGAGAAG    540

AGATGCGTAT TCAATTCAAT GACATGAACA GTGCCCTTAC AACCGCTATT CCTCTTTTTG    600

CAGTTCAAAA TTATCAAGTT CCTCTTTTAT CAGTATATGT TCAAGCTGCA AATTTACATT    660

TATCAGTTTT GAGAGATGTT TCAGTGTTTG ACAAAGGTG GGGATTTGAT GCCGCGACTA    720

TCAATAGTCG TTATAATGAT TTAACTAGGC TTATTGGCAA CTATACAGAT CATGCTGTAC    780

GCTGGTACAA TACGGGATTA GAGCGTGTAT GGGGACCGGA TTCTAGAGAT TGGATAAGAT    840

ATAATCAATT TAGAAGAGAA TTAACACTAA CTGTATTAGA TATCGTTTCT CTATTTCCGA    900

ACTATGATAG TAGAACGTAT CCAATTCGAA CAGTTTCCCA ATTAACAAGA GAAATTTATA    960

CAAACCCAGT ATTAGAAAAT TTTGATGGTA GTTTTCGAGG CTCGGCTCAG GGCATAGAAG   1020

GAAGTATTAG GAGTCCACAT TTGATGGATA TACTTAACAG TATAACCATC TATACGGATG   1080

CTCATAGAGG AGAATATTAT TGGTCAGGGC ATCAAATAAT GGCTTCTCCT GTAGGGTTTT   1140

CGGGGCCAGA ATTCACTTTT CCGCTATATG GAACTATGGG AAATGCAGCT CCACAACAAC   1200

GAATTGTTGC TCAACTAGGT CAGGGCGTGT ATAGAACATT ATCGTCCACT TTATGTAGAA   1260

GACCTTTTAA TATAGGGATA AATAATCAAC AACTATCTGT TCTTGACGGG ACAGAATTTG   1320

CTTATGGAAC CTCCTCAAAT TTGCCATCCG CTGTATACAG AAAAAGCGGA ACGGTAGATT   1380

CGCTGGATGA AATACCGCCA CAGAATAACA ACGTGCCACC TAGGCAAGGA TTTAGTCATC   1440

GATTAAGCCA TGTTTCAATG TTTCGTTCAG GCTTTAGTAA TAGTAGTGTA AGTATAATAA   1500

GAGCTCCTAT GTTCTCTTGG ATACATCGTA GTGCTGAATT TAATAATATA ATTCCTTCAT   1560

CACAAATTAC ACAAATACCT TTAACAAAAT CTACTAATCT TGGCTCTGGA ACTTCTGTCG   1620

TTAAAGGACC AGGATTTACA GGAGGAGATA TTCTTCGAAG AACTTCACCT GGCCAGATTT   1680

CAACCTTAAG AGTAAATATT ACTGCACCAT TATCACAAAG ATATCGGGTA AGAATTCGCT   1740

ACGCTTCTAC CACAAATTTA CAATTCCATA CATCAATTGA CGGAAGACCT ATTAATCAGG   1800

GGAATTTTTC AGCAACTATG AGTAGTGGGA GTAATTTACA GTCCGGAAGC TTTAGGACTG   1860

TAGGTTTTAC TACTCCGTTT AACTTTTCAA ATGGATCAAG TGTATTTACG TTAAGTGCTC   1920

ATGTCTTCAA TTCAGGCAAT GAAGTTTATA TAGATCGAAT TGAATTTGTT CCGGCAGAAG   1980

TAACCTTTGA GGCAGAATAT GATTTAGAAA GAGCACAAAA GGCGGTGAAT GAGCTGTTTA   2040

CTTCTTCCAA TCAAATCGGG TTAAAAACAG ATGTGACGGA TTATCATATT GATCAAGTAT   2100

CCAATTTAGT TGAGTGTTTA TCTGATGAAT TTTGTCTGGA TGAAAAAAAA GAATTGTCCG   2160

AGAAAGTCAA ACATGCGAAG CGACTTAGTG ATGAGCGGAA TTTACTTCAA GATCCAAACT   2220

TTAGAGGGAT CAATAGAGAA CTAGACCGTG GCTGGAGAGG AAGTACGGAT ATTACCATCC   2280

AAGGAGGCGA TGACGTATTC AAAGAGAATT ACGTTACGCT ATTGGGTACC TTTGATGAGT   2340

GCTATCCAAC GTATTTATAT CAAAAAATAG ATGAGTCGAA ATTAAAAGCC TATACCCGTT   2400

ACCAATTAAG AGGGTATATC GAAGATAGTC AAGACTTAGA AATCTATTTA ATTCGCTACA   2460

ATGCCAAACA CGAAACAGTA AATGTGCCAG GTACGGGTTC CTTATGGCCG CTTTCAGCCC   2520

CAAGTCCAAT CGGAAAATGT GCCCATCATT CCCATCATTT CTCCTTGGAC ATTGATGTTG   2580

GATGTACAGA CTTAAATGAG GACTTAGGTG TATGGGTGAT ATTCAAGATT AAGACGCAAG   2640

ATGGCCATGC AAGACTAGGA AATCTAGAAT TTCTCGAAGA GAAACCATTA GTAGGAGAAG   2700
```

-continued

```
CACTAGCTCG TGTGAAAAGA GCGGAGAAAA AATGGAGAGA CAAACGTGAA AAATTGGAAT    2760

GGGAAACAAA TATTGTTTAT AAAGAGGCAA AAGAATCTGT AGATGCTTTA TTTGTAAACT    2820

CTCAATATGA TAGATTACAA GCGGATACCA ACATCGCGAT GATTCATGCG GCAGATAAAC    2880

GCGTTCATAG CATTCGAGAA GCTTATCTGC CTGAGCTGTC TGTGATTCCG GGTGTCAATG    2940

CGGCTATTTT TGAAGAATTA GAAGGGCGTA TTTTCACTGC ATTCTCCCTA TATGATGCGA    3000

GAAATGTCAT TAAAAATGGT GATTTTAATA ATGGCTTATC CTGCTGGAAC GTGAAAGGGC    3060

ATGTAGATGT AGAAGAACAA AACAACCACC GTTCGGTCCT TGTTGTTCCG GAATGGGAAG    3120

CAGAAGTGTC ACAAGAAGTT CGTGTCTGTC CGGGTCGTGG CTATATCCTT CGTGTCACAG    3180

CGTACAAGGA GGGATATGGA GAAGGTTGCG TAACCATTCA TGAGATCGAG AACAATACAG    3240

ACGAACTGAA GTTTAGCAAC TGTGTAGAAG AGGAAGTATA TCCAAACAAC ACGGTAACGT    3300

GTAATGATTA TACTGCGACT CAAGAAGAAT ATGAGGGTAC GTACACTTCT CGTAATCGAG    3360

GATATGACGG AGCCTATGAA AGCAATTCTT CTGTACCAGC TGATTATGCA TCAGCCTATG    3420

AAGAAAAAGC ATATACAGAT GGACGAAGAG ACAATCCTTG TGAATCTAAC AGAGGATATG    3480

GGGATTACAC ACCACTACCA GCTGGCTATG TGACAAAAGA ATTAGAGTAC TTCCCAGAAA    3540

CCGATAAGGT ATGGATTGAG ATCGGAGAAA CGGAAGGAAC ATTCAACGTG GACAGCGTGG    3600

AATTACTTCT TATGGAGGAA TAATATATGC TTTATAATGT AAGGTGTGCA AATAAAGAAT    3660

GATTACTGAC TTGTATTGAC AGATAAATAA GGAAATTTTT ATATGAATAA AAAACGGGCA    3720

TCACTCTTAA AAGAATGATG TCCGTTTTTT GTATGATTTA ACGAGTGATA TTTAAATGTT    3780

TTTTTTGCGA AGGCTTTACT TAACGGGGTA CCGCCACATG CCCATCAACT TAAGAATTTG    3840

CACTACCCCC AAGTGTCAAA AAACGTTATT CTTTCTAAAA AGCTAGCTAG AAAGGATGAC    3900

ATTTTTTATG AATCTTTCAA TTCAAGATGA ATTACAACTA TTTTCTGAAG AGCTGTATCG    3960

TCATTTAACC CCTTCTCTTT TGGAAGAACT CGCTAAAGAA TTAGGTTTTG TAAAAAGAAA    4020

ACGAAAGTTT TCAGGAAATG AATTAGCTAC CATATGTATC TGGGGCAGTC AACGTACAGC    4080

GAGTGATTCT CTCGTTCGAC TATGCAGTCA ATTACACGCC GCCACAGCAC TCTTATGAGT    4140

CCAGAAGGAC TCAATAAACG CTTTGATAAA AAAGCGGTTG AATTTTTGAA ATATATTTTT    4200

TCTGCATTAT GGAAAAGTAA ACTTTGTAAA ACATCAGCCA TTTCAAGTGC AGCACTCACG    4260

TATTTTCAAC GAATCCGTAT TTTAGATGCG ACGATTTTCC AAGTACCGAA ACATTTAGCA    4320

CATGTATATC CTGGGTCAGG TGGTTGTGCA CAAACTGCAG                         4360
```